(12) United States Patent
Ghatnekar et al.

(10) Patent No.: US 12,138,293 B2
(45) Date of Patent: Nov. 12, 2024

(54) PEPTIDE FORMULATIONS AND OPHTHALMIC USES THEREOF

(71) Applicant: XEQUEL BIO, INC., Mount Pleasant, SC (US)

(72) Inventors: Gautam Ghatnekar, Mt. Pleasant, SC (US); Christina Grek, Mt. Pleasant, SC (US)

(73) Assignee: XEQUEL BIO, INC., Mount Pleasant, SC (US)

( * ) Notice: Subject to any disclaimer, the term of this patent is extended or adjusted under 35 U.S.C. 154(b) by 58 days.

(21) Appl. No.: 17/508,388

(22) Filed: Oct. 22, 2021

(65) Prior Publication Data

US 2022/0241371 A1     Aug. 4, 2022

Related U.S. Application Data

(60) Provisional application No. 63/104,086, filed on Oct. 22, 2020.

(51) Int. Cl.

| | |
|---|---|
| *A61K 38/17* | (2006.01) |
| *A61K 9/00* | (2006.01) |
| *A61K 47/02* | (2006.01) |
| *A61K 47/38* | (2006.01) |
| *A61P 27/02* | (2006.01) |

(52) U.S. Cl.
CPC ........ *A61K 38/1709* (2013.01); *A61K 9/0048* (2013.01); *A61K 47/02* (2013.01); *A61K 47/38* (2013.01); *A61P 27/02* (2018.01)

(58) Field of Classification Search
None
See application file for complete search history.

(56) References Cited

U.S. PATENT DOCUMENTS

| | | |
|---|---|---|
| 5,234,809 A | 8/1993 | Boom et al. |
| 5,338,665 A | 8/1994 | Schatz et al. |
| 5,401,504 A | 3/1995 | Das et al. |
| 6,080,724 A | 6/2000 | Chassaing et al. |
| 6,685,971 B2 | 2/2004 | Xu et al. |
| 6,991,813 B2 | 1/2006 | Xu et al. |
| 7,098,190 B1 | 8/2006 | Becker et al. |
| 7,415,306 B2 | 8/2008 | Levin et al. |
| 7,615,540 B2 | 11/2009 | Green |
| 7,786,074 B2 | 8/2010 | Gourdie et al. |
| 7,879,811 B2 | 2/2011 | Green |
| 7,888,319 B2 | 2/2011 | Gourdie et al. |
| 7,919,474 B2 | 4/2011 | Green |
| 8,357,668 B2 | 1/2013 | Gourdie et al. |
| 8,809,257 B2 | 8/2014 | Ghatnekar |
| 8,846,605 B2 | 9/2014 | Ghatnekar |
| 8,859,733 B2 | 10/2014 | Ghatnekar |
| 8,916,515 B2 | 12/2014 | Ghatnekar |
| 9,161,984 B2 | 10/2015 | Ghatnekar |
| 9,394,351 B2 | 7/2016 | Ghatnekar et al. |
| 9,408,381 B2 | 8/2016 | Ghatnekar et al. |
| 9,844,214 B2 | 12/2017 | Ghatnekar et al. |
| 9,855,313 B2 | 1/2018 | Ghatnekar et al. |
| 10,398,140 B2 | 9/2019 | Ghatnekar et al. |
| 10,398,757 B2 | 9/2019 | Ghatnekar et al. |
| 10,632,173 B2 | 4/2020 | Ghatnekar |
| 11,524,049 B2 | 12/2022 | Ghatnekar |
| 2002/0115589 A1 | 8/2002 | Nixon et al. |
| 2003/0108886 A1 | 6/2003 | Finn et al. |
| 2003/0215424 A1 | 11/2003 | Seul et al. |
| 2003/0219826 A1 | 11/2003 | Robbins et al. |
| 2004/0162232 A1 | 8/2004 | Mitts et al. |
| 2005/0053918 A1 | 3/2005 | Barnea et al. |
| 2005/0075280 A1 | 4/2005 | Larsen et al. |
| 2007/0072819 A1 | 3/2007 | Becker |
| 2007/0072820 A1 | 3/2007 | Green |
| 2007/0104665 A1 | 5/2007 | Jones et al. |
| 2007/0244062 A1 | 10/2007 | Laux |
| 2008/0095819 A1 | 4/2008 | Gourdie et al. |
| 2008/0242631 A1 | 10/2008 | Becker et al. |
| 2008/0249041 A1 | 10/2008 | Becker |
| 2008/0299228 A1 | 12/2008 | Harris et al. |
| 2009/0131313 A1 | 5/2009 | Sosne et al. |
| 2009/0142295 A1 | 6/2009 | Becker |
| 2009/0215665 A1 | 8/2009 | Gourdie et al. |
| 2009/0220450 A1 | 9/2009 | Green et al. |
| 2010/0093691 A1 | 4/2010 | Beck et al. |
| 2010/0279921 A1 | 11/2010 | Duft |
| 2010/0317725 A1 | 12/2010 | Garner et al. |

(Continued)

FOREIGN PATENT DOCUMENTS

| | | |
|---|---|---|
| CA | 1295242 C | 2/1992 |
| CA | 2592285 A1 | 12/2008 |

(Continued)

OTHER PUBLICATIONS

Terreni et al. "Development and Characterization of a Novel Peptide-Loaded Antimicrobial Ocular Insert" Biomolecules 10:664 ( Year: 2020).*

Age-Related Eye Diseases, www.nei.nih.gov, attached as pdf, available at http://www.nei.nih.gov/healthyeyes/aging_eye.asp, last visited May 6, 2013.

Akbari et al., "Effects of vacuum-compression therapy on healing of diabetic foot ulcers: Randomized controlled trial," J. Rehab. Res. Devel. 44:631-636 (2007).

Alonso and Fuchs. "Stem cells of the skin epithelium", Proc Natl Acad Sci USA.(2003), 100 (Suppl 1): 11830-11835.

(Continued)

*Primary Examiner* — Sudhakar Katakam
*Assistant Examiner* — Zachary J Miknis
(74) *Attorney, Agent, or Firm* — COOLEY LLP

(57) ABSTRACT

This disclosure provides formulations suitable for topical ophthalmic delivery of peptide therapeutics. The disclosure also provides compositions and methods for treating ocular injury. The compositions and formulations may include therapeutically active alpha connexin peptides.

23 Claims, 7 Drawing Sheets
Specification includes a Sequence Listing.

(56) References Cited

U.S. PATENT DOCUMENTS

| | | |
|---|---|---|
| 2011/0038920 A1 | 2/2011 | Mori et al. |
| 2011/0059173 A1 | 3/2011 | Gourdie et al. |
| 2011/0065770 A1 | 3/2011 | Becker |
| 2011/0092449 A1 | 4/2011 | Duft |
| 2011/0130345 A1 | 6/2011 | Rohrer et al. |
| 2011/0130710 A1 | 6/2011 | Becker et al. |
| 2011/0136890 A1 | 6/2011 | Becker et al. |
| 2011/0144182 A1 | 6/2011 | Becker et al. |
| 2011/0166653 A1 | 7/2011 | Becker et al. |
| 2011/0217313 A1 | 9/2011 | Becker et al. |
| 2011/0223204 A1 | 9/2011 | Duft |
| 2011/0243964 A1 | 10/2011 | Duft |
| 2011/0245184 A1 | 10/2011 | Duft |
| 2011/0300130 A1 | 12/2011 | Becker et al. |
| 2013/0177628 A1 | 7/2013 | Ghatnekar |
| 2013/0267471 A1 | 10/2013 | Ghatnekar |
| 2013/0274206 A1 | 10/2013 | Ghatnekar |
| 2014/0018305 A1 | 1/2014 | Rohrer et al. |
| 2014/0038880 A1 | 2/2014 | Ghatnekar |
| 2015/0018284 A1 | 1/2015 | Ghatnekar |
| 2015/0140060 A1 | 5/2015 | Ghatnekar et al. |
| 2015/0174196 A1 | 6/2015 | Gourdie et al. |
| 2016/0058834 A1 | 3/2016 | Ghatnekar |
| 2016/0120171 A1 | 5/2016 | Ghatnekar et al. |
| 2016/0244749 A1 | 8/2016 | Cochran et al. |
| 2017/0128523 A1 | 5/2017 | Ghatnekar et al. |
| 2017/0135334 A1 | 5/2017 | Ghatnekar et al. |
| 2018/0028468 A1* | 2/2018 | Becker ............... D06M 15/507 |
| 2018/0055943 A1 | 3/2018 | Salzman |
| 2018/0071363 A1 | 3/2018 | Ghatnekar et al. |
| 2018/0077923 A1 | 3/2018 | Ghatnekar et al. |
| 2019/0015521 A1 | 1/2019 | Roizman |
| 2020/0263175 A1 | 8/2020 | Green et al. |
| 2021/0128682 A1 | 5/2021 | Ghatnekar |

FOREIGN PATENT DOCUMENTS

| | | |
|---|---|---|
| EP | 0267015 A2 | 5/1988 |
| EP | 0539140 A1 | 4/1993 |
| EP | 1621212 A1 | 2/2006 |
| JP | 2003-238441 A | 8/2003 |
| WO | WO 00/44409 A1 | 8/2000 |
| WO | WO 00/69896 A2 | 11/2000 |
| WO | WO 02/42422 A2 | 5/2002 |
| WO | WO 02/094981 A2 | 11/2002 |
| WO | WO 03/014303 A2 | 2/2003 |
| WO | WO 03/032964 A2 | 4/2003 |
| WO | WO 2006/069181 A2 | 6/2006 |
| WO | WO 2006/134494 A2 | 12/2006 |
| WO | WO 2008/157840 A2 | 12/2008 |
| WO | WO 2009/075881 A2 | 6/2009 |
| WO | WO 2009/085272 A2 | 7/2009 |
| WO | WO 2013/064579 A1 | 5/2013 |
| WO | WO 2013/131040 A1 | 9/2013 |
| WO | WO 2018/151823 A1 | 8/2018 |
| WO | WO 2019/051428 A1 | 3/2019 |
| WO | WO-2020056144 A1 | 3/2020 |
| WO | WO-2022087396 A1 | 4/2022 |

OTHER PUBLICATIONS

American Chemical Society, CAS Quick Reference Guide, CAS2052-1104, pp. 1-22 (Nov. 2004).
Angst et al. "Dissociated spatial patterning of gap junctions and cell adhesion junctions during postnatal differentiation of ventricular myocardium", Circulation Research (1997), 80: 88-94.
Barker and Gourdie. "Connexin Interacting Proteins. In: Heart Cell Coupling and Impulse Propagation in Health and Disease", Eds., De Mello W.C. and Janse M.J., Kluwer, Boston, pp. 25-50.
Barker and Gourdie. "JNK bond regulation: why do mammalian hearts invest in connexin43?" Circ Res. (2002), 91(7): 556-558.
Barker et al. "Increased association of ZO-1 with connexin43 during remodeling of cardiac gap junctions", Circ Res (2002), 90: 317-324.
Barker et al. "Increased co-localization of connexin43 and ZO-1 in dissociated adult myocytes", Cell Commun Adhes. (2001), 8(4-6): 205-8.
Benner, "Expanding the genetic lexicon: incorporating non-standard amino acids into proteins by ribosome-based synthesis," TIB Tech, 12:158-163 (1994).
Bruzzone et al., "Connexin 43 hemi channels mediate Ca2+-regulated transmembrane NAD+ fluxes in intact cells," FASEB J, vol. 15, pp. 10-12 (2001).
Bryant and Sternberg. "Comparison of protein structural profiles by interactive computer graphics", J. Mol. Graphics (1987), 5(1):4-7.
Bucci et al. "In vivo delivery of the caveolin-1 scaffolding domain inhibits nitric oxide synthesis and reduces inflammation", Nat. Med. (2000), 6: 1362-1367.
Bukauskas et al. "Clustering of connexin 43-enhanced green fluorescent protein gap junction (channels and functional coupling in living cells",. Proc Natl Acad Sci USA (2000), 97: 2556-2561.
Anthony-Cahill et al., "Site-specific mutagenesis with unnatural amino acids," TIBS, 14(10):400-403, (1989).
Chen et al. "Molecular transporters for peptides: delivery of a cardioprotective epsilonPKC agonist peptide into cells and intact ischemic heart using a transport system, R(7)", Chem Biol (2001), 8: 1123-1129.
Cherian et al., "Mechanical strain opens connexin 43 hemichannels in osteocytes: a novel mechanism for the release of prostaglandin," Mol Biol Cell, vol. 16, pp. 3100-3106 (2005).
Chien, K.R. "Stem cells: lost in translation", Nature (2004), 428(6983): 607-608.
Chu et al. "Predictive Sensitivity of Human Cancer Cells in vivo Using Semipermeable Polysulfone Fibers", Pharmacology (1998) 56(6): 318-326.
Clay et al., "Primary severe acute respiratory syndrome coronavirus infection limits replication but not lung inflammation upon homologous rechallenge," J Virol, vol. 86, pp. 4234-4244 (2012).
Clay et al., "Severe acute respiratory syndrome-coronavirus infection in aged nonhuman primates is associated with modulated pulmonary and systemic immune responses," Immun Ageing, vol. 11, No. 4, pp. 1-16 (2014).
Connexin 45 (Genbank: AAH66131.1, Connexin 45 [Xenopus tropical is], attached as pdf, also available at http://www.ncbi.nlm.nih.gov/protein/AAH66131.1 (last visited Aug. 22, 2014).
Console et al., "Antennapedia and HIV Transactivator of Transcription (TAT) "Protein Transduction Domains" Promote Endocytosis of High Molecular Weight Cargo upon Binding to Cell Surface Glycosaminoglycans," J. Biol. Chem. 278(37):35109-35114 (2003).
CTRI/2011/09/002004. "To study safety and efficacy of Granexin Gel plus Standard of Care as compared to standard of care alone in reducing scar formation in wounds following laparoscopic surgery", Registered on Sep. 14, 2011, 6 pages. http://www.ctri.nic.in/Clinicaltrials/pmaindet2.php?trialid=3482.
Dang et al. "The carboxy-tail of connexin-43 localizes to the nucleus and inhibits cell growth", Mol Cell Biochem. (2003), 242(1-2): 35-38.
Defamie et al. "Disruption of gap junctional intercellular communication by lindane is associated with aberrant localization of connexin43 and zonula occludens-1 in 42GPA9 Sertoli cells", Carcinogenesis (2001), 22: 1537-1542.
Derossi et al. "The third helix of Antennapedia homeodomain translocates through biological membranes", J Biol. Chem. (1994), 269(14, Issue 8): 10444-10450.
Dev, K.K. "Making protein interactions druggable: targeting PDZ domains", Nat Rev Drug Discov. (2004), 3(12): 1047-56.
Diegelmann and Evans. "Wound Healing: An Overview of Acute, Fibrotic and Delayed Healing", Frontiers Biosci. (2004), 9: 283-289.
Duffy et al. "Formation of the gap junction nexus: binding partners for connexins", J Physiol—Paris 96 (2002), pp. 243-249.
Duffy et al. "Regulation of connexin43 protein complexes by intracellular acidification", Circ. Res. (2004), 94: 215-222.
Dupont et al. "Altered connexin expression in human congestive heart failure", J. Mol Cell Cardiol (2002), 33: 359-371.
Elmquist et al. "VE-cadherin-derived cell-penetrating peptide, pVEC, with carrier functions", Exp. Cell Res. (2001), 269: 237-244.

(56) References Cited

OTHER PUBLICATIONS

Epstein, "Cutaneous Wound Healing",New. Engl. J. Med. (1999), 341(10): 738-746.
European Search Report, 7 pages, EP appl. No. 10185428.9 mailed Dec. 27, 2011.
European Search Report, 7 pages, EP application No. 13755720.3, mailed Dec. 9, 2015.
European Search Report, 9 pages, EP appl. No. 10185372.9 mailed May 25, 2011.
European Search Report, 9 pages, EP appl. No. 10185398.4 mailed Dec. 23, 2011.
Evans et al., "Connexin mimetic peptides: specific inhibitors of gap-junctional intercellular communication," Biochemical Society transactions, vol. 29, pp. 606-612 (2001).
Evans and Martin. "Gap junctions: structure and function", Mol Membr Biol (2002), 19: 121-136.
EyeSight.Org (FAQs; EYESIGHT.ORG (Feb. 1, 2001 ), attached as pdf, 3 pages, also available at http://www.eyesight.org/Macular_Degeneration/FAQ/faq.html (last visited Apr. 27, 2015).
Fanning et al. "Isolation and functional characterization of the actin binding region in the tight junction protein ZO-1", Faseb J (2002), 16: 1835-1837.
Fawcett and Asher. "The glial scar and central nervous system repair", Brain Res. Bull. (1999), 49:377-391.
Fischer et al. "Structure-activity relationship of truncated and substituted analogues of the intracellular delivery vector Penetratin", J. Pept. Res. (2000), 55: 163-172.
Fishman et al. "Expression of connexin43 in the developing rat heart", Circulation Research (1991), 68: 782-287.
Fonseca et al. "Upregulation in astrocytic connexin 43 gap junction levels may exacerbate generalized seizures in mesial temporal lobe epilepsy", Brain Research (2002), 1: 105-116.
Frankel and Pabo. "Cellular uptake of the Tat protein from human immunodeficiency Virus", Cell (1988), 55: 1189-1193.
Fromaget et al. "Changes in the expression of connexin 43, a cardiac gap junctional protein, during mouse heart development", J Mol Cell Cardiol. (1990), 22: 1245-1258.
Fromaget et al. "Distribution pattern of connexin 43, a gap junctional protein, during the differentiation of mouse heart myocytes", Differentiation (1992), 51: 9-20.
Fu et al. "CCN3 (NOV) interacts with Connexin43 in C6 glioma cells: possible mechanism of Connexin-mediated growth suppression", J Biol Chem. (2004), 279(35): 36943-36950 (2004).
Fujii et al. "A selective irreversible inhibitor targeting a PDZ protein interaction domain", J Am Chem Soc. (2003), 125(40): 12074-12075.
Gaietta et al. "Multicolor and electron microscopic imaging of connexin trafficking", Science (2002), 296: 503-507.
Gao et al. "A cell-penetrating peptide from a novel pVII-pIX phage-displayed random peptide library", Bioorg. Med. Chem. (2002), 10: 4057-4065.
Ghatnekar et al. "Connexin43 carboxyl-terminal peptides reduce scar progenitor and promote regenerative healing following skin wounding", Regen. Med. (2009), 4(2): 205-223.
Ghatnekar et al. "The Effect of a Connexin43-based peptide on the Healing of Chronic Venous Leg Ulcers: A Multicenter, Randomized Trial," Journal of Investigative Dermatology, vol. 135, pp. 289-298 (2014).
Ghatnekar, "Technical Report," submitted in EP appl. no. 10185398.4, 7 pages (Jul. 17, 2012).
Ghatnekar. "Novel Therapeutics for Regenerative Healing", FirstString Research Presentation (2010), 11 pages http://www.charlestondigitalcorridor.com/uploads/presentations/FSR_Presentation.pdf.
Giannos et al., "Formulation Stabilization and Disaggregation of Bevacizumab Ranibizumab and Aflibercept in Dilute Solutions," Pharmaceutical Research, 35(4), p. 78 (2018).
Giaume et al., "Connexins and pannexins in Alzheimer's disease," Neuroscience Letters (2019), 695:100-105.

Giepmans and Moolenaar . "The gap junction protein connexin43 interacts with the second PDZ domain of the zona occludens-1 protein", Curr. Biol. (1998); 8(16): 931-934.
Giepmans et al. "Gap junction protein connexin-43 interacts directly with microtubules", Curr Biol (2001), 11: 1364-1368.
Giepmans, B.N. "Gap junctions and Connexin-interacting proteins", Cardiovasc Res. (2004), 62(2): 233-245.
Gil-Parrado et al. "Calpastatin exon 1 B-derived peptide, a selective inhibitor of calpain: enhancing cell permeability by conjugation with penetratin", Biol Chem (2003), 384: 395-402.
Gonzalez-Mariscal et al. "Tight junction proteins", Prog Biophys Mol Biol (2003), 81: 1-44.
Goodenough and Paul. "Beyond the gap: functions of unpaired connexon channels", Nat Rev Mol Cell Biol (2003), 4: 285-294.
Gourdie et al. "Gap junction distribution in adult mammalian myocardium revealed by an anti-peptide antibody and laser scanning confocal microscopy", Journal of Cell Science (1991), 99: 41-55.
Gourdie et al. "The unstoppable connexin43 carboxyl-terminus: new roles in gap junction organization and wound Healing", Ann NY Acad Sci. (2006), 1080: 49-62.
Gourdie et al. NIH Grant 5R01HL056728 (Oct. 2011), 87 pages.
Green and Loewenstein. "Autonomous functional domains of chemically synthesized human immunodeficiency virus tat trans-activator protein", Cell (1988), 55: 1179-1188.
Green et al. "Validation of immunohistochemical quantification in confocal scanning laser microscopy: A comparative assessment of gap junction size with confocal and ultrastructural techniques", Journal of Histochemistry and Cytochemistry (1993), 41: 1339-1349.
Grek et al., "Topical administration of a connexin43-based peptide augments healing of chronic neuropathic diabetic foot ulcers: A multicenter, randomized trial," Wound Repair Regen, vol. 23, pp. 203-212 (2015).
Grek et al., "A Multicenter Randomized Controlled Trial Evaluating a Cx43-Mimetic Peptide in Cutaneous Scarring," J Invest Dermatol, vol. 137, Issue 3, pp. 620-630 (2017).
Gros et al. "Connexins in mammalian heart function", BioEssays (1996), 18: 719-730.
Gros et al. "Formation and growth of gap junctions in mouse myocardium during ontogenesis: a freeze-cleave study", J Cell Sci (1978), 30: 45-61.
Gu et al., "Pathology and pathogenesis of severe acute respiratory syndrome," Am J Pathol, 170, 1136-1147 (2007).
Haddrill, et al., "Understanding Age-Related Macular Degeneration," AllAboutVision.com, Mar. 2015, attached as PDF, 7 pages, also available at http://www.allaboutvision.com/conditions/amd.htm (last visited Apr. 21, 2015), Hall and Gourdi. "Spatial organization of cardiac gap junctions can affect access resistance", Microsc Res Tech (1995), 31: 446-451.
Hall and Gourdi. "Spatial organization of cardiac gap junctions can affect access resistance", Microsc Res Tech (1995), 31: 446-451.
Harris, A.L. "Emerging issues of connexin channels: biophysics fills the gap", Q Rev Biophys (2001), 34: 325-472.
Hawat et al. "Connexin 43 mimetic peptide Gap26 confers protection to intact heart against myocardial ischemia injury", Pflugers Arch.—Eur. J. Physiol. (2010), 460(3): 583-592.
Hayashi et al. "Cooperative effects of v-myc and c-Ha-ras oncogenes on gap junctional intercellular communication and tumorigenicity in rat liver epithelial cells", Cancer Lett. (1998), 128: 145-154.
Hayashi et al. "Inhibition of gap junctional intercellular communication in rat liver epithelial cells with transforming RNA", FEBS Lett. (2001), 491: 200-206.
Hayashi et al. "Stimulation of cell proliferation and inhibition of gap junctional intercellular communication by linoleic acid", Cancer Lett. (1997), 112: 103-111.
Hill and Preiss, "Functional Analysis of Conserved Histidines in ADP-Glucose Pyrophosphorylase from *Escherichia coli*." Biochemical and Biophysical Research Communications (1998); 244 (2): 573-577.
Hilton et al., "Wound Dressings in Diabetic Foot Disease," Clinical Infectious Diseases, 2004;39:S100-103.

(56) References Cited

OTHER PUBLICATIONS

Hodgins, "Connecting wounds with Connexins", J. Invest. Derm. (2004), 122: ix-x.
Hong and Clayman. "Isolation of a peptide for targeted drug delivery into human head and neck solid tumors", Cancer Res. (2000), 60: 6551-6556.
Hunter et al. "Fusion of GFP to the carboxyl terminus of connexin43 increases gap junction size in HeLa cells", Cell Commun Adhes. (2003), 10(4-6): 211-214.
Hunter et al. "Zonula occludens-1 alters connexin43 gap junction size and organization by influencing channel accretion", Mol Biol Cell. (2005), 16: 5686-98. Epub Sep. 29, 2005.
Hutchinson and Hayden. "The prediction of exons through an analysis of spliceable open reading frames", Nucl. Acids Res. (1992), 20(13): 3453-3462.
Hutnik et al. "The Protective Effect of Functional Connexin43 Channels on a Human Epithelial Cell Line Exposed to Oxidative Stress", Invest. Ophthalmol. Visual Sci. (2008), 49(2): 800-806.
Ibba, Biotechnology & Genetic Engineering Reviews, 13:197-216 (1995).
Ibba & Hennecke, Bio/technology, 12: 678-682 (1994).
International Preliminary Report on Patentability for International Application No. PCT/US2005/046442, dated Jun. 26, 2007, 8 pages.
International Preliminary Report on Patentability for International Application No. PCT/US2008/067944, dated Dec. 22, 2009, 6 pages.
International Preliminary Report on Patentability, PCT/US2013/028727 (mailed Sep. 2, 2014).
International Search Report and Written Opinion, PCT/US08/67944, Dec. 12, 2008.
International Search Report and Written Opinion, PCT/US2008/067944, Dec. 12, 2008.
International Search Report and Written Opinion, PCT/US2013/028727 (mailed May 30, 2013).
International Search Report, 4 pages, PCT appl. No. PCT/US2005/046442 (mailed Mar. 26, 2007).
Itoh et al. "Involvement of ZO-1 in cadherin-based cell adhesion through its direct binding to alpha catenin and actin filaments", J Cell Biol (1997), 138: 181-192.
Jin and Lau. "Identification of connexin-interacting proteins: application of the yeast two-hybrid screen", Methods (2000), 20: 219-231.
Johnson et al. "Gap junctions assemble in the presence of cytoskeletal inhibitors, but enhanced assembly requires microtubules", Experimental Cell Research (2002), 275: 67-80.
Jordan et al. "Trafficking, assembly, and function of a connexin43-green fluorescent protein chimera in live mammalian cells", Mol Biol Cell (1999), 10: 2033-2050.
Kajstura et al. "Bone marrow cells differentiate in cardiac cell lineages after infarction independently of cell fusion", Circ Res. (2005), 96(1):127-37.
Kamerzell et al., "Protein-excipient interactions: Mechanisms and biophysical characterization applied to protein formulation development," Advanced Drug Delivery Reviews, 63(13), pp. 1118-1159 (2011).
Kanovsky et al. "Peptides from the amino terminal mdm-2-binding domain of p53, designed from conformational analysis, are selectively cytotoxic to transformed cells", Proc Natl Acad Sci USA (2001), 98: 12438-12443.
Kaprielian et al. "Downregulation of immunodetectable connexin43 and decreased gap junction size in the pathogenesis of chronic hibernation in the human left ventricle", Circulation (1998), 97: 651-660.
Karmel, et al., "Dry AMD: Hope is in the Pipeline," AAO.org, Apr. 2008, also available at http://www.aao.org/publications/eyenet/200804/retina.cfm?RenderForPrint=1 & (past visited Apr. 20, 2015).
Kausalya et al. "Association of ARVCF with zonula occludens (ZO)-1 and ZO-2: binding to PDZ-domain proteins and cell-cell adhesion regulate plasma membrane and nuclear localization of ARVCF", Mol Biol Cell. (2004), 15(12): 5503-5515. Epub Sep. 29, 2004.
Kausalya et al. "Connexin45 directly binds to ZO-1 and localizes to the tight junction region in epithelial MDCK cells", FEBS Letters (2001), 505: 92-96.
Khan et al., "The emergence of a novel coronavirus (SARS-COV-2), their biology and therapeutic options," J Clin Microbiol (2020).
Koval, "Claudin Heterogeneity and Control of Lung Tight Junctions," Annual Review of Physiology, vol. 75, 2013, pp. 551-567.
Kumar and Gilula. "The gap junction communication channel", Cell (1996), 84: 381-388.
Kwak et al. "Inhibition of endothelial wound repair by dominant negative connexin inhibitors", Mol Biol Cell. (2001), 12(4): 831-845.
Kyle, et al., "The N Terminus of Connexin37 Contains an $\alpha$-Helix That Is Required for Channel Function," J. Biol. Chem. 284(30):20418-20427 (2009).
Lagree, et al., "Specific amino-acid residues in the N-terminus and TM3 implicated in channel function and oligomerization compatibility of connexin43," J. Cell Sci. 116:3189-3201 (2003).
Laing et al. "Connexin45 interacts with zonula occludens-1 and connexin43 in osteoblastic cells", J Biol Chem (2001), 276: 23051-23055.
Laird et al. "Expression and imaging of connexin-GFP chimeras in live mammalian cells", Methods Mol Biol (2001), 154: 135-142.
Lampe and Lau. "Regulation of gap junctions by phosphorylation of connexins", Arch Biochem Biophys (2000), 384: 205-215.
Lauf et al. "Dynamic trafficking and delivery of connexons to the plasma membrane and accretion to gap junctions in living cells", Proc Natl Acad Sci USA (2002), 99: 10446-10451.
Lauf et al. "Expression of fluorescently tagged connexins: a novel approach to rescue function of oligomeric DsRed-tagged proteins", FEBS Lett (2001), 498: 11-15.
Lazar, et al., "Transforming growth factor alpha: mutation of aspartic acid 47 and leucine 48 results in different biological activities." Molecular Cellular Biology (1988); 8(3): 1247-1252.
Legato, M.J. "Cellular Mechanisms of Normal Growth in the Mammalian Heart I. Qualitative and Quantitative Features of Ventricular Architecture in the Dog from Birth to Five Months of Age", Circulation Research (1979), 44: 250-262.
Li et al. "Neuronal connexin36 association with zonula occludens-1 protein (ZO-1) in mouse brain and interaction with the first PDZ domain of ZO-1", Eur J Neurosci. (2004), 19(8): 2132-2146.
Lin et al. "Inhibition of nuclear translocation of transcription factor NF-KB by a synthetic peptide containing a cell membrane permeable motif and nuclear localization sequence", J. Biol. Chem. (1995), 270: 14255-14258.
Lin et al., "Hypothesis for potential pathogenesis of SARS-COV-2 infection—a review of immune changes in patients with viral pneumonia," Emerg Microbes Infect, vol. 9, 1-14 (2020).
Liu et al. "A structural basis for the unequal sensitivity of the major cardiac and liver gap junctions to intracellular acidification: the carboxyl tail length", Biophys J (1993), 64: 1422-1433.
Livingstone & Barton, "Protein sequence alignments: a strategy for the hierarchical analysis of residue conservation," CABIOS, vol. 9(6):745-756 (1993).
Lo, C.W. Role of gap junctions in cardiac conduction and development: insights from the connexin knockout mice. Circulation Research (2000), 87: 346-348.
Lofgren, "Leg ulcers. Symptoms of an underlying disorder," Postgrad Med., vol. 76(4):51-54 (Sep. 15, 1984; abstract only).
Lundberg et al. "Cell membrane translocation of the N-terminal (1-28) part of the prion protein", Biochem. Biophys. Res. Commun. (2002), 299: 85-90.
MacRedmond, "Treatment of persistent dry cough: if possible, treat the cause; if not, treat the cough," Monaldi Arch Chest Dis., vol. 54(3):269-74 (Jun. 1999; abstract only).
Mambettsaeva et al. "Expression of Three Functional Domains of Connexin 32 as Thioredoxin Fusion Proteins in *Escherichia coli* and Generation of Antibodies", Prot. Express. Purif. (1997), 11: 26-34.

(56) References Cited

OTHER PUBLICATIONS

Mandal et al., "Ocular delivery of proteins and peptides: Challenges and novel formulation approaches," Advanced drug delivery reviews, vol. 126, pp. 67-95 (2018).
Mansour, "Ocular manifestations of various systemic disorders," Current Opinion in Ophthalmology (1994), vol. 5; VI:105-109.
Martin et al., "Parallels between tissue repair and embryo morphogenesis," Development, vol. 131, Issue 13, pp. 3021-3034 (2004).
Martin, P. "Wound healing—aiming for perfect skin regeneration", Science (1997), 276(5309): 75-81.
Matsushita et al. "Photo-acceleration of protein release from endosome in the protein transduction system", FEBS Lett. (2004), 572: 221-226.
Mcauliffe et al., "Replication of SARS coronavirus administered into the respiratory tract of African Green, rhesus and cynomolgus monkeys," Virology, vol. 330, pp. 8-15 (2004).
MedlinePlus, downloaded 2014. "Acute vs. chronic conditions," on the web at nlm.nih.gov/medlineplus/ency/imagepages/18126.htm.
Merrifield et al. "Endocytic vesicles move at the tips of actin tails in cultured mast cells", Nat Cell Biol (1999), 1: 72-74.
Mitic and Anderson. "Molecular architecture of tight junctions", Annu Rev Physiol (1998), 60: 121-142.
Moorby, C.D. "A connexin 43 mutant lacking the carboxyl cytoplasmic domain inhibits both growth and motility of mouse 3T3 fibroblasts", Mol Carcinog. (2000), 28(1):23-30.
Moore et al., "Impact of the Controlled Release of a Connexin 43Peptide on Corneal Wound Closure in an STZ Model of Type I Diabetes," PLoS One, vol. 9, Issue 1, e86570, 10 pages (2014).
Moore et al., "A synthetic connexin 43 mimetic peptide augments corneal wound healing," Experimental Eye Research, vol. 115, pp. 178-188 (2013).
Morris et al. "A peptide carrier for the delivery of biologically active proteins into mammalian cells", Nature Biotechnol. (2001), 19: 1173-1176.
Moyer et al. "Wound healing: the role of gap junctional communication in rat granulation tissue maturation", Exp. Mol. Pathol. (2002), 72: 10-16.
Murray et al. "Relationship of cytoskeletal filaments to annular gap junction expression in human adrenal cortical tumor cells in culture", Exp Cell Res (1997), 234: 398-404.
Musil and Goodenough. "Biochemical analysis of connexin43 intracellular transport, phosphorylation, and assembly into gap junctional plaques", J Cell Biol (1991), 115: 1357-1374.
Narita, et al., "A natural variant of bovine dopamine β-monooxygenase with phenylalanine as residue 208: purification and characterization of the variant homo- and heterotetramers of (F208)4 and (F208)2(L208)2." FEBS Letters (1996); 396(2-3): 208-212.
Nielsen et al. "Lens connexins alpha3Cx46 and alpha8Cx50 interact with zonula occludens protein-1 (ZO-1)", Mol Biol Cell. (2003), 14(6):2470-2481. Epub Mar. 7, 2003.
Niessen et al., "Selective permeability of different connexin channels to the second messenger inositol 1,4,5-triphosphate," Journal of cell science, vol. 113, Issue. 8, pp. 1365-1372 (2000).
Norenberg, M.D. "Astrocyte responses to CNS injury", J. Neuropathol. Exp. Neurol. (1994), 53: 213-220.
O'Quinn et al. "A peptide mimetic of the connexin43 carboxyl terminus reduces gap junction remodeling and induced arrhythmia following ventricular injury", Circ. Res. (2011), 108(6): 704-715. Epub Jan. 27, 2011.
Obert et al., "Targeting the tight junction protein, zonula occludens-1, with the connexin43 mimetic peptide, αCT1, reduces VEGF-dependent RPE pathophysiology," J Mol Med (Berl), vol. 95, pp. 535-552 (2017).
Occleston et al., "New therapeutics for the prevention and reduction of scarring." Drug Discovery Today (2008); 13(21): 973-981.
Oehlke et al. "Cellular uptake of an a-helical amphipathic model peptide with the potential to deliver polar compounds into the cell interior non-endocytically", Biochim. Biophys. Acta. (1998), 1414: 127-139.
Orlandini and Margaria. "Evaluation of the efficiency of a new hollow fiber plasmapheresis filter", Int J Artif Organs (1983), 6(Suppl 1): 103-106.
Park et al. "Structure-activity analysis of buforin II, a histone H2A-derived antimicrobial peptide: the proline hinge is responsible for the cell-penetrating ability of buforin II", Proc. Natl Acad. Sci. USA (2000), 97: 8245-8250.
Partial European Search Report, 5 pages, EP appl. No. 10185428.9 (mailed Sep. 6, 2011).
Partial European Search Report, 6 pages, EP appl. No. 10185372.9 (mailed Jan. 21, 2011).
Partial European Search Report, 7 pages, EP appl. No. 10185398.4 (mailed Sep. 6, 2011).
Patel, et al., "Ocular Manifestations of Autoimmune Disease," American Family Physician (Sep. 15, 2002), vol. 66(6):991-998.
Pich et al. "Prognostic relevance of cell proliferation in head and neck tumors", Annals of Oncology (2004), 15(9): 1319-1329.
Pooga et al. "Cell penetration by transportan", FASEB J. (1998), 12: 67-77 (1998).
Poss et al. "Heart regeneration in zebrafish", Science (2002), 298(5601): 2188-2190 (2002).
Prochiantz, A. "Homeodomain-derived peptides. In and out of the cells", Ann NY Acad Sci (1999), 886: 172-179.
Qiu et al. "Targeting connexin43 expression accelerates the rate of wound repair", Curr Biol. (2003), 13(19): 1697-1703.
Quintanilla et al., "Understanding Risk Factors for Alzheimer's Disease: Interplay of Neuroinflammation, Connexin-based Communication and Oxidative Stress," Archives of Medical Research (2012), 43:632-644.
Rana et al., "Gap junction hemichannel-mediated release of glutathione from cultured rat astrocytes," Neuroscience letters, vol. 415, pp. 45-48 (2007).
Ramachandran et al., "A novel role for connexin hemichannel in oxidative stress and smoking-induced cell injury," PLoS One, vol. 2, e712, (2007).
Retamal et al., "S-nitrosylation and permeation through connexin 43 hemichannels in astrocytes: induction by oxidant stress and reversal by reducing agents," Proceedings of the National Academy of Sciences of the United States of America, vol. 103, pp. 4475-4480 (2006).
Reiter et al., (1995) Protein Eng. 8: 1323-1331.
Retamal et al., "Opening of connexin 43 hemichannels is increased by lowering intracellular redox potential," Proceedings of the National Academy of Sciences of the United States of America, vol. 104, pp. 8322-8327 (2007).
Rhett et al., "Novel therapies for scar reduction and regenerative healing of skin wounds." Trends in Biotechnology (2008); 26(4): 173-180.
Rhett et al., "Connexin 43 connexon to gap junction transition is regulated by zonula occludens-1," Mol Biol Cell, vol. 22, pp. 1516-1528 (2011).
Rhett et al., "Purinergic Signaling in Early Inflammatory Events of the Foreign Body Response: Modulating Extracellular ATP as an Enabling Technology for Engineered Implants and Tissues," Tissue Engineering, Part B, Reviews, vol. 20, No. 5, pp. 392-402 (2014).
Rousseau, "Hiccups," South Med. J., vol. 88(2): 175-181 (Feb. 1995, abstract only).
Rousselle et al. "New advances in the transport of doxorubicin through the blood-brain barrier by a peptide vector-mediated strategy", Mol. Pharmacol. (2000), 57(4): 679-686.
Saez et al., "Connexin-based gap junction hemichannels: gating mechanisms," Biochimica et biophysica acta, vol. 1711, pp. 215-224 (2005).
Saint-Geniez, et al., "Endogenous VEGF Is Required for Visual Function: Evidence for a Survival Role on Muller Cells and Photoreceptors," PLoS ONE 3(11 ): e3554.doi: 1 0.1371 /journal.pone.0003554 (Nov. 3, 2008).
Saitongdee et al. "Increased connexin43 gap junction protein in hamster cardiomyocytes during cold acclimatization and hibernation", Cardiovasc Res (2000), 47: 108-115.
Sawada et al. "Cytoprotective membrane-permeable peptides designed from the Bax-binding domain of Ku70", Nature Cell Biol. (2003), 5: 352-357.

(56) References Cited

OTHER PUBLICATIONS

Segretain and Falk. "Regulation of connexin biosynthesis, assembly, gap junction formation, and removal", Bioch. Bioph. Acta (2004), 1662: 3-21.
Segretain et al. "A proposed role for ZO-1 in targeting connexin 43 gap junctions to the endocytic pathway", Biochimie. (2004), 86: 241-244.
Sepp et al. "Altered patterns of cardiac intercellular junction distribution in hypertrophic cardiomyopathy", Heart (1996), 76: 412-417.
Severs et al. "Remodelling of gap junctions and connexin expression in heart disease", Biochim Biophys Acta. (2004), 1662: 138-148.
Shao, et al., "Structure and functional studies of N-terminal Cx43 mutants linked to oculodentodigital dysplasia," Mol. Biol. Cell. 23:3312-3321 (2012).
Shibata et al. "Ultrastructural changes during development of gap junctions in rabbit left ventricular myocardial cells", Journal of Ultrastructure Research (1980), 71: 258-271.
Silver and Miller. "Regeneration beyond the glial scar", Nat Rev Neurosci. (2004), 5(2): 146-156.
Simpson et al. "Modulation of cardiac myocyte phenotype in vitro by the composition and orientation of the extracellular matrix", Journal of Cellular Physiology (1994), 161: 89-105.
Singapore Application No. 11201405359Y, Search Report mailed Sep. 10, 2015, 3 pages.
Singapore Application No. 11201405359Y, Written Opinion dated Apr. 11, 2016, 4 pages.
Singapore Application No. 11201405359Y, Written Opinion dated Sep. 10, 2015, 7 pages.
Smith et al. "Altered patterns of gap junction distribution in ischemic heart disease. An immunohistochemical study of human myocardium using laser scanning confocal microscopy", American Journal of Pathology (1991), 139: 801-821.
Songyang et al. "Recognition of unique carboxyl-terminal motifs by distinct PDZ domains", Science (1997), 275: 73-77.
Spach et al. "Electrophysiological effects of remodeling cardiac gap junctions and cell size: experimental and model studies of normal cardiac growth", Circulation Research (2000), 86: 302-311.
Spach, M.S. "Transition from a continuous to discontinuous understanding of cardiac conduction", Circ Res. (2003), 92(2): 125-126.
Stergiopoulos et al. "Hetero-Domain Interactions as a Mechanism for the Regulation of Connexin Channels", Circ. Res. (1999), 84:1144-1155.
Stevenson et al. "Identification of ZO-1: a high molecular weight polypeptide associated with the tight junction (zonula occludens) in a variety of epithelia", J Cell Biol (1986), 103: 755-766.
Stout et al., "Intercellular calcium signaling in astrocytes via ATP release through connexin hemichannels," J Biol Chem, vol. 277, No. 12, pp. 10482-10488 (2002).
Sullivan and Lo. "Expression of a connexin 43/beta-galactosidase fusion protein inhibits gap junctional communication in NIH3T3 cells", J Cell Biol. (1995), 130(2): 419-429.
Supplementary European Search Report, 9 pages, EP appl. No. 08771766.6 (mailed Jul. 4, 2012).
Thomas et al. "Role of cytoskeletal elements in the recruitment of Cx43-GFP and Cx26-YFP into gap junctions", Cell Commun Adhes (2001), 8: 231-236.
Thorson et al., "Insertion of Unnatural Amino Acids Using Chemical Acylation Techniques." Methods in Molecular Biology: Protein Synthesis: Methods and Protocols, 77, 43-73 (1998).
Toyofuku et al. "c-Src regulates the interaction between connexin-43 and ZO-1 in cardiac myocytes", J Biol Chem. (2001), 276(3): 1780-1788. Epub Oct. 16, 2000.
Toyofuku et al. "Direct association of the gap junction protein connexin-43 with ZO-1 in cardiac myocytes", J Biol Chem. (1998), 273(21): 12725-12731.

Traub et al. "Characterization of the gap junction protein connexin37 in murine endothelium, respiratory epithelium, and after transfection in human Hela cells", Eur. J. Cell Biol. (1998), 77: 313-322.
Tsao et al. "A diploid epithelial cell line from normal adult rat liver with phenotypic properties of 'oval' cells", Exp. Cell Res. (1984), 154:38-52.
Tsunoda, et al., "A multivalent PDZ-domain protein assembles signalling complexes in a G-protein-coupled cascade," Nature 388:243-249 (1997).
Unger, et al., "Three-Dimensional Structure of a Recombinant Gap Junction Membrane Channel," Science 283:1176-1180 (1999).
UniProtKB/Swiss-Prot P17302, downloaded Mar. 11, 2010, 16 pages. http://www.uniprot.org/uniprot/P17302.html.
Vigneron et al. "Guanidinium-cholesterol cationic lipids: Efficient vectors for the transfection of eukaryotic cells", Proc. Natl. Acad. Sci. USA. (1998), 93: 9682-9686.
Wadia et al. "Transducible TAT-HA fusogenic peptide enhances escape of TAT-fusion proteins after lipid raft macropinocytosis", Nat Med. (2004), 10(3): 310-315.
Wender et al. "The design, synthesis, and evaluation of molecules that enable or enhance cellular uptake: Peptoid molecular transporters", Proc. Natl. Acad. Sci. USA (2000), 97(24): 13003-13008.
Weymarn, "Process Development for Mannitol Production by Lactic Acid Bacteria", Helinski University of Technology Department of Chemical Technology, Laboratory of Bioprocess Engineering. Technical Biochemistry Report Jan. 2002. Dissertation Apr. 12, 2002.
Wikipedia, downloaded 2014. "Chronic Wound, "on the web at en.wikipedia.org/wiki/Chronic_wound.
Wilgus et al. "Reduction of scar formation in full-thickness wounds with topical celecoxib treatment", Wound Rep Reg (2003), 11: 25-34.
Willecke et al. "Mouse Connexin37: Cloning and Functional Expression of a Gap Junction Gene Highly Expressed in Lung", J. Cell Biol. (1991), 114(5): 1049-1057.
Wright et al. "The connexin mimetic peptide Gap27 increases human dermal fibroblast migration in hyperglycemic and hyperinsulinemic conditions in vitro", Cell Physiol. (2011), 227(1): 77-87. Epub Feb. 24, 2011.
Written Opinion of the International Searching Authority, 7 pages, PCT appl. No. PCT/US2005/046442 (mailed Mar. 26, 2007).
Wu et al., "Use of Pressure Offloading Devices in Diabetic Foot Ulcers," Diabetes Care, Nov. 2008, 31(11):2118-2119.
Wu et al., "Risk Factors Associated With Acute Respiratory Distress Syndrome and Death in Patients With Coronavirus Disease 2019 Pneumonia in Wuhan, China," JAMA Intern Med, Mar. 13, 2020, 180(7):934-943.
Xu et al., "Pathological findings of COVID-19 associated with acute respiratory distress syndrome," Lancet Respir Med, vol. 8, Issue 4, 12 pages (2020).
Yang et al., "Clinical course and outcomes of critically ill patients with SARS-COV-2 pneumonia in Wuhan, China: a single-centered, retrospective, observational study," The Lancet Respiratory Medicine, vol. 8, pp. 475-481 (2020).
Ye et al., "Functional hemichannels in astrocytes: a novel mechanism of glutamate release," J Neurosci, vol. 23, No. 9, pp. 3588-3596 (2003).
Yi et al., "Astroglial Connexins as a Therapeutic Target for Alzheimer's Disease," Current Pharmaceutical Design, 2017, 23, 1-11.
Yoo, D.S. "The dielectric properties of cancerous tissues in a nude mouse xenograft model", Bioelectromagnetics (2004), 25(7): 492-497.
Zaki et al., "A comparison of the effect of viscosity on the precorneal residence of solutions in rabbit and man," Journal of Pharmacy and Pharmacology, 38, pp. 463-466 (1986).
Zarbin. "Current Concepts in the Pathogenesis of Age-Related Macular Degeneration", Arch. Ophthalmol. (2004), 122(4):598-614.
Zoller et al., "New recombinant DNA methodology for protein engineering," Current Opinion in Biotechnology, 3:348-354 (1992).

(56) References Cited

OTHER PUBLICATIONS

Zhang et al., "The Gap Junction-independent Tumor-suppressing Effect of Connexin 43", J. Biol. Chem. (2003), 278(45): 44852-44856.

Zhu et al. "Quantitative Analysis of ZO-1 Co-Localization with Cx43 Gap Junction Plaques in Cultures of Rat Neonatal Cardiomyocytes", Microsc Microanal. (2005), 11(3): 244-248.

Zhu, et al., "Stabilization of Gap and Tight Junctions with ACT1 Reduces Post Transplantation Ischemia Reperfusion Injury" American Society of Transplant Surgeons, Winter Meeting, Jan. 15-18, 2015. Poster with Abstract.

International Preliminary Report on Patentability for International Application No. PCT/US2021/056231 dated May 4, 2023, 6 pages.

International Search Report and Written Opinion for International Application No. PCT/US2021/056231, mailed Feb. 14, 2022, 18 pages.

\* cited by examiner

SEQUENCE LISTING

```
<160> NUMBER OF SEQ ID NOS: 91

<210> SEQ ID NO 1
<211> LENGTH: 20
<212> TYPE: PRT
<213> ORGANISM: Artificial Sequence
<220> FEATURE:
<223> OTHER INFORMATION: synthetic construct

<400> SEQUENCE: 1

Pro Ser Ser Arg Ala Ser Ser Arg Ala Ser Ser Arg Pro Arg Pro Asp
1               5                   10                  15

Asp Leu Glu Ile
            20

<210> SEQ ID NO 2
<211> LENGTH: 9
<212> TYPE: PRT
<213> ORGANISM: Artificial Sequence
<220> FEATURE:
<223> OTHER INFORMATION: synthetic construct

<400> SEQUENCE: 2

Arg Pro Arg Pro Asp Asp Leu Glu Ile
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic construct

<400> SEQUENCE: 3

Arg Pro Arg Pro Asp Asp Leu Glu Val
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: synthetic construct

<400> SEQUENCE: 4

Arg Pro Arg Pro Asp Asp Val Pro Val
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic construct

<400> SEQUENCE: 5

Lys Ala Arg Ser Asp Asp Leu Ser Val
1               5

<210> SEQ ID NO 6
<211> LENGTH: 27
<212> TYPE: DNA
<213> ORGANISM: Artificial Sequence
<220> FEATURE:
<223> OTHER INFORMATION: synthetic construct

<400> SEQUENCE: 6
agacctcggc ctgatgacct ggagatt                                            27

<210> SEQ ID NO 7
<211> LENGTH: 16
<212> TYPE: PRT
<213> ORGANISM: Artificial Sequence
<220> FEATURE:
<223> OTHER INFORMATION: synthetic construct

<400> SEQUENCE: 7

Arg Gln Pro Lys Ile Trp Phe Pro Asn Arg Arg Lys Pro Trp Lys Lys
1               5                   10                  15

<210> SEQ ID NO 8
<211> LENGTH: 36
<212> TYPE: PRT
<213> ORGANISM: Artificial Sequence
<220> FEATURE:
<223> OTHER INFORMATION: synthetic construct

<400> SEQUENCE: 8

Arg Gln Pro Lys Ile Trp Phe Pro Asn Arg Arg Lys Pro Trp Lys Lys
1               5                   10                  15

Pro Ser Ser Arg Ala Ser Ser Arg Ala Ser Ser Arg Pro Arg Pro Asp
            20                  25                  30

Asp Leu Glu Ile
        35

<210> SEQ ID NO 9
<211> LENGTH: 25
<212> TYPE: PRT
<213> ORGANISM: Artificial Sequence
<220> FEATURE:
<223> OTHER INFORMATION: synthetic construct
```

-continued

<400> SEQUENCE: 9

Arg Gln Pro Lys Ile Trp Phe Pro Asn Arg Arg Lys Pro Trp Lys Lys
1               5                   10                  15

Arg Pro Arg Pro Asp Asp Leu Glu Ile
            20                  25

<210> SEQ ID NO 10
<211> LENGTH: 25
<212> TYPE: PRT
<213> ORGANISM: Artificial Sequence
<220> FEATURE:
<223> OTHER INFORMATION: synthetic construct

<400> SEQUENCE: 10

Arg Gln Pro Lys Ile Trp Phe Pro Asn Arg Arg Lys Pro Trp Lys Lys
1               5                   10                  15

Arg Pro Arg Pro Asp Asp Leu Glu Val
            20                  25

<210> SEQ ID NO 11
<211> LENGTH: 25
<212> TYPE: PRT
<213> ORGANISM: Artificial Sequence
<220> FEATURE:
<223> OTHER INFORMATION: synthetic construct

<400> SEQUENCE: 11

Arg Gln Pro Lys Ile Trp Phe Pro Asn Arg Arg Lys Pro Trp Lys Lys
1               5                   10                  15

Arg Pro Arg Pro Asp Asp Val Pro Val
            20                  25

<210> SEQ ID NO 12
<211> LENGTH: 25
<212> TYPE: PRT
<213> ORGANISM: Artificial Sequence
<220> FEATURE:
<223> OTHER INFORMATION: synthetic construct

<400> SEQUENCE: 12

Arg Gln Pro Lys Ile Trp Phe Pro Asn Arg Arg Lys Pro Trp Lys Lys
1               5                   10                  15

Lys Ala Arg Ser Asp Asp Leu Ser Val
            20                  25

<210> SEQ ID NO 13
<211> LENGTH: 74
<212> TYPE: DNA
<213> ORGANISM: Artificial Sequence
<220> FEATURE:
<223> OTHER INFORMATION: synthetic construct

<400> SEQUENCE: 13
cggcagccca agatctggtt ccccaaccgg cggaagccct ggaagaagcg gcccggcccg    60
acgacctgga gatc                                                     74

<210> SEQ ID NO 14
<211> LENGTH: 11
<212> TYPE: PRT
<213> ORGANISM: Artificial Sequence
<220> FEATURE:
<223> OTHER INFORMATION: synthetic construct

<400> SEQUENCE: 14

-continued

Gly Arg Lys Lys Arg Arg Gln Arg Pro Pro Gln
1               5                   10

<210> SEQ ID NO 15
<211> LENGTH: 16
<212> TYPE: PRT
<213> ORGANISM: Artificial Sequence
<220> FEATURE:
<223> OTHER INFORMATION: synthetic construct

<400> SEQUENCE: 15

Arg Gln Ile Lys Ile Trp Phe Gln Asn Arg Arg Met Lys Trp Lys Lys
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: synthetic construct

<400> SEQUENCE: 16

Arg Gln Ile Ala Ile Trp Phe Gln Asn Arg Arg Met Lys Trp Ala Ala
1               5                   10                  15

<210> SEQ ID NO 17
<211> LENGTH: 9
<212> TYPE: PRT
<213> ORGANISM: Artificial Sequence
<220> FEATURE:
<223> OTHER INFORMATION: synthetic construct

<400> SEQUENCE: 17

Arg Lys Lys Arg Arg Gln Arg Arg Arg
1               5

<210> SEQ ID NO 18
<211> LENGTH: 21
<212> TYPE: PRT
<213> ORGANISM: Artificial Sequence
<220> FEATURE:
<223> OTHER INFORMATION: synthetic construct

<400> SEQUENCE: 18

Thr Arg Ser Ser Arg Ala Gly Leu Gln Phe Pro Val Gly Arg Val His
1               5                   10                  15

Arg Leu Leu Arg Lys
            20

<210> SEQ ID NO 19
<211> LENGTH: 26
<212> TYPE: PRT
<213> ORGANISM: Artificial Sequence
<220> FEATURE:
<223> OTHER INFORMATION: synthetic construct

<400> SEQUENCE: 19

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 20
<211> LENGTH: 18
<212> TYPE: PRT

```
<213> ORGANISM: Artificial Sequence
<220> FEATURE:
<223> OTHER INFORMATION: synthetic construct

<400> SEQUENCE: 20

Lys Leu Ala Leu Lys Leu Ala Leu Lys Ala Leu Lys Ala Ala Leu Lys
1               5                   10                  15

Leu Ala

<210> SEQ ID NO 21
<211> LENGTH: 16
<212> TYPE: PRT
<213> ORGANISM: Artificial Sequence
<220> FEATURE:
<223> OTHER INFORMATION: synthetic construct

<400> SEQUENCE: 21

Ala Ala Val Ala Leu Leu Pro Ala Val Leu Leu Ala Leu Leu Ala Pro
1               5                   10                  15

<210> SEQ ID NO 22
<211> LENGTH: 10
<212> TYPE: PRT
<213> ORGANISM: Artificial Sequence
<220> FEATURE:
<223> OTHER INFORMATION: synthetic construct

<400> SEQUENCE: 22

Val Pro Met Leu Lys Pro Met Leu Lys Glu
1               5                   10

<210> SEQ ID NO 23
<211> LENGTH: 28
<212> TYPE: PRT
<213> ORGANISM: Artificial Sequence
<220> FEATURE:
<223> OTHER INFORMATION: synthetic construct

<400> SEQUENCE: 23

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
                20                  25

<210> SEQ ID NO 24
<211> LENGTH: 18
<212> TYPE: PRT
<213> ORGANISM: Artificial Sequence
<220> FEATURE:
<223> OTHER INFORMATION: synthetic construct

<400> SEQUENCE: 24

Leu Leu Ile Ile Leu Arg Arg Arg Ile Arg Lys Gln Ala His Ala His
1               5                   10                  15

Ser Lys

<210> SEQ ID NO 25
<211> LENGTH: 21
<212> TYPE: PRT
<213> ORGANISM: Artificial Sequence
<220> FEATURE:
<223> OTHER INFORMATION: synthetic construct

<400> SEQUENCE: 25

Lys Glu Thr Trp Trp Glu Thr Trp Trp Thr Glu Trp Ser Gln Pro Lys
```

-continued

```
                1               5                  10                 15
Lys Lys Arg Lys Val
            20

<210> SEQ ID NO 26
<211> LENGTH: 18
<212> TYPE: PRT
<213> ORGANISM: Artificial Sequence
<220> FEATURE:
<223> OTHER INFORMATION: synthetic construct

<400> SEQUENCE: 26

Arg Gly Gly Arg Leu Ser Tyr Ser Arg Arg Phe Ser Thr Ser Thr
1               5                   10                  15

Gly Arg

<210> SEQ ID NO 27
<211> LENGTH: 15
<212> TYPE: PRT
<213> ORGANISM: Artificial Sequence
<220> FEATURE:
<223> OTHER INFORMATION: synthetic construct

<400> SEQUENCE: 27

Ser Asp Leu Trp Glu Met Met Met Val Ser Leu Ala Cys Gln Tyr
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: synthetic construct

<400> SEQUENCE: 28

Thr Ser Pro Leu Asn Ile His Asn Gly Gln Lys Leu
1               5                   10

<210> SEQ ID NO 29
<211> LENGTH: 19
<212> TYPE: PRT
<213> ORGANISM: Artificial Sequence
<220> FEATURE:
<223> OTHER INFORMATION: synthetic construct

<400> SEQUENCE: 29

Pro Ser Arg Ala Ser Ser Arg Ala Ser Ser Arg Pro Arg Pro Asp Asp
1               5                   10                  15

Leu Glu Ile

<210> SEQ ID NO 30
<211> LENGTH: 20
<212> TYPE: PRT
<213> ORGANISM: Artificial Sequence
<220> FEATURE:
<223> OTHER INFORMATION: synthetic construct

<400> SEQUENCE: 30

Gly Ser Asn Lys Ser Thr Ala Ser Ser Lys Ser Pro Asp Pro Lys Asn
1               5                   10                  15

Ser Val Trp Ile
            20

<210> SEQ ID NO 31
```

```
<211> LENGTH: 20
<212> TYPE: PRT
<213> ORGANISM: Artificial Sequence
<220> FEATURE:
<223> OTHER INFORMATION: synthetic construct

<400> SEQUENCE: 31

Gly Ser Asn Lys Ser Ser Ala Ser Ser Lys Ser Gly Asp Gly Lys Asn
1               5                   10                  15

Ser Val Trp Ile
            20

<210> SEQ ID NO 32
<211> LENGTH: 21
<212> TYPE: PRT
<213> ORGANISM: Artificial Sequence
<220> FEATURE:
<223> OTHER INFORMATION: synthetic construct

<400> SEQUENCE: 32

Gly Arg Ala Ser Lys Ala Ser Arg Ala Ser Ser Gly Arg Ala Arg Pro
1               5                   10                  15

Glu Asp Leu Ala Ile
            20

<210> SEQ ID NO 33
<211> LENGTH: 13
<212> TYPE: PRT
<213> ORGANISM: Artificial Sequence
<220> FEATURE:
<223> OTHER INFORMATION: synthetic construct

<400> SEQUENCE: 33

Gly Ser Ala Ser Ser Arg Asp Gly Lys Thr Val Trp Ile
1               5                   10

<210> SEQ ID NO 34
<211> LENGTH: 19
<212> TYPE: PRT
<213> ORGANISM: Artificial Sequence
<220> FEATURE:
<223> OTHER INFORMATION: synthetic construct

<400> SEQUENCE: 34

Pro Arg Val Ser Val Pro Asn Phe Gly Arg Thr Gln Ser Ser Asp Ser
1               5                   10                  15

Ala Tyr Val

<210> SEQ ID NO 35
<211> LENGTH: 19
<212> TYPE: PRT
<213> ORGANISM: Artificial Sequence
<220> FEATURE:
<223> OTHER INFORMATION: synthetic construct

<400> SEQUENCE: 35

Pro Arg Met Ser Met Pro Asn Phe Gly Arg Thr Gln Ser Ser Asp Ser
1               5                   10                  15

Ala Tyr Val

<210> SEQ ID NO 36
<211> LENGTH: 21
<212> TYPE: PRT
<213> ORGANISM: Artificial Sequence
<220> FEATURE:
```

```
<223> OTHER INFORMATION: synthetic construct

<400> SEQUENCE: 36

Pro Arg Ala Gly Ser Glu Lys Gly Ser Ala Ser Ser Arg Asp Gly Lys
1               5                   10                  15

Thr Thr Val Trp Ile
            20

<210> SEQ ID NO 37
<211> LENGTH: 23
<212> TYPE: PRT
<213> ORGANISM: Artificial Sequence
<220> FEATURE:
<223> OTHER INFORMATION: synthetic construct

<400> SEQUENCE: 37

Gly Tyr His Ser Asp Lys Arg Arg Leu Ser Lys Ala Ser Ser Lys Ala
1               5                   10                  15

Arg Ser Asp Asp Leu Ser Val
            20

<210> SEQ ID NO 38
<211> LENGTH: 19
<212> TYPE: PRT
<213> ORGANISM: Artificial Sequence
<220> FEATURE:
<223> OTHER INFORMATION: synthetic construct

<400> SEQUENCE: 38

Pro Leu Ser Arg Leu Ser Lys Ala Ser Ser Arg Ala Arg Ser Asp Asp
1               5                   10                  15

Leu Thr Val

<210> SEQ ID NO 39
<211> LENGTH: 22
<212> TYPE: PRT
<213> ORGANISM: Artificial Sequence
<220> FEATURE:
<223> OTHER INFORMATION: synthetic construct

<400> SEQUENCE: 39

Pro Asn His Val Val Ser Leu Thr Asn Asn Leu Ile Gly Arg Arg Val
1               5                   10                  15

Pro Thr Asp Leu Gln Ile
            20

<210> SEQ ID NO 40
<211> LENGTH: 29
<212> TYPE: PRT
<213> ORGANISM: Artificial Sequence
<220> FEATURE:
<223> OTHER INFORMATION: synthetic construct

<400> SEQUENCE: 40

Pro Ser Cys Val Ser Ser Ser Ala Val Leu Thr Thr Ile Cys Ser Ser
1               5                   10                  15

Asp Gln Val Val Pro Val Gly Leu Ser Ser Phe Tyr Met
            20                  25

<210> SEQ ID NO 41
<211> LENGTH: 21
<212> TYPE: PRT
<213> ORGANISM: Artificial Sequence
<220> FEATURE:
```

<223> OTHER INFORMATION: synthetic construct

<400> SEQUENCE: 41

Gly Arg Ser Ser Lys Ala Ser Lys Ser Gly Gly Arg Ala Arg Ala
1               5                   10                  15

Ala Asp Leu Ala Ile
            20

<210> SEQ ID NO 42
<211> LENGTH: 17
<212> TYPE: PRT
<213> ORGANISM: Artificial Sequence
<220> FEATURE:
<223> OTHER INFORMATION: synthetic construct

<400> SEQUENCE: 42

Leu Cys Tyr Leu Leu Ile Arg Tyr Cys Ser Gly Lys Ser Lys Lys Pro
1               5                   10                  15

Val

<210> SEQ ID NO 43
<211> LENGTH: 18
<212> TYPE: PRT
<213> ORGANISM: Artificial Sequence
<220> FEATURE:
<223> OTHER INFORMATION: synthetic construct

<400> SEQUENCE: 43

Gly Gln Lys Pro Pro Ser Arg Pro Ser Ser Ser Ala Ser Lys Lys Gln
1               5                   10                  15

Tyr Val

<210> SEQ ID NO 44
<211> LENGTH: 19
<212> TYPE: PRT
<213> ORGANISM: Artificial Sequence
<220> FEATURE:
<223> OTHER INFORMATION: synthetic construct

<400> SEQUENCE: 44

Ser Ser Arg Ala Ser Ser Arg Ala Ser Ser Arg Pro Arg Pro Asp Asp
1               5                   10                  15

Leu Glu Val

<210> SEQ ID NO 45
<211> LENGTH: 9
<212> TYPE: PRT
<213> ORGANISM: Artificial Sequence
<220> FEATURE:
<223> OTHER INFORMATION: synthetic construct

<400> SEQUENCE: 45

Arg Pro Lys Pro Asp Asp Leu Glu Ile
1               5

<210> SEQ ID NO 46
<211> LENGTH: 19
<212> TYPE: PRT
<213> ORGANISM: Artificial Sequence
<220> FEATURE:
<223> OTHER INFORMATION: synthetic construct

<400> SEQUENCE: 46

Ser Ser Arg Ala Ser Ser Arg Ala Ser Ser Arg Pro Lys Pro Asp Asp

```
1               5                  10                  15

Leu Glu Ile

<210> SEQ ID NO 47
<211> LENGTH: 9
<212> TYPE: PRT
<213> ORGANISM: Artificial Sequence
<220> FEATURE:
<223> OTHER INFORMATION: synthetic construct

<400> SEQUENCE: 47

Arg Pro Lys Pro Asp Asp Leu Asp Ile
1               5

<210> SEQ ID NO 48
<211> LENGTH: 19
<212> TYPE: PRT
<213> ORGANISM: Artificial Sequence
<220> FEATURE:
<223> OTHER INFORMATION: synthetic construct

<400> SEQUENCE: 48

Ser Ser Arg Ala Ser Ser Arg Ala Ser Ser Arg Pro Arg Pro Asp Asp
1               5                  10                  15

Leu Asp Ile

<210> SEQ ID NO 49
<211> LENGTH: 19
<212> TYPE: PRT
<213> ORGANISM: Artificial Sequence
<220> FEATURE:
<223> OTHER INFORMATION: synthetic construct

<400> SEQUENCE: 49

Ser Ser Arg Ala Ser Thr Arg Ala Ser Ser Arg Pro Arg Pro Asp Asp
1               5                  10                  15

Leu Glu Ile

<210> SEQ ID NO 50
<211> LENGTH: 9
<212> TYPE: PRT
<213> ORGANISM: Artificial Sequence
<220> FEATURE:
<223> OTHER INFORMATION: synthetic construct

<400> SEQUENCE: 50

Arg Pro Arg Pro Glu Asp Leu Glu Ile
1               5

<210> SEQ ID NO 51
<211> LENGTH: 19
<212> TYPE: PRT
<213> ORGANISM: Artificial Sequence
<220> FEATURE:
<223> OTHER INFORMATION: synthetic construct

<400> SEQUENCE: 51

Ser Ser Arg Ala Ser Ser Arg Ala Ser Ser Arg Pro Arg Pro Glu Asp
1               5                  10                  15

Leu Glu Ile

<210> SEQ ID NO 52
<211> LENGTH: 9
<212> TYPE: PRT
```

```
<213> ORGANISM: Artificial Sequence
<220> FEATURE:
<223> OTHER INFORMATION: synthetic construct

<400> SEQUENCE: 52

Gly Asp Gly Lys Asn Ser Val Trp Val
1               5

<210> SEQ ID NO 53
<211> LENGTH: 23
<212> TYPE: PRT
<213> ORGANISM: Artificial Sequence
<220> FEATURE:
<223> OTHER INFORMATION: synthetic construct

<400> SEQUENCE: 53

Ser Lys Ala Gly Ser Asn Lys Ser Thr Ala Ser Ser Lys Ser Gly Asp
1               5                   10                  15

Gly Lys Asn Ser Val Trp Val
            20

<210> SEQ ID NO 54
<211> LENGTH: 18
<212> TYPE: PRT
<213> ORGANISM: Artificial Sequence
<220> FEATURE:
<223> OTHER INFORMATION: synthetic construct

<400> SEQUENCE: 54

Gly Gln Lys Pro Pro Ser Arg Pro Ser Ser Ser Ala Ser Lys Lys Leu
1               5                   10                  15

Tyr Val

<210> SEQ ID NO 55
<211> LENGTH: 24
<212> TYPE: PRT
<213> ORGANISM: Artificial Sequence
<220> FEATURE:
<223> OTHER INFORMATION: synthetic construct

<400> SEQUENCE: 55

Arg Gln Pro Lys Ile Trp Phe Pro Asn Arg Arg Lys Pro Trp Lys Ile
1               5                   10                  15

Glu Leu Asp Asp Pro Arg Pro Arg
            20

<210> SEQ ID NO 56
<211> LENGTH: 20
<212> TYPE: PRT
<213> ORGANISM: Artificial Sequence
<220> FEATURE:
<223> OTHER INFORMATION: synthetic construct

<400> SEQUENCE: 56

Gly Arg Lys Lys Arg Arg Gln Arg Pro Pro Gln Arg Pro Arg Pro Asp
1               5                   10                  15

Asp Leu Glu Ile
            20

<210> SEQ ID NO 57
<211> LENGTH: 25
<212> TYPE: PRT
<213> ORGANISM: Artificial Sequence
<220> FEATURE:
<223> OTHER INFORMATION: synthetic construct
```

<400> SEQUENCE: 57

Arg Gln Ile Lys Ile Trp Phe Gln Asn Arg Arg Met Lys Trp Lys Lys
1               5                   10                  15

Arg Pro Arg Pro Asp Asp Leu Glu Ile
            20                  25

<210> SEQ ID NO 58
<211> LENGTH: 25
<212> TYPE: PRT
<213> ORGANISM: Artificial Sequence
<220> FEATURE:
<223> OTHER INFORMATION: synthetic construct

<400> SEQUENCE: 58

Arg Gln Ile Ala Ile Trp Phe Gln Asn Arg Arg Met Lys Trp Ala Ala
1               5                   10                  15

Arg Pro Arg Pro Asp Asp Leu Glu Ile
            20                  25

<210> SEQ ID NO 59
<211> LENGTH: 18
<212> TYPE: PRT
<213> ORGANISM: Artificial Sequence
<220> FEATURE:
<223> OTHER INFORMATION: synthetic construct

<400> SEQUENCE: 59

Arg Lys Lys Arg Arg Gln Arg Arg Arg Pro Arg Pro Asp Asp Leu
1               5                   10                  15

Glu Ile

<210> SEQ ID NO 60
<211> LENGTH: 30
<212> TYPE: PRT
<213> ORGANISM: Artificial Sequence
<220> FEATURE:
<223> OTHER INFORMATION: synthetic construct

<400> SEQUENCE: 60

Thr Arg Ser Ser Arg Ala Gly Leu Gln Phe Pro Val Gly Arg Val His
1               5                   10                  15

Arg Leu Leu Arg Lys Arg Pro Arg Pro Asp Asp Leu Glu Ile
            20                  25                  30

<210> SEQ ID NO 61
<211> LENGTH: 35
<212> TYPE: PRT
<213> ORGANISM: Artificial Sequence
<220> FEATURE:
<223> OTHER INFORMATION: synthetic construct

<400> SEQUENCE: 61

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu Arg Pro Arg Pro Asp Asp
            20                  25                  30

Leu Glu Ile
        35

<210> SEQ ID NO 62
<211> LENGTH: 27
<212> TYPE: PRT

<213> ORGANISM: Artificial Sequence
<220> FEATURE:
<223> OTHER INFORMATION: synthetic construct

<400> SEQUENCE: 62

Lys Leu Ala Leu Lys Leu Ala Leu Lys Ala Leu Lys Ala Ala Leu Lys
1               5                   10                  15

Leu Ala Arg Pro Arg Pro Asp Asp Leu Glu Ile
            20                  25

<210> SEQ ID NO 63
<211> LENGTH: 25
<212> TYPE: PRT
<213> ORGANISM: Artificial Sequence
<220> FEATURE:
<223> OTHER INFORMATION: synthetic construct

<400> SEQUENCE: 63

Ala Ala Val Ala Leu Leu Pro Ala Val Leu Leu Ala Leu Leu Ala Pro
1               5                   10                  15

Arg Pro Arg Pro Asp Asp Leu Glu Ile
            20                  25

<210> SEQ ID NO 64
<211> LENGTH: 19
<212> TYPE: PRT
<213> ORGANISM: Artificial Sequence
<220> FEATURE:
<223> OTHER INFORMATION: synthetic construct

<400> SEQUENCE: 64

Val Pro Met Leu Lys Pro Met Leu Lys Glu Arg Pro Arg Pro Asp Asp
1               5                   10                  15

Leu Glu Ile

<210> SEQ ID NO 65
<211> LENGTH: 37
<212> TYPE: PRT
<213> ORGANISM: Artificial Sequence
<220> FEATURE:
<223> OTHER INFORMATION: synthetic construct

<400> SEQUENCE: 65

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Arg Pro Arg Pro
            20                  25                  30

Asp Asp Leu Glu Ile
        35

<210> SEQ ID NO 66
<211> LENGTH: 27
<212> TYPE: PRT
<213> ORGANISM: Artificial Sequence
<220> FEATURE:
<223> OTHER INFORMATION: synthetic construct

<400> SEQUENCE: 66

Leu Leu Ile Ile Leu Arg Arg Arg Ile Arg Lys Gln Ala His Ala His
1               5                   10                  15

Ser Lys Arg Pro Arg Pro Asp Asp Leu Glu Ile
            20                  25

<210> SEQ ID NO 67
<211> LENGTH: 30
<212> TYPE: PRT
<213> ORGANISM: Artificial Sequence
<220> FEATURE:
<223> OTHER INFORMATION: synthetic construct

<400> SEQUENCE: 67

Lys Glu Thr Trp Trp Glu Thr Trp Trp Thr Glu Trp Ser Gln Pro Lys
1               5                   10                  15

Lys Lys Arg Lys Val Arg Pro Arg Pro Asp Asp Leu Glu Ile
            20                  25                  30

<210> SEQ ID NO 68
<211> LENGTH: 27
<212> TYPE: PRT
<213> ORGANISM: Artificial Sequence
<220> FEATURE:
<223> OTHER INFORMATION: synthetic construct

<400> SEQUENCE: 68

Arg Gly Gly Arg Leu Ser Tyr Ser Arg Arg Arg Phe Ser Thr Ser Thr
1               5                   10                  15

Gly Arg Arg Pro Arg Pro Asp Asp Leu Glu Ile
            20                  25

<210> SEQ ID NO 69
<211> LENGTH: 24
<212> TYPE: PRT
<213> ORGANISM: Artificial Sequence
<220> FEATURE:
<223> OTHER INFORMATION: synthetic construct

<400> SEQUENCE: 69

Ser Asp Leu Trp Glu Met Met Met Val Ser Leu Ala Cys Gln Tyr Arg
1               5                   10                  15

Pro Arg Pro Asp Asp Leu Glu Ile
            20

<210> SEQ ID NO 70
<211> LENGTH: 21
<212> TYPE: PRT
<213> ORGANISM: Artificial Sequence
<220> FEATURE:
<223> OTHER INFORMATION: synthetic construct

<400> SEQUENCE: 70

Thr Ser Pro Leu Asn Ile His Asn Gly Gln Lys Leu Arg Pro Arg Pro
1               5                   10                  15

Asp Asp Leu Glu Ile
            20

<210> SEQ ID NO 71
<211> LENGTH: 120
<212> TYPE: PRT
<213> ORGANISM: Artificial Sequence
<220> FEATURE:
<223> OTHER INFORMATION: synthetic construct

<400> SEQUENCE: 71

Lys Gly Lys Ser Asp Pro Tyr His Ala Thr Ser Gly Ala Leu Ser Pro
1               5                   10                  15

Ala Lys Asp Cys Gly Ser Gln Lys Tyr Ala Tyr Phe Asn Gly Cys Ser
            20                  25                  30

Ser Pro Thr Ala Pro Leu Ser Pro Met Ser Pro Pro Gly Tyr Lys Leu
        35                  40                  45

Val Thr Gly Asp Arg Asn Asn Ser Ser Cys Arg Asn Tyr Asn Lys Gln
 50                  55                  60

Ala Ser Glu Gln Asn Trp Ala Asn Tyr Ser Ala Glu Gln Asn Arg Met
 65                  70                  75                  80

Gly Gln Ala Gly Ser Thr Ile Ser Asn Ser His Ala Gln Pro Phe Asp
                85                  90                  95

Phe Pro Asp Asn Gln Asn Ser Lys Lys Leu Ala Ala Gly His Glu
                100                 105                 110

Leu Gln Pro Leu Ala Ile Val Asp
        115                 120

<210> SEQ ID NO 72
<211> LENGTH: 120
<212> TYPE: PRT
<213> ORGANISM: Artificial Sequence
<220> FEATURE:
<223> OTHER INFORMATION: synthetic construct

<400> SEQUENCE: 72

Lys Thr Asp Pro Tyr Ser His Ser Gly Thr Met Ser Pro Ser Lys Asp
 1               5                  10                  15

Cys Gly Ser Pro Lys Tyr Ala Tyr Tyr Asn Gly Cys Ser Ser Pro Thr
                20                  25                  30

Ala Pro Leu Ser Pro Met Ser Pro Pro Gly Tyr Lys Leu Val Thr Gly
                35                  40                  45

Asp Arg Asn Asn Ser Ser Cys Arg Asn Tyr Asn Lys Gln Ala Ser Glu
 50                  55                  60

Gln Asn Trp Ala Asn Tyr Ser Ala Glu Gln Asn Arg Met Gly Gln Ala
 65                  70                  75                  80

Gly Ser Thr Ile Ser Asn Ser His Ala Gln Pro Phe Asp Phe Ala Asp
                85                  90                  95

Glu His Gln Asn Thr Lys Lys Leu Ala Ser Gly His Glu Leu Gln Pro
                100                 105                 110

Leu Thr Ile Val Asp Gln Arg Pro
        115                 120

<210> SEQ ID NO 73
<211> LENGTH: 120
<212> TYPE: PRT
<213> ORGANISM: Artificial Sequence
<220> FEATURE:
<223> OTHER INFORMATION: synthetic construct

<400> SEQUENCE: 73

Leu Gly Phe Gly Thr Ile Arg Asp Ser Leu Asn Ser Lys Arg Arg Glu
 1               5                  10                  15

Leu Glu Asp Pro Gly Ala Tyr Asn Tyr Pro Phe Thr Trp Asn Thr Pro
                20                  25                  30

Ser Ala Pro Pro Gly Tyr Asn Ile Ala Val Lys Pro Asp Gln Ile Gln
        35                  40                  45

Tyr Thr Glu Leu Ser Asn Ala Lys Ile Ala Tyr Lys Gln Asn Lys Ala
 50                  55                  60

Asn Thr Ala Gln Glu Gln Gln Tyr Gly Ser His Glu Glu Asn Leu Pro
 65                  70                  75                  80

Ala Asp Leu Glu Ala Leu Gln Arg Glu Ile Arg Met Ala Gln Glu Arg
                85                  90                  95

```
Leu Asp Leu Ala Val Gln Ala Tyr Ser His Gln Asn Asn Pro His Gly
                100                 105                 110

Pro Arg Glu Lys Lys Ala Lys Val
        115                 120

<210> SEQ ID NO 74
<211> LENGTH: 120
<212> TYPE: PRT
<213> ORGANISM: Artificial Sequence
<220> FEATURE:
<223> OTHER INFORMATION: synthetic construct

<400> SEQUENCE: 74

Gly Phe Gly Thr Ile Arg Asp Thr Leu Asn Asn Lys Arg Lys Glu Leu
1               5                   10                  15

Glu Asp Ser Gly Thr Tyr Asn Tyr Pro Phe Thr Trp Asn Thr Pro Ser
            20                  25                  30

Ala Pro Pro Gly Tyr Asn Ile Ala Val Lys Pro Asp Gln Met Gln Tyr
        35                  40                  45

Thr Glu Leu Ser Asn Ala Lys Met Ala Tyr Lys Gln Asn Lys Ala Asn
    50                  55                  60

Ile Ala Gln Glu Gln Gln Tyr Gly Ser Asn Glu Asn Ile Pro Ala
65                  70                  75                  80

Asp Leu Glu Asn Leu Gln Arg Glu Ile Lys Val Ala Gln Glu Arg Leu
                85                  90                  95

Asp Met Ala Ile Gln Ala Tyr Asn Asn Gln Asn Asn Pro Gly Ser Ser
                100                 105                 110

Ser Arg Glu Lys Lys Ser Lys Ala
        115                 120

<210> SEQ ID NO 75
<211> LENGTH: 120
<212> TYPE: PRT
<213> ORGANISM: Artificial Sequence
<220> FEATURE:
<223> OTHER INFORMATION: synthetic construct

<400> SEQUENCE: 75

Pro Tyr Leu Val Asp Cys Phe Val Ser Arg Pro Thr Glu Lys Thr Ile
1               5                   10                  15

Phe Ile Ile Phe Met Leu Val Val Gly Leu Ile Ser Leu Val Leu Asn
            20                  25                  30

Leu Leu Glu Leu Val His Leu Leu Cys Arg Cys Leu Ser Arg Gly Met
        35                  40                  45

Arg Ala Arg Gln Gly Gln Asp Ala Pro Pro Thr Gln Gly Thr Ser Ser
    50                  55                  60

Asp Pro Tyr Thr Asp Gln Val Phe Phe Tyr Leu Pro Val Gly Gln Gly
65                  70                  75                  80

Pro Ser Ser Pro Pro Cys Pro Thr Tyr Asn Gly Leu Ser Ser Glu
                85                  90                  95

Gln Asn Trp Ala Asn Leu Thr Thr Glu Glu Arg Leu Ala Ser Ser Arg
                100                 105                 110

Pro Pro Leu Phe Leu Asp Pro Pro
        115                 120

<210> SEQ ID NO 76
<211> LENGTH: 120
<212> TYPE: PRT
```

<213> ORGANISM: Artificial Sequence
<220> FEATURE:
<223> OTHER INFORMATION: synthetic construct

<400> SEQUENCE: 76

```
Cys Gly Ser Lys Glu His Gly Asn Arg Lys Met Arg Gly Arg Leu Leu
1               5                   10                  15
Leu Thr Tyr Met Ala Ser Ile Phe Phe Lys Ser Val Phe Glu Val Ala
            20                  25                  30
Phe Leu Leu Ile Gln Trp Tyr Leu Tyr Gly Phe Thr Leu Ser Ala Val
        35                  40                  45
Tyr Ile Cys Glu Gln Ser Pro Cys Pro His Arg Val Asp Cys Phe Leu
    50                  55                  60
Ser Arg Pro Thr Glu Lys Thr Ile Phe Ile Leu Phe Met Leu Val Val
65                  70                  75                  80
Ser Met Val Ser Phe Val Leu Asn Val Ile Glu Leu Phe Tyr Val Leu
                85                  90                  95
Phe Lys Ala Ile Lys Asn His Leu Gly Asn Glu Lys Glu Glu Val Tyr
            100                 105                 110
Cys Asn Pro Val Glu Leu Gln Lys
        115                 120
```

<210> SEQ ID NO 77
<211> LENGTH: 239
<212> TYPE: PRT
<213> ORGANISM: Artificial Sequence
<220> FEATURE:
<223> OTHER INFORMATION: synthetic construct

<400> SEQUENCE: 77

```
Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
            20                  25                  30
Glu Gly Glu Gly Asp Ala Thr Tyr Gly Lys Leu Thr Leu Lys Phe Ile
        35                  40                  45
Cys Thr Thr Gly Lys Leu Pro Val Pro Trp Pro Thr Leu Val Thr Thr
    50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
    130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
```

```
Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 78
<211> LENGTH: 60
<212> TYPE: DNA
<213> ORGANISM: Artificial Sequence
<220> FEATURE:
<223> OTHER INFORMATION: synthetic construct

<400> SEQUENCE: 78
ccctcctccc gggcctcctc ccgggcctcc tcccggcccc ggcccgacga cctggagatc    60

<210> SEQ ID NO 79
<211> LENGTH: 27
<212> TYPE: DNA
<213> ORGANISM: Artificial Sequence
<220> FEATURE:
<223> OTHER INFORMATION: synthetic construct

<400> SEQUENCE: 79
cggccccggc ccgacgacct ggagatc    27

<210> SEQ ID NO 80
<211> LENGTH: 27
<212> TYPE: DNA
<213> ORGANISM: Artificial Sequence
<220> FEATURE:
<223> OTHER INFORMATION: synthetic construct

<400> SEQUENCE: 80
cggccccggc ccgacgacct ggaggtg    27

<210> SEQ ID NO 81
<211> LENGTH: 27
<212> TYPE: DNA
<213> ORGANISM: Artificial Sequence
<220> FEATURE:
<223> OTHER INFORMATION: synthetic construct

<400> SEQUENCE: 81
cggccccggc ccgacgacgt gcccgtg    27

<210> SEQ ID NO 82
<211> LENGTH: 27
<212> TYPE: DNA
<213> ORGANISM: Artificial Sequence
<220> FEATURE:
<223> OTHER INFORMATION: synthetic construct

<400> SEQUENCE: 82
aaggcccggt ccgacgacct gtccgtg    27

<210> SEQ ID NO 83
<211> LENGTH: 48
<212> TYPE: DNA
<213> ORGANISM: Artificial Sequence
<220> FEATURE:
<223> OTHER INFORMATION: synthetic construct

<400> SEQUENCE: 83
cggcagccca agatctggtt ccccaaccgg cggaagccct ggaagaag    48

-continued

<210> SEQ ID NO 84
<211> LENGTH: 108
<212> TYPE: DNA
<213> ORGANISM: Artificial Sequence
<220> FEATURE:
<223> OTHER INFORMATION: synthetic construct

<400> SEQUENCE: 84
cggcagccca agatctggtt ccccaaccgg cggaagccct ggaagaagcc ctcctcccgg      60
gcctcctccc gggcctcctc ccggccccgg cccgacgacc tggagatc                 108

<210> SEQ ID NO 85
<211> LENGTH: 75
<212> TYPE: DNA
<213> ORGANISM: Artificial Sequence
<220> FEATURE:
<223> OTHER INFORMATION: synthetic construct

<400> SEQUENCE: 85
cggcagccca agatctggtt ccccaaccgg cggaagccct ggaagaagcg ccccggccc      60 gacgacctgg agatc                                                      75

<210> SEQ ID NO 86
<211> LENGTH: 75
<212> TYPE: DNA
<213> ORGANISM: Artificial Sequence
<220> FEATURE:
<223> OTHER INFORMATION: synthetic construct

<400> SEQUENCE: 86
cggcagccca agatctggtt ccccaaccgg cggaagccct ggaagaagcg ccccggccc      60 gacgacctgg aggtg                                                      75

<210> SEQ ID NO 87
<211> LENGTH: 75
<212> TYPE: DNA
<213> ORGANISM: Artificial Sequence
<220> FEATURE:
<223> OTHER INFORMATION: synthetic construct

<400> SEQUENCE: 87
cggcagccca agatctggtt ccccaaccgg cggaagccct ggaagaagcg ccccggccc      60 gacgacgtgc ccgtg                                                      75

<210> SEQ ID NO 88
<211> LENGTH: 75
<212> TYPE: DNA
<213> ORGANISM: Artificial Sequence
<220> FEATURE:
<223> OTHER INFORMATION: synthetic construct

<400> SEQUENCE: 88
cggcagccca agatctggtt ccccaaccgg cggaagccct ggaagaagaa ggcccggtcc      60
gacgacctgt ccgtg                                                      75

<210> SEQ ID NO 89
<211> LENGTH: 20
<212> TYPE: PRT
<213> ORGANISM: Artificial Sequence
<220> FEATURE:
<223> OTHER INFORMATION: synthetic construct

<400> SEQUENCE: 89

```
Pro Cys Ser Arg Ala Ser Ser Arg Met Ser Ser Arg Ala Arg Pro Asp
1               5                   10                  15

Asp Leu Asp Val
            20

<210> SEQ ID NO 90
<211> LENGTH: 19
<212> TYPE: PRT
<213> ORGANISM: Artificial Sequence
<220> FEATURE:
<223> OTHER INFORMATION: synthetic construct

<400> SEQUENCE: 90

Pro Arg Val Ser Val Pro Asn Phe Gly Arg Thr Gln Ser Ser Asp Ser
1               5                   10                  15

Ala Tyr Val

<210> SEQ ID NO 91
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Xaa is biotinylated L-2-aminohexanoic acid

<400> SEQUENCE: 91

Xaa Arg Gln Pro Lys Ile Trp Phe Pro Asn Arg Arg Lys Pro Trp Lys
1               5                   10                  15

Lys Arg Pro Arg Pro Asp Asp Leu Glu Ile
            20                  25
```

PEPTIDE FORMULATIONS AND OPHTHALMIC USES THEREOF

CROSS REFERENCE TO RELATED APPLICATIONS

This reference claims the benefit of priority of U.S. Provisional Application No. 63/104,086, filed on Oct. 22, 2020, the entire contents of which are hereby incorporated by reference.

STATEMENT REGARDING FEDERALLY SPONSORED RESEARCH

This invention was created in the performance of a Cooperative Research and Development Agreement with the National Institutes of Health, an Agency of the Department of Health and Human Services. The Government of the United States has certain rights in this invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: FIRS_012_01US SubSeqList.txt, date recorded: Feb. 18, 2022, file size 32,734 bytes).

BACKGROUND OF THE INVENTION

Corneal injuries and ocular trauma have the potential to instigate ocular morbidity, which can span in severity to include vision loss. Possible insults to the cornea are limitless, but significant efforts to address burn and blast injuries in combat soldiers along with the incidence of secondary corneal damage due to diseases, such as diabetes, exemplify the need for biotherapeutics that address the multifaceted and complex wound healing process of the eye. In order to maintain visual acuity, corneal injury treatment must promote rapid corneal reepithelization, mitigate injury progression/persistence, and, depending on the affected corneal cell types/tissue layers, also encourage regeneration of the other affected tissue layers. Significantly, if the corneal stroma is penetrated and damaged, the ocular treatment must allow for proper healing through the transformation of keratocytes to fibroblasts and myofibroblasts but preclude excessive actions by myofibroblasts that can cause corneal opacification and scarring. Importantly, inflammatory cell infiltrates also require calculated consideration as disproportionate inflammation can have detrimental effects. Suppressed immune actions can lead to infection, while excessive inflammation disrupts normal wound healing and regeneration. Therefore, an injury to the cornea, where distinct cellular layers and structural uniformity and composition of extracellular matrices are essential to proper corneal biomechanics and functionality, requires a biotherapeutic with specific biological effects on several different cell types present following tissue damage.

The current standard of care (SOC) for corneal injuries includes ocular irrigation, lubricants, artificial tears, antibiotics, bandage contact lenses, tarsorrhaphy, or construction of a conjunctival flap. These therapeutic approaches have two significant limitations. First, they do not address the fundamental biological and molecular processes in corneal wound healing, where therapeutic failure is associated with severe impairment or loss of vision. Second, as epitomized by corneal injury and trauma caused by explosive or incendiary devices in combat situations, these SOC treatments are either not possible or probable to occur in timely manner where medical facilities are limited and ocular wounds are treated secondarily.

In addition, there is a clear need for topical therapeutic formulations that have the characteristics necessary to provide safe and effective treatment of the sensitive tissues of the eye. In particular, the development of peptide containing formulations for ocular use presents unique challenges; the poor chemical and physical stability of peptides in solution limits formulation options. Therapeutics to be used for ophthalmic delivery must meet International Council on Harmonization (ICH) and United States Pharmacopeia (USP) guidelines governing formulation heterogeneity, stability, viscosity, and pH to ensure safety as well as effective delivery of the active pharmaceutical ingredient to the surface of the eye. Moreover, macromolecules such as proteins, antibodies, and small peptides exhibit poor bioavailability when delivered topically to the eye in traditional eye drop vehicles.

Thus, there is a significant need for eye drop biotherapeutics that expedite wound healing while mitigating the dysregulated biological processes that cause corneal opacity and vision loss. This disclosure addresses this and other needs.

BRIEF SUMMARY OF THE INVENTION

In an aspect, the present disclosure provides formulations comprising one or more peptides, wherein the formulations are suitable for topical administration to the eye. For example, the provided formulations are eye drop formulations. In an aspect, the present disclosure provides formulations for use in treating corneal injuries.

In embodiments, the present disclosure provides a formulation comprising an active peptide having a molecular weight of about 1.0 kDa to about 10.0 kDa and hydroxypropyl methylcellulose (HPMC), wherein the formulation is suitable for topical ocular delivery. In embodiments, the HPMC is present in the formulation at a concentration of about 0.01% (w/w) to about 2.0% (w/w), or at a concentration of about 0.1% (w/w) to about 0.19% (w/w). In embodiments, the HPMC is present in the formulation at a concentration of about 0.1% or about 0.2% or about 0.3% or about 0.5% or about 1.0% (w/w). In embodiments, the formulation further comprises sodium chloride (NaCl). In embodiments, the NaCl is present at a concentration from about 0.5% to about 2.0%, or about 0.7% to about 1.5%. In embodiments, the NaCl is present at a concentration from about 0.25% to about 0.9%. In embodiments, the NaCl is present at a concentration of about 0.9% (w/w).

In embodiments, the formulation further comprises a tonicity modifier. For example, in embodiments, the formulation further comprises dextrose, glycerin, mannitol, potassium chloride, or magnesium chloride.

In embodiments, the active peptide is present in the composition at a concentration of about 0.005% (w/w) to about 5% (w/w), or about 0.035% (w/w) to about 3.5% (w/w). In embodiments, the active peptide is present in the composition at a concentration of about 0.035% (w/w) to about 3.0% (w/w). In embodiments, the active peptide is present in the composition at a concentration of about 0.05% (w/w) to about 2.5% (w/w). In embodiments, the active peptide is present in the composition at a concentration of about 0.1% (w/w) to about 2.0% (w/w). In embodiments, the active peptide is present in the composition at a concentration of about 0.5% (w/w) to about 1.5% (w/w). In embodiments, the formulation has a viscosity between about 18 mPaS and about 28 mPaS. In embodiments, the formulation has a viscosity of about 18 mPaS, about 19 mPaS, about 20 mPaS, about 21 mPaS, about 22 mPaS, about 23 mPaS, about 24 mPaS, about 25 mPaS, about 26 mPaS, about 27 mPaS, or about 28 mPaS. In embodiments, the formulation has a pH of about 5 to about 8, or about 5 to about 7, or about 5, about 6, about 7, or about 8. In embodiments, the formulation has a pH of about 6.5. In embodiments, the formulation has a pH of between about 6.5 and about 7.5. In embodiments, the formulation has a pH of between about 6.5 and about 7.0. In embodiments, the formulation has an osmolality of about 200 to about 350 mOsm/kg, e.g., about 280 to about 350 mOsm/kg, e.g., about 288 mOsm/kg. In embodiments, the formulation has a density of about 0.5 g/mL to about 2.0 g/mL. In embodiments, the formulation has a density of about 0.5 g/mL, about 0.6 g/mL, about 0.7 g/mL, about 0.8 g/mL, about 0.9 g/mL, about 1.0 g/mL, about 1.1 g/mL, about 1.2 g/mL, about 1.3 g/mL, about 1.4 g/mL, about 1.5 g/mL, about 1.6 g/mL, about 1.7 g/mL, about 1.8 g/mL, about 1.9 g/mL, or about 2.0 g/mL. For example, in embodiments, the formulation has a density of about 0.99 g/mL.

In embodiments, the active agent in the formulations provided herein is an alpha connexin peptide, or an active fragment thereof. For example, in embodiments, the polypeptide comprises the carboxy terminal-most 4 to 30 contiguous amino acids of the alpha Connexin. In embodiments, the polypeptide consists of the carboxy terminal-most 4 to 30 contiguous amino acids of an alpha connexin. In embodiments, the alpha Connexin is Connexin 37, Connexin 40, Connexin 43, or Connexin 45. In embodiments, the polypeptide comprises an amino acid sequence selected from the group consisting of SEQ ID NO: 1, SEQ ID NO: 2, SEQ ID NO: 3, SEQ ID NO: 4, and SEQ ID NO: 5. In embodiments, the polypeptide comprises the amino sequence of SEQ ID NO: 2. In embodiments, the polypeptide further comprises a cellular internalization sequence. In embodiments, the cellular internalization sequence comprises an amino acid sequence of a protein selected from a group consisting of Antennapedia, TAT, HIV-Tat, Penetratin, Antp-3A (Antp mutant), Buforin II, Transportan, MAP (model amphipathic peptide), K-FGF, Ku70, Prion, pVEC, Pep-1, SynB 1, Pep-7, HN-1, BGSC (Bis-Guanidinium-Spermidine-Cholesterol) and BGTC (Bis-Guanidinium-Tren-Cholesterol). In embodiments, the cellular internalization sequence is Antennapedia, and wherein the sequence comprises the amino acid sequence of SEQ ID NO: 7. In embodiments, the polypeptide comprises an amino acid sequence selected from the group consisting of SEQ ID NO: 8, SEQ ID NO: 9, SEQ ID NO: 10, SEQ ID NO: 11, and SEQ ID NO: 12. In certain embodiments, the polypeptide comprises the amino acid sequence of SEQ ID NO: 9.

In embodiments, the formulations provided herein are suitable for topical ocular administration. In embodiments, the administration is via eye drop administration.

In embodiments, the present disclosure provides methods of treating or preventing an ocular injury in a subject in need thereof, comprising topically administering a formulation provided herein. In embodiments, the present disclosure provides formulations and methods for accelerating corneal reepithelialization following an ocular injury in a subject, the method comprising topically administering a formulation provided herein to the eye of the subject. In embodiments, the formulation is administered to the eye immediately after the event that caused the ocular injury. In embodiments, the polypeptide is administered to the subject within about 1 hour, within about 2 hours, within about 5 hours, or within about 12 hours of the event that caused the ocular injury. In embodiments, the polypeptide is administered to the subject at least about 2 hours following the event that caused the ocular injury. In embodiments, the polypeptide is administered to the eye of the subject twice per day, or about every 8 hours, or about every 12 hours, until ocular healing is observed. In embodiments, the ocular injury is a corneal injury. In embodiments, the ocular injury is a retinal injury. In embodiments, the ocular injury is caused by a burn, explosion, or laceration. In embodiments, the ocular injury is a chemical or thermal burn injury. In embodiments, the ocular injury is caused by contact of the eye with a vesicating agent, such as mustard gas or the like. In embodiments, the ocular injury is caused by a chronic disease. In embodiments, the chronic disease is diabetes or diabetic keratopathy. In embodiments, the chronic disease is retinal disease. In embodiments, the subject has dry eye disease. In embodiments, the subject has a persistent corneal epithelial defect, such as may be caused by dry eye disease. In embodiments, the injury is secondary to an ocular surgery, a chemical or thermal burn injury, or a corneal laceration injury.

In embodiments, the present disclosure provides formulations for use in treating or preventing an ocular injury in a subject in need thereof, and/or formulations for use in accelerating corneal reepithelialization following an ocular injury in a subject.

BRIEF DESCRIPTION OF THE DRAWINGS

FIG. 4A shows corneal thickness and FIG. 4B provides quantification of the same in the indicated groups. n=3 per treatment group.

FIG. 5A shows H&E staining and FIG. 5B shows inflammatory cell infiltration was significantly reduced in aCT1 treated groups. FIG. 5C shows pro-inflammatory enzyme COX2 staining and FIG. 5D provides quantification of COX2 in corneal tissues. (n=3 per treatment group; one-way ANOVA, p<0.01; *p<0.001; SD).

FIG. 6A provides H&E staining and FIG. 6B shows the corneal fibroblasts cell counts in treated corneas in the indicated groups. FIG. 6C shows IHC staining for matrix metalloproteinase-9 (MMP-9), which leads to degradation of the corneal stroma. FIG. 5D provides quantification of MMP-9 positivity in the corneal stroma. n=3 per treatment group.

FIG. 7A shows blood vessels in the cornea in each group by H&E staining and FIG. 7B provides a quantification of blood vessel count in each group. Vascular endothelial growth factor (VEGF) is a signaling protein that stimulates neovascularization. FIG. 7C shows staining for VEGF and FIG. 7D provides quantification of the VEGF positivity score. n=3 per treatment group.

DETAILED DESCRIPTION

Figure 1:
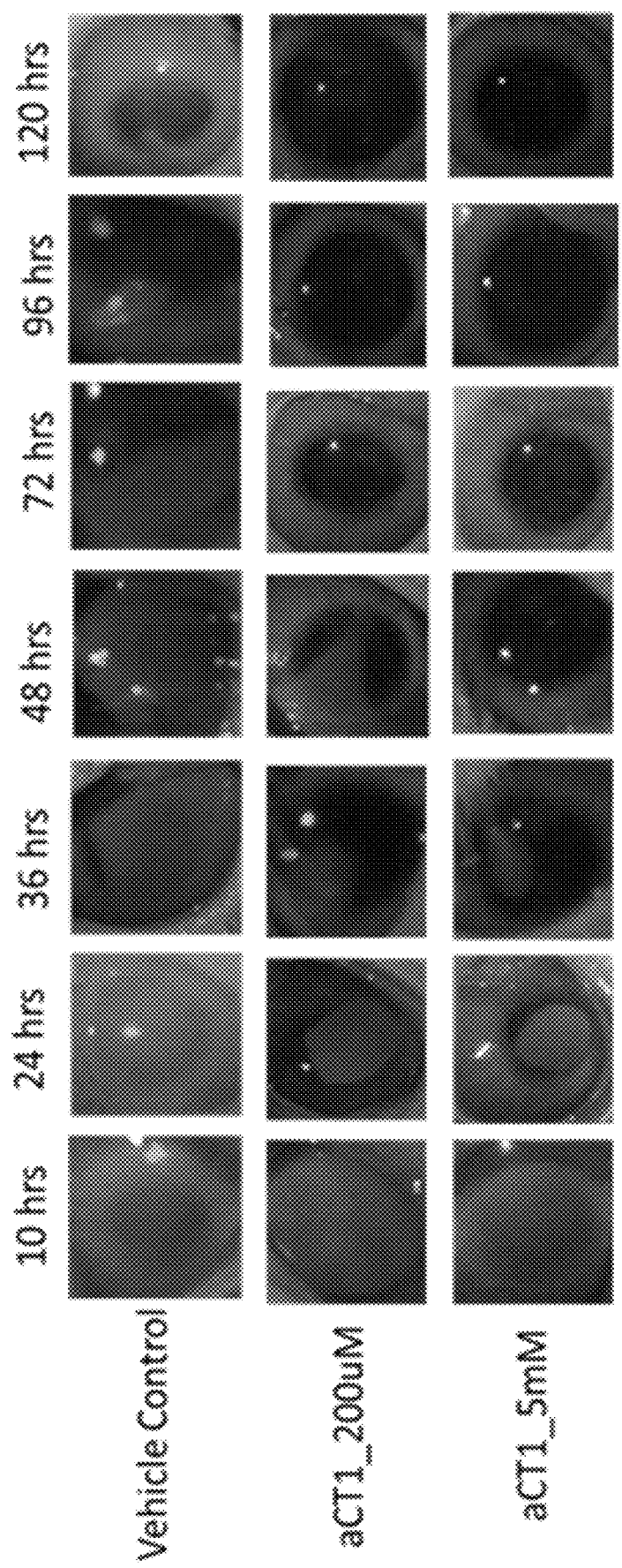
FIG. 1 shows corneal staining using 1% fluorescein at 10, 24, 36, 48, 72, 96, or 120 hrs following corneal chemical burn, and with eye drop administration of aCT1 (200 μM or 5 mM) or vehicle control twice daily for two days following chemical injury.

Provided herein are formulations for topical delivery of peptide compositions to the eye, and methods for treating or preventing eye disorders and conditions, such as corneal injuries.

Therapeutics to be used for ophthalmic delivery must meet ICH and USP guidelines governing formulation heterogeneity, stability, viscosity, and pH to ensure safety as well as effective delivery of the active pharmaceutical ingredient to the relevant tissues of the eye. The development of peptide containing formulations for ocular use presents unique challenges including the poor chemical and physical stability of peptides in solution, particularly in the type of solution that provides sufficient stability and viscosity for topical administration to the eye. Failure to develop peptide containing formulations that exhibit sufficient bioavailability for treatment of ocular disorders is a likely explanation for the lack of peptide based ocular therapeutics that have obtained FDA approval. Few peptide containing ocular formulations have been FDA approved. For those that are approved, the route of administration for these peptide containing formulations is intravitreal injection (Mandal et al. 2018), instead of the safer and less invasive topical route of administration.

A viscoelastic polymer such as hydroxypropyl methylcellulose (HPMC) has not been used in combination with a peptide in a formulation appropriate for eye drop delivery. A formulation with appropriate viscosity, surface tension, and other physical properties is necessary for an eye drop to achieve sufficient contact time with the ocular surface necessary to ensure peptide delivery. Small peptides are expected to exhibit poor solubility in conventional excipients employed to modify eye drop viscosity such as HPMC, carboxymethylcellulose (CMC), hydroxyethyl cellulose (HEC), and PF-127. Peptide aggregation in combination with these ingredients results in precipitate formation that makes the formulation unsuitable for ocular delivery. Thus, conventional teaching in the art is away from a formulation which utilizes a viscoelastic polymer such as HPMC in combination with a small peptide active pharmaceutical ingredient. Instead, current formulations for delivery of small peptide therapeutics involve admixture of non-reducing sugars, amino acids, and surfactants with the peptide or other macromolecules to achieve formulations suitable for ocular delivery (Giannos et al. 2018, Kamerzell et al. 2011).

The present inventors unexpectedly discovered that a combination of a viscoelastic polymer with a small peptide active ingredient resulted in a formulation that maintains peptide solubility and with a kinematic viscosity appropriate for topical delivery of the peptide to the ocular surface. The formulation surprisingly achieves a stable solution state of the peptide in a formulation for eye drop delivery. Peptide stability in solution is an important performance characteristic differentiating the present invention from conventional peptide delivery systems. Due to poor solubility, peptides are known to precipitate out in conventional eye drop delivery systems. It is well known that solutions with high viscosity cannot be filter sterilized; conventional formulations for ocular delivery of macromolecules have used aqueous excipients that do not include viscoelastic polymers to achieve a solution with low viscosity that can be sterilized by passage through a sterile filter. Thus, there are no examples of HPMC admixed with therapeutic peptides to achieve a formulation suitable for topical delivery to the eye.

However, the present inventors surprisingly achieved a stable formulation comprising aCT1 peptide and HPMC, that was suitable for topical delivery to the eye and effective in treatment of ocular disorders. This formulation was unpredictably superior to formulations comprising CMC, HEC, or pluronic gel (PF-127) instead of HPMC. Unexpectedly, the use of the viscoelastic polymer HPMC with the peptide yielded a formulation having a viscosity sufficient to enable contact time necessary for peptide delivery to the ocular surface, yet that can be sterilized through passage of the solution through a 0.22 µM PVDF or PES membrane filter. Formulation sterility is necessary for delivery of therapeutic peptides to sensitive tissues such as the eye. Passage of formulations through a 0.22 µM PVDF or PES membrane filter produces a formulation with sterility suitable for the delivery of medication to sensitive ocular tissues.

In embodiments, the formulation further comprises sodium chloride (NaCl), potassium chloride (KCl), sodium iodide (NaI), magnesium chloride (MgCl2), potassium fluoride (KF), calcium chloride (CaCl2), sodium tetrafluoroborate (NaBF4), and/or sodium bromide (NaBr). In embodiments, the formulation comprises NaCl. In embodiments, the NaCl surprisingly provides greater stability relative to a formulation that does not comprise NaCl. In embodiments, the NaCl is present at a concentration from about 0.5% to about 2.0%, or about 0.7% to about 1.5%. In embodiments, the NaCl is present at a concentration from about 0.25% to about 0.9%. In embodiments, the NaCl is present at a concentration of about 0.9% (w/w).

In embodiments, the formulations provided herein exhibit stability over time at a range of temperatures. For example, the formulations provide peptide stability for at least 1 week, at least 2 weeks, at least 3 weeks, at least 4 weeks, at least 5 weeks, at least 6 weeks, at least two months, at least 3 months, at least 4 months, at least 5 months, at least 6 months, at least 8 months, at least 12 months, at least 18 months, at least 2 years, at least 3 years, or at least 6 years. In embodiments, the formulations provide peptide stability at about −20°, about 5° C., about 25° C., and any temperature therebetween. In certain embodiments, the formulations provide peptide stability at about −20° for at least 6 months, at least 8 months, at least 12 months, at least 18 months, at least 2 years, at least 3 years, at least 4 years, at least 5 years, or at least 6 years. In embodiments, the formulations provided herein comprise a peptide (e.g., an alpha connexin peptide), wherein the peptide remains at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, or at least about 95% stable over at least about 1 month. In embodiments, the formulations provided herein comprise a peptide (e.g., an alpha connexin peptide), wherein the peptide remains at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, or at least about 95% stable over at least about 3 months. In embodiments, the formulations provided herein comprise a peptide (e.g., an alpha connexin peptide), wherein the peptide remains at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, or at least about 95% stable over at least about 1 year, at least about 2 years, at least about 3 years, at least about 4 years, at least about 5 years, or at least about 6 years. Such stability is achieved at about −20°, about 5° C., about 25° C., and any temperature therebetween when the formulations provided herein are utilized.

In embodiments, the formulations provided herein exhibit no impurities or negligible impurities or an acceptable level of impurities over time at a range of storage temperatures. For example, the formulations exhibit no impurities or negligible impurities or an acceptable level of impurities for at least 1 week, at least 2 weeks, at least 3 weeks, at least 4 weeks, at least 5 weeks, at least 6 weeks, at least two months, at least 3 months, at least 4 months, at least 5 months, at least 6 months, at least 1 year, at least 2 years, at least 3 years, at least 4 years, at least 5 years, or at least 6 years. In embodiments, the formulations exhibit no impurities or negligible impurities or an acceptable level of impurities at about −20°, about 5° C., about 25° C., and any temperature therebetween. In embodiments, negligible levels of impurities in the formulation may be less than 0.1%. In embodiments, acceptable levels of impurities in the formulation may be less than about 5%, less than about 4%, less than about 3%, less than about 2%, less than about 1%, less than about 0.5%.

In embodiments, the formulations provided herein are readily filterable (e.g., filterable through a 0.2 μm PES filter). In embodiments, the formulations provided herein are more filterable compared to formulations previously used for ocular administration of peptides. In embodiments, the formulations provided herein comprising HPLC, a peptide (e.g., an alpha connexin peptide), NaCl, and does not require an additional vehicle, buffer, or excipient, to have formulation properties (e.g., viscosity, osmolality, density, pH, filterability) as well as purity and stability profiles suitable for ocular delivery.

In embodiments, the present disclosure provides an eye drop carrier containing a therapeutic peptide (e.g., aCT1 peptide) that is non-irritating, stable, and of appropriate characteristics for topical use in the eye. Thus, in embodiments, the present disclosure provides therapeutic eye drop compositions comprising alpha connexin polypeptides for the treatment of ocular injury or disease. In embodiments, the eye drop formulation further comprises HPMC. In embodiments, the formulation further comprises a buffer and/or excipient which stabilizes the alpha connexin polypeptide during storage. In embodiments, the alpha connexin polypeptide comprises a carboxyl terminal amino acid sequence of alpha connexin. The alpha connexin polypeptides of the present invention may comprise, consist, or include the carboxy-terminal most 4 to 30 contiguous amino acids of an alpha connexin protein or conservative variant thereof. In embodiments, the said at least one alpha connexin polypeptide is linked at its amino terminus to a cellular internalization transporter.

In embodiments, the present disclosure provides a formulation of a stable eye drop carrier that contains aCT1 for therapeutic application in ophthalmic indications, and methods for making the same. In embodiments, the ophthalmic indications include wound healing, inflammatory and immune modulation, tissue regeneration, biomechanical restoration, or treatment of other physiological conditions affecting any part of the cornea or other ocular tissue. The formulations provided herein may be administered to treat acute and chronic injuries and wounds, including military or civilian chemical injuries or corneal lacerations, surgery-related conditions, and acute and chronic manifestations of any primary ocular disorder or other condition causing a secondary ocular condition manifesting or necessitating medical attention. The formulations possess physicochemical, biochemical, and rheological properties that enable its ability to provide a therapeutic and effective amount of aCT1 peptide when applied to injuries, wounds, and conditions affecting proper eye function.

In embodiments, one or more buffering agents in any form added to sterile water may be used to maintain a physiologically relevant pH or to maintain a pH where the addition of pH modulators will result in a physiological-relevant pH. In some embodiments, one or more pH modulators such as sodium borate, citric acid, sodium nitrate, histidine, hydrochloric acid or sodium hydroxide may be added to adjust within the desire therapeutic range of pH 5 to 8. Preferably, buffering agents are non-irritating, non-staining, and non-immunogenic. In embodiments, a preferred buffer is histidine. In embodiments, the histidine is present at a concentration of about 20 mM to about 80 mM. In embodiments, the histidine is present at a concentration of about 40 mM.

In embodiments, the formulation further comprises a tonicity modifier. For example, in embodiments, the formulation further comprises dextrose, glycerin, mannitol, potassium chloride, or magnesium chloride. In embodiments, the formulation further comprises an antioxidant, such as methionine.

In embodiments, the formulations provided herein do not include a buffering agent. In embodiments, additional excipients are excluded from the formulation, such that the formulation does not comprise an excipient. In embodiments, the formulation comprises the active agent peptide, HPMC, and no added excipients. In embodiments, the formulations provided herein do not include any added sugars, amino acids, and/or surfactants. In embodiments, the formulation comprises, consists essentially of, or consists of the active agent (e.g., a connexin peptide), HPMC, NaCl, and water. In embodiments, the HPMC is present in the formulation at a concentration of about 0.2% w/w to about 1.0% w/w. In embodiments, the HPMC is present in the formulation at a concentration of about 0.5% w/w. In embodiments, the HPMC is present in the formulation at a concentration of about 1.0% w/w.

In embodiments, one or more polymers such as HPMC is included in the formulation to stabilize the isolated polypeptide. Preferably, the formulation comprises a stabilizer that is non-irritating, non-staining, and non-immunogenic. The addition of stabilizers enable long-term (i.e., for 3 months, for 6 months, for 9 months, for 12 months, for 18 months, or for 24 months) storage of the drug product under a variety of temperature conditions (e.g., at about 5° C., at about 10° C., at about 15° C., at about 20° C., at about 25° C., at about 30° C., at about 35° C., or at about 40° C.) and under a range of relative humidities (e.g., at about 0% relative humidity, at about 10% relative humidity, at about 20% relative humidity, at about 30% relative humidity, at about 40% relative humidity, at about 50% relative humidity, at about 60% relative humidity, at about 70% relative humidity, at about 80% relative humidity, at about 90% relative humidity, or at about 100% relative humidity). In embodiments, the present invention may also include a preservative to further maintain the described long-term storage under the stated variety of temperatures and relative humidities.

Exemplary formulations are provided below in Table 1.

| Form No | peptide | pH | His (mM) | NaCl (mM) | MgCl2 (mM) | mannitol (mM) | Met (mM) | HPMC (%) |
|---|---|---|---|---|---|---|---|---|
| 1 | 20 | 6.5 | 30 | 130 | 0 | 0 | 0 | 0.19 |
| 2 | 20 | 6.0 | 20 | 65 | 50 | 0 | 10 | 0.15 |
| 3 | 20 | 5.5 | 10 | 65 | 0 | 150 | 0 | 0.11 |
| 4 | 20 | 6.0 | 40 | 100 | 25 | 0 | 0 | 0 |
| 5 | 10 | 6.5 | 40 | 65 | 50 | 0 | 5 | 0.19 |
| 6 | 10 | 6.0 | 30 | 130 | 0 | 0 | 0 | 0.15 |
| 7 | 10 | 6.0 | 20 | 100 | 25 | 0 | 0 | 0.11 |
| 8 | 10 | 7.0 | 10 | 65 | 0 | 150 | 20 | 0 |
| 9 | 20 | 7.0 | 30 | 130 | 0 | 0 | 0 | 0.19 |
| 10 | 20 | 6.5 | 20 | 65 | 0 | 150 | 0 | 0.15 |
| 11 | 20 | 7.0 | 20 | 0 | 0 | 270 | 10 | 0.11 |
| 12 | 20 | 6.0 | 20 | 130 | 0 | 0 | 0 | 0 |
| 13 | 5 | 5.5 | 20 | 0 | 0 | 270 | 0 | 0.15 |
| 14 | 5 | 6.0 | 10 | 130 | 0 | 0 | 10 | 0 |
| 15 | 20 | 6.6 | 0 | 150 | 0 | 0 | 0 | 0.5 |
| 16 | 20 | 5.0 | 0 | 150 | 0 | 0 | 0 | 0.5 |

In embodiments, the formulations provided herein may be contained in plastic eye dropper or glass vial containing a single dose or multiple doses for therapeutic administration to a subject in need thereof a topical ophthalmic formulation comprising of at least one aCT polypeptide. In embodiments, the formulation may be contained in a glass container, and may be more stable in glass containers compared to containers made of other materials (e.g., plastic). In embodiments, the formulation may be contained in a plastic container, e.g., a plastic eye dropper. In embodiments, the topical ophthalmic formulation comprises HPMC. In embodiments, the formulations provided herein are in a sterile, ready-to-use eye drop formulation in an administration-appropriate and -designed eye dropper bottle or vial.

In embodiments, the present disclosure provides methods for treating and preventing corneal injuries and ocular trauma. In embodiments, the methods include topical administration to the eye of a formulation provided herein comprising an alpha connexin polypeptide. In embodiments, the injury or trauma is a closed globe ocular injury or wound where damage to the cornea has occurred. The cause of the corneal injury or wound is not limited to and may include blast injuries, chemical and thermal burns, and other insults or conditions causing acute or chronic injury, as either a primary and secondary manifestation of a disorder or disease. In embodiments, the cause of the corneal injury is exposure to a vesicant, or blister agent, such as nitrogen mustard or sulfur mustard (e.g., mustard gas). In embodiments, the disorder or disease is diabetes. In embodiments, the disorder or disease is diabetic keratopathy. In embodiments, the chronic disease is retinal disease. In embodiments, present disclosure provides methods for treating and preventing retinal diseases. For example, in embodiments, the retinal disease is selected from macular degeneration (e.g., age-related macular degeneration (AMD), neovascular age-related macular degeneration (nAMD)), retinitis pigmentosa (RP), retinal detachment, diabetic retinopathy, macular edema, diabetic macular edema (DME), and macular edema occurring after retinal vein occlusion (RVO). In embodiments, the disease or disorder involves corneal defects that occur in a subject when treatment for an ocular disease or disorder (e.g., a retinal disorder) involves vitrectomy and/or one or more intravitreal injections.

In embodiments, the methods provided herein includes treatment and/or prevention of any diseases or disorders leading to corneal scarring or excessive and dysregulated inflammation or an immune response. In embodiments, the subject is a human subject that has a persistent corneal epithelial defect (PED or PCED), which results from the failure of rapid reepithelialization and closure after corneal injury (e.g., within about 2 weeks), even with standard of care supportive treatment. PEDs can result in serious complications including infection and vision loss. In embodiments, the PED is caused by dry eye disease. Accordingly, in embodiments, the formulations and methods provided herein treat a subject suffering from PEDs or otherwise suffering from corneal injury by enhancing the rate of reepithelization following corneal injury. In embodiments, administration of the provided formulations enhances the rate of reepithelialization by about 10%, about 25%, about 50%, about 75%, about 100%, or more. In embodiments, the administration of the provided formulations enhances the rate of reepithelialization compared to the rate of reepithelialization in a control wherein standard of care or no treatment is administered to the eye of the subject. The rate of reepithelialization may be enhanced such that corneal healing occurs within about 2, about 3, about 4, about 5, about 6, about 7, about 8, about 9, about 10, about 11, about 12, about 13, or about 14 days after injury. The formulations and methods provided herein are not limited to exclusive treatment alone and may be used in conjunction with other standard of care treatment(s).

The polypeptides useful in the formulations and methods provided herein may be any polypeptide with properties such as wound healing properties, anti-inflammatory properties, properties relating to protection or regeneration of the corneal stroma, and/or anti-neovascular properties. In embodiments, the polypeptides can be any suitable polypeptide having a molecular weight of about 1.0 kDa to about 10.0 kDa. In embodiments, the polypeptide can be any suitable polypeptide having a molecular weight of about 1.0 kDa, about 2.0 kDa, about 3.0 kDa, about 4.0 kDa, about 5.0 kDa, about 6.0 kDa, about 7.0 kDa, about 8.0 kDa, about 9.0 kDa, or about 10.0 kDa.

In embodiments, the polypeptides can be any polypeptide comprising the carboxy-terminal most amino acids of an alpha Connexin, wherein the polypeptide does not comprise the full-length alpha Connexin protein. Thus, in embodiments, the provided polypeptide does not comprise the cytoplasmic N-terminal domain of the alpha Connexin. In embodiments, the provided polypeptide does not comprise the two extracellular domains of the alpha Connexin. In embodiments, the provided polypeptide does not comprise the four transmembrane domains of the alpha Connexin. In embodiments, the provided polypeptide does not comprise the cytoplasmic loop domain of the alpha Connexin. In embodiments, the provided polypeptide does not comprise that part of the sequence of the cytoplasmic carboxyl terminal domain of the alpha Connexin proximal to the fourth transmembrane domain. There is a conserved proline or glycine residue in alpha Connexins consistently positioned some 17 to 30 amino acids from the carboxyl terminal-most amino acid For example, for human Cx43 a proline residue at amino acid 363 is positioned 19 amino acids back from the carboxyl terminal most isoleucine. In another example, for chick Cx43 a proline residue at amino acid 362 is positioned 18 amino acids back from the carboxyl terminal-most isoleucine. In another example, for human Cx45 a glycine residue at amino acid 377 is positioned 19 amino acids back from the carboxyl terminal most isoleucine. In another example for rat Cx33, a proline residue at amino acid 258 is positioned 28 amino acids back from the carboxyl terminal most methionine. Thus, in embodiments, the provided polypeptide does not comprise amino acids proximal to said conserved proline or glycine residue of the alpha Connexin. Thus, the provided polypeptide can comprise the c-terminal-most 4 to 30 amino acids of the alpha Connexin, including the c-terminal most 4, 5, 6, 7, 8, 9, 10, 11, 12, 13, 14, 15, 16, 17, 18, 19, 20, 21, 22, 23, 24, 25, 26, 27, 28, 29, 30 amino acids of the alpha Connexin. Exemplary alpha Connexin polypeptides are disclosed in U.S. Pat. Nos. 7,786,074; 7,888,319; 8,357,668; 8,809,257; 8,916,515; 8,859,733; 8,846,605; 9,161,984; 9,394,351; 9,408,381; 9,844,214; 9,855,313; 10,398,140; and 10,398,757, and/or International Patent Application No. PCT/US2018/000035, the entire contents of each of which are hereby incorporated by reference.

Connexins are the sub-unit protein of the gap junction channel, which is responsible for intercellular communication (Goodenough and Paul, 2003). Based on patterns of conservation of nucleotide sequence, the genes encoding Connexin proteins are divided into two families termed the alpha and beta Connexin genes. The carboxy-terminal-most amino acid sequences of alpha Connexins are characterized by multiple distinctive and conserved features. This conservation of organization is consistent with the ability of aCT peptides to form distinctive 3D structures, interact with multiple partnering proteins, mediate interactions with lipids and membranes, interact with nucleic acids including DNA, transit and/or block membrane channels and provide consensus motifs for proteolytic cleavage, protein cross-linking, ADP-ribosylation, glycosylation and phosphorylation. Thus, the provided polypeptide interacts with a domain of a protein that normally mediates the binding of said protein to the carboxy-terminus of an alpha Connexin. For example, nephroblastoma overexpressed protein (NOV) interacts with a Cx43 c-terminal domain (Fu et al., J Biol. Chem. 2004 279(35):36943-50). It is considered that this and other proteins interact with the carboxy-terminus of alpha Connexins and further interact with other proteins forming a macromolecular complex. Thus, the provided polypeptide can inhibit the operation of a molecular machine, such as, for example, one involved in regulating the aggregation of Cx43 gap junction channels.

The polypeptides provided herein comprise a carboxy-terminal amino acid sequence of an alpha Connexin, or a conservative variant thereof. In embodiments, the polypeptide comprises or consists of the amino acid sequence RPRPDDLEI (SEQ ID NO: 2). In embodiments, the polypeptide is aCT1, as described herein. The term "aCT1" is used interchangeably herein with "aCT1," "aCT", "aCT-1", "ACT," and "ACT-1". aCT1 is a 25 aa peptide having a molecular weight of 3597.33 Da that has a compact 2-domain design based on linkage of an Antennapedia cell internalization domain (1-16aa; RQPKIWFPNRRKPWKK; SEQ ID NO: 7) to the C-terminal PDZ binding domain of the transmembrane gap junction protein Cx43 (17-25aa; RPRPDDLEI; SEQ ID NO:2). Accordingly, the full aCT1 sequence is RQPKIWFPNRRKPWKK RPRPDDLEI (SEQ ID NO: 9). aCT1 and related peptides increase the size and stability of gap junctions by modulating the molecular interaction between Cx43 and its C-terminal binding partners, including the tight junction protein zonula occludens-1 (ZO-1). This leads to phosphorylation of the serine 368 (S368) amino acid on Cx43 and favors a transition of cell-surface Cx43 from hemichannels to gap junction intercellular channels. Phosphorylation of S368 prevents the binding of ZO-1 to the C-terminus of Cx43 long after aCT1 has degraded, permitting therapeutic longevity. Concomitantly, aCT1 stabilizes ZO-1 at the cell membrane, preventing junctional degradation in response to injury and preserving barrier function of epithelial cells. The result is stabilization of gap junctions (intercellular communication) as well as tight junctions (intercellular junctions) leading to a variety of beneficial effects including increased cellular communication, dampened inflammatory responses, and reduction in the infiltration and proliferation of profibrotic cells. Collectively, the molecular and cellular events facilitated by aCT1 preserves tissue integrity, reduces injury spread, dampens pathological inflammation, and accelerates healing and tissue regeneration In embodiments, the compositions and methods provided herein are related to preventing, treating, and/or mitigating the progression of corneal injuries. In embodiments, the compositions and methods provided herein are related to preventing, treating, and/or mitigating the progression of corneal injuries. In embodiments, the formulations provided herein are for use in preventing, treating, and/or mitigating the progression of corneal injuries. In embodiments, provided herein are uses of aCT1 in the manufacture of a medicament for preventing or treating corneal injuries.

The aCT sequence of the provided polypeptide can be from any alpha Connexin. Thus, the alpha Connexin component of the provided polypeptide can be from a human, murine, bovine, monotrene, marsupial, primate, rodent, cetacean, mammalian, avian, reptilian, amphibian, piscine, chordate, protochordate or other alpha Connexin. Thus, the provided polypeptide can comprise an ACT of a Connexin selected from the group consisting of mouse Connexin 47, human Connexin 47, Human Connexin 46.6, Cow Connexin 46.6, Mouse Connexin 30.2, Rat Connexin 30.2, Human Connexin 31.9, Dog Connexin 31.9, Sheep Connexin 44, Cow Connexin 44, Rat Connexin 33, Mouse Connexin 33, Human Connexin 36, mouse Connexin 36, rat Connexin 36, dog Connexin 36, chick Connexin 36, zebrafish Connexin 36, morone Connexin 35, morone Connexin 35, Cynops Connexin 35, Tetraodon Connexin 36, human Connexin 37, chimp Connexin 37, dog Connexin 37, Cricetulus Connexin 37, Mouse Connexin 37, Mesocricetus Connexin 37, Rat Connexin 37, mouse Connexin 39, rat Connexin 39, human Connexin 40.1, Xenopus Connexin 38, Zebrafish Connexin 39.9, Human Connexin 40, Chimp Connexin 40, dog Connexin 40, cow Connexin 40, mouse Connexin 40, rat Connexin 40, Cricetulus Connexin 40, Chick Connexin 40, human Connexin 43, Cercopithecus Connexin 43, Oryctolagus Connexin 43, Spermophilus Connexin 43, Cricetulus Connexin 43, Phodopus Connexin 43, Rat Connexin 43, Sus Connexin 43, Mesocricetus Connexin 43, Mouse Connexin 43, Cavia Connexin 43, Cow Connexin 43, Erinaceus Connexin 43, Chick Connexin 43, Xenopus Connexin 43, Oryctolagus Connexin 43, Cyprinus Connexin 43, Zebrafish Connexin 43, Danio aequipinnatus Connexin 43, Zebrafish Connexin 43.4, Zebrafish Connexin 44.2, Zebrafish Connexin 44.1, human Connexin 45, chimp Connexin 45, dog Connexin 45, mouse Connexin 45, cow Connexin 45, rat Connexin 45, chick Connexin 45, Tetraodon Connexin 45, chick Connexin 45, human Connexin 46, chimp Connexin 46, mouse Connexin 46, dog Connexin 46, rat Connexin 46, Mesocricetus Connexin 46, Cricetulus Connexin 46, Chick Connexin 56, Zebrafish Connexin 39.9 cow Connexin 49, human Connexin 50, chimp Connexin 50, rat Connexin 50, mouse Connexin 50, dog Connexin 50, sheep Connexin 49, Mesocricetus Connexin 50, Cricetulus Connexin 50, Chick Connexin 50, human Connexin 59, or other alpha Connexin.

The 20-30 carboxy-terminal-most amino acid sequence of alpha Connexins are characterized by a distinctive and conserved organization. This distinctive and conserved organization includes a type II PDZ binding motif ($\Phi$-x-$\Phi$); wherein x=any amino acid and 1=a Hydrophobic amino acid) and proximal to this motif, Proline (P) and/or Glycine (G) hinge residues; a high frequency phospho-Serine (S) and/or phospho-Threonine (T) residues; and a high frequency of positively charged Arginine (R), Lysine (K) and negatively charged Aspartic acid (D) or Glutamic acid (E) amino acids. For many alpha Connexins, the P and G residues occur in clustered motifs proximal to the carboxy-terminal type II PDZ binding motif. The S and T phosphor-amino acids of most alpha Connexins also are typically organized in clustered, repeat-like motifs. This organization is particularly the case for Cx43, where 90% of 20 carboxyl terminal-most amino acids are comprised of the latter seven amino acids. In a further example of the high conservation of the sequence, ACT peptide organization of Cx43 is highly conserved from humans to fish.

Thus, in one aspect, the provided polypeptide comprises one, two, three or all of the amino acid motifs selected from the group consisting of 1) a type II PDZ binding motif, 2) Proline (P) and/or Glycine (G) hinge residues; 3) clusters of phospho-Serine (S) and/or phospho-Threonine (T) residues; and 4) a high frequency of positively charged Arginine (R) and Lysine (K) and negatively charged Aspartic acid (D) and/or Glutamic acid (E) amino acids). In another aspect, the provided polypeptide comprises a type II PDZ binding motif at the carboxy-terminus, Proline (P) and/or Glycine (G) hinge residues proximal to the PDZ binding motif, and positively charged residues (K, R, D, E) proximal to the hinge residues.

PDZ domains were originally identified as conserved sequence elements within the postsynaptic density protein PSD95/SAP90, the Drosophila tumor suppressor dlg-A, and the tight junction protein ZO-1. Although originally referred to as GLGF or DHR motifs, they are now known by an acronym representing these first three PDZ-containing proteins (PSD95/DLG/ZO-1). These 80-90 amino acid sequences have now been identified in well over 75 proteins and are characteristically expressed in multiple copies within a single protein. Thus, in one aspect, the provided polypeptide can inhibit the binding of an alpha Connexin to a protein comprising a PDZ domain. The PDZ domain is a specific type of protein-interaction module that has a structurally well-defined interaction 'pocket' that can be filled by a PDZ-binding motif, referred to herein as a "PDZ motif". PDZ motifs are consensus sequences that are normally, but not always, located at the extreme intracellular carboxyl terminus. Four types of PDZ motifs have been classified: type I (S/T-x-$\Phi$), type II ($\Phi$-x-$\Phi$), type III ($\Psi$-x-$\Phi$) and type IV (D-x-V), where x is any amino acid, $\Phi$ is a hydrophobic residue (V, I, L, A, G, W, C, M, F) and $\Psi$ is a basic, hydrophilic residue (H, R, K). (Songyang, Z., et al. 1997. Science 275, 73-77). Thus, in one aspect, the provided polypeptide comprises a type II PDZ binding motif.

When specific proteins are referred to herein, variants, derivatives, and fragments are contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known and include, for example, M13 primer mutagenesis and PCR mutagenesis. Amino acid substitutions are typically of single residues, but can occur at a number of different locations at once; insertions usually will be on the order of about from 1 to 10 amino acid residues. Substitutions, deletions, insertions or any combination thereof may be combined to arrive at a final construct. Substitutional variants are those in which at least one residue has been removed and a different residue inserted in its place.

For example, the replacement of one amino acid residue with another that is biologically and/or chemically similar is known to those skilled in the art as a conservative substitution. For example, a conservative substitution would be replacing one hydrophobic residue for another, or one polar residue for another. Conservatively substituted variations of each explicitly disclosed sequence are included within the polypeptides provided herein.

Typically, conservative substitutions have little to no impact on the biological activity of a resulting polypeptide. In a particular example, a conservative substitution is an amino acid substitution in a peptide that does not substantially affect the biological function of the peptide. A peptide can include one or more amino acid substitutions, for example 2-10 conservative substitutions, 2-5 conservative substitutions, 4-9 conservative substitutions, such as 2, 5 or 10 conservative substitutions.

A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using standard peptide synthesis methods. An alanine scan can be used to identify which amino acid residues in a protein can tolerate an amino acid substitution. In one example, the biological activity of the protein is not decreased by more than 25%, for example not more than 20%, for example not more than 10%, when an alanine, or other conservative amino acid (such as those listed below), is substituted for one or more native amino acids.

It is understood that there are numerous amino acid and peptide analogs which can be incorporated into the disclosed compositions. For example, there are numerous D amino acids. The opposite stereoisomers of naturally occurring peptides are disclosed, as well as the stereoisomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73

(1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994), all of which are herein incorporated by reference at least for material related to amino acid analogs).

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Thus, the provided polypeptide can comprise a conservative variant of the c-terminus of an alpha Connexin (ACT). It is understood that one way to define any variants, modifications, or derivatives of the disclosed genes and proteins herein is through defining the variants, modification, and derivatives in terms of sequence identity (also referred to herein as homology) to specific known sequences. Specifically disclosed are variants of the nucleic acids and polypeptides herein disclosed which have at least 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent sequence identity to the stated or known sequence.

Those of skill in the art readily understand how to determine the sequence identity of two proteins or nucleic acids. For example, the sequence identity can be calculated after aligning the two sequences so that the sequence identity is at its highest level. Another way of calculating sequence identity can be performed by published algorithms.

Thus, the provided polypeptide can comprise an amino acid sequence with at least 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent sequence identity to the c-terminus of an alpha Connexin (ACT). Thus, in one aspect, the provided polypeptide comprises an amino acid sequence with at least 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent sequence identity to SEQ ID NO:1, SEQ ID NO: 2, or any sequence provided herein.

In embodiments, the polypeptide comprises a cellular internalization transporter or sequence. The cellular internalization sequence can be any internalization sequence known or newly discovered in the art, or conservative variants thereof. Non-limiting examples of cellular internalization transporters and sequences include Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol). Exemplary cell internalization transporters are provided in Table 2A.

TABLE 2A

Exemplary cell internalization sequences

| Name | Sequence | SEQ ID NO |
|---|---|---|
| Antp | RQPKIWFPNRRKPWKK | (SEQ ID NO: 7) |
| HIV-Tat | GRKKRRQRPPQ | (SEQ ID NO: 14) |
| Penetratin | RQIKIWFQNRRMKWKK | (SEQ ID NO: 15) |
| Antp-3A | RQIAIWFQNRRMKWAA | (SEQ ID NO: 16) |
| Tat | RKKRRQRRR | (SEQ ID NO: 17) |
| Buforin II | TRSSRAGLQFPVGRVHRLLRK | (SEQ ID NO: 18) |
| Transportan | GWTLNSAGYLLGKINKALAALAKKIL | (SEQ ID NO: 19) |
| model amphipathic peptide (MAP) | KLALKLALKALKAALKLA | (SEQ ID NO: 20) |
| K-FGF | AAVALLPAVLLALLAP | (SEQ ID NO: 21) |
| Ku70 | VPMLK-PMLKE | (SEQ ID NO: 22) |
| Prion | MANLGYWLLALFVTMWTDVGLCKKRPKP | (SEQ ID NO: 23) |
| pVEC | LLIILRRRIRKQAHAHSK | (SEQ ID NO: 24) |
| Pep-1 | KETWWETWWTEWSQPKKKRKV | (SEQ ID NO: 25) |
| SynB1 | RGGRLSYSRRRFSTSTGR | (SEQ ID NO: 26) |
| Pep-7 | SDLWEMMMVSLACQY | (SEQ ID NO: 27) |
| FIN-1 | TSPLNIHNGQKL | (SEQ ID NO: 28) |

TABLE 2A-continued

Exemplary cell internalization sequences

| Name | Sequence | SEQ ID NO |
|---|---|---|
| BGSC (Bis-Guanidinium-Spermidine-Cholesterol) | (n/a) | |
| BGTC (Bis-Guanidinium-Tren-Cholesterol) | (n/a) | |

Any other internalization sequences now known or later identified can be combined with a peptide of the invention.

The provided polypeptide can comprise any aCT sequence (e.g, any of the aCT peptides disclosed herein) in combination with any of the herein provided cell internalization sequences. Examples of said combinations are provided in Table 2B. Thus, the provided polypeptide can comprise an Antennapedia sequence comprising amino acid sequence SEQ ID NO:7. Thus, the provided polypeptide can comprise the amino acid sequence SEQ ID NO:8, SEQ ID NO:9, SEQ ID NO:10, SEQ ID NO:11, or SEQ ID NO: 12.

TABLE 2B

ACT Polypeptides with Cell Internalization Sequences (CIS) aCT Polypeptides with Cell Internalization Sequences (CIS)

| CIS/ACT | Sequence | SEQ ID NO |
|---|---|---|
| Antp/ACT 2 | RQPKIWFPNRRKPWKK PSSRASSRASSRPRPDDLEI | SEQ ID NO: 8 |
| Antp/ACT 1 | RQPKIWFPNRRKPWKK RPRPDDLEI | SEQ ID NO: 9 |
| Antp/ACT 3 | RQPKIWFPNRRKPWKK RPRPDDLEV | SEQ ID NO: 10 |
| Antp/ACT 4 | RQPKIWFPNRRKPWKK RPRPDDVPV | SEQ ID NO: 11 |
| Antp/ACT 5 | RQPKIWFPNRRKPWKK KARSDDLSV | SEQ ID NO: 12 |
| HIV-Tat/ACT 1 | GRKKRRQRPPQ RPRPDDLEI | SEQ ID NO: 56 |
| Penetratin/ACT 1 | RQIKIWFQNRRMKWKK RPRPDDLEI | SEQ ID NO: 57 |
| Antp-3A/ACT 1 | RQIAIWFQNRRMKWAA RPRPDDLEI | SEQ ID NO: 58 |
| Tat/ACT1 | RKKRRQRRR RPRPDDLEI | SEQ ID NO: 59 |
| Buforin II/ACT 1 | TRSSRAGLQFPVGRVHRLLRK RPRPDDLEI | SEQ ID NO: 60 |
| Transportan/ACT 1 | GWTLNSAGYLLGKINKALAALAKKIL RPRPDDLEI | SEQ ID NO: 61 |
| MAP/ACT 1 | KLALKLALKALKAALKLA RPRPDDLEI | SEQ ID NO: 62 |
| K-FGF/ACT 1 | AAVALLPAVLLALLAP RPRPDDLEI | SEQ ID NO: 63 |
| Ku70/ACT 1 | VPMLKPMLKE RPRPDDLEI | SEQ ID NO: 64 |
| Prion/ACT 1 | MANLGYWLLALFVTMWTDVGLCKKRPKP RPRPDDLEI | SEQ ID NO: 65 |

TABLE 2B-continued

| ACT Polypeptides with Cell Internalization Sequences (CIS) aCT Polypeptides with Cell Internalization Sequences (CIS) | | |
|---|---|---|
| CIS/ACT | Sequence | SEQ ID NO |
| pVEC/ ACT 1 | LLIILRRRIRKQAHAHSK RPRPDDLEI | SEQ ID NO: 66 |
| Pep-1/ ACT 1 | KETWWETWWTEWSQPKKKRKV RPRPDDLEI | SEQ ID NO: 67 |
| SynB1/ ACT 1 | RGGRLSYSRRRFSTSTGR RPRPDDLEI | SEQ D NO: 68 |
| Pep-7/ ACT 1 | SDLWEMMMVSLACQY RPRPDDLEI | SEQ ID NO: 69 |
| HN-1/ ACT 1 | TSPLNIHNGQKL RPRPDDLEI | SEQ ID NO: 70 |

Also provided are isolated nucleic acids encoding the polypeptides provided herein. The disclosed nucleic acids are made up of for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U. Thus, provided is an isolated nucleic acid encoding a polypeptide comprising the amino acid sequence SEQ ID NO:1, SEQ ID NO:2, SEQ ID NO:3, SEQ ID NO:4, SEQ ID NO:5, SEQ ID NO:7, SEQ ID NO:8, SEQ ID NO:9, SEQ ID NO:10, SEQ ID NO:11, or SEQ ID NO:12.

In embodiments, provided herein is a composition comprising one or more of the herein provided polypeptides, nucleic acids, or vectors in a pharmaceutically acceptable carrier. For example, provided is a composition comprising SEQ ID NO:2 or SEQ ID NO:9 in a pharmaceutically acceptable carrier. In embodiments, the composition comprises one or more of the herein provided polypeptides encapsulated in a microcarrier. For example, in embodiments, the composition comprises one or more of the herein provided polypeptides, wherein the polypeptides are in a nanoparticle or exosome.

In embodiments, the compositions provided herein comprise drug loaded microcarrier formulations comprising nanoparticles or exosomes. In embodiments, the size of the nanoparticles is from about 100 nm to about 1000 nm, or about 100 nm to about 500 nm, or about 200 nm to about 250 nm, or about 100 nm to about 200 nm.

In embodiments, formulation comprises about 0.01% w/w to about 3.5% w/w, or about 0.05% w/w to about 3.0% w/w, or about 0.07% w/w to about 2.0% w/w, or about 0.1% w/w to about 1.0% w/w, or about 0.1% w/w to about 0.5% w/w, or about 0.2% w/w to about 0.8% w/w, or about 0.03% w/w to about 0.07% w/w, or about 0.05% w/w, of the polypeptide. In embodiments, the formulation comprises about 0.035% w/w of the polypeptide or about 0.07% w/w of the polypeptide or about 0.1% w/w of the polypeptide, or about 1.0% w/w of the peptide, or about 3.5% w/w of the polypeptide.

In embodiments, the formulation comprises about 0.00035 mg/mL to about 35 mg/mL, or about 0.001 mg/mL to about 20 mg/mL, or about 0.01 mg/mL to about 3.5 mg/mL, or about 0.1 mg/mL to about 1.0 mg/mL, or about 0.2 mg/mL to about 0.8 mg/mL, or about 0.3 mg/mL to about 0.7 mg/mL of the polypeptide. In embodiments, the formulation comprises about 0.1 mg/mL, about 0.2 mg/mL, about 0.3 mg/mL, about 0.35 mg/mL, about 0.4 mg/mL, about 0.5 mg/mL, about 0.6 mg/mL, about 0.7 mg/mL, about 0.8 mg/mL, about 0.9 mg/mL, or about 1.0 mg/mL of the polypeptide. In embodiments, the formulation comprises about 0.35 mg/mL or about 0.7 mg/mL of the polypeptide. In embodiments, the formulation comprises about 1 mg/mL or about 10 mg/mL or about 20 mg/mL of the polypeptide.

In embodiments, the composition is administered to the subject in a formulation comprising about 1 μM to about 100,000 μM, or about 10 μM to about 50,000 μM, or about 100 μM to about 10,000 μM, or about 10 μM to about 9,000 μM, or about 50 μM to about 5,000 μM, or about 100 μM to about 2,000 μM, or about 200 μM to about 2,000 μM, or about 200 μM to about 1,000 μM, or about 50 μM to about 1,500 μM of the polypeptide, or about 100 μM to about 1,000 μM of the polypeptide, or about 500 to about 1,500 μM of the polypeptide. In embodiments, the composition is administered to the subject in a formulation comprising about 1 μM , about 5 μM , about 50 μM, about 100 μM, about 150 μM, about 200 μM, about 300 μM, about 400 μM, about 500 μM, about 600 μM, about 700 μM, about 800 μM, about 900 μM, about 1,000 μM, about 1,500 μM, about 2,000 μM, about 3,000 μM, about 4,000 μM, about 5,000 μM, about 6,000 μM, about 7,000 μM, about 8,000 μM, about 9,000 μM, about 10,000 μM, about 20,000 μM, about 25,000 μM, about 50,000 μM, about 75,000 μM, about 100,000 μM, or more, of the polypeptide.

In embodiments, the formulation is administered to the eye immediately after the event that caused the ocular injury. In embodiments, the formulation is administered to the subject within about 1 hour, within about 2, hours, within about 3 hours, within about 4 hours, within about 5 hours, within about 6 hours, within about 8 hours, within about 12 hours, within about 18 hours, or within about 24 hours of the event the caused the ocular injury. In embodiments, the formulation is administered to the subject at least about 2 hours following the event that caused the ocular injury. In embodiments, the formulation is administered to the eye of the subject daily, e.g., once per day, or twice per day, and/or about every 8 hours or about every 12 hours. In embodiments, the formulation is administered until ocular healing is observed. In embodiments, the formulation is administered for at least about 2 days, at least about 3 days, at least about 4 days, at least about 5 days, at least about 6 days, at least about 7 days, or for longer. In embodiments, the formulation is administered chronically. As used herein, the term "administered chronically" means the formulation is administered for an open-ended dosing regimen, that is, treatment is started and intended to continue for an indefinite period of time and/or until symptoms resolve, etc. In embodiments, for chronic disease conditions, the formulation is administered to the eye upon detection of the chronic disease condition and is administered chronically. In embodiments, the formulation is administered chronically to subjects with corneal injuries resulting from chronic conditions such as dry eye disease (DED).

As used herein, "subject" include vertebrates, more specifically a mammal (e.g., a human, horse, pig, rabbit, dog, sheep, goat, non-human primate, cow, cat, guinea pig or rodent), a fish, a bird or a reptile or an amphibian. In embodiments, the subject is a human subject. The term does not denote a particular age or sex. Thus, adult and newborn subjects, as well as fetuses, whether male or female, are intended to be covered. In embodiments, a patient refers to a subject afflicted with a disease or disorder. In embodiments, a patient population refers to a particular, defined set of subjects having a disease or disorder or at risk of developing a particular disease or disorder.

As used herein, "inhibit," "inhibiting," and "inhibition" mean to decrease an activity, response, condition, disease, or other biological parameter. This can include, but is not limited to, the complete loss of activity, response, condition, or disease. Thus, the reduction can be a 10, 20, 30, 40, 50, 60, 70, 80, 90, 100%, or any amount of reduction in between as compared to native or control levels.

Ranges and values may be expressed herein as from "about" one particular value, and/or to "about" another particular value. When such a range is expressed, also specifically contemplated and considered disclosed is the range from the one particular value and/or to the other particular value unless the context specifically indicates otherwise. All of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed. As used herein, the term "about" and the like, when used in the context of a value, generally means plus or minus 10% of the value stated. For example, about 0.5 would include 0.45 and 0.55, about 10 would include 9 to 11, about 1000 would include 900 to 1100. It By "treat" or "treatment" is meant a method of reducing the effects of a disease or condition. Treatment can also refer to a method of reducing the underlying cause of the disease or condition itself rather than just the symptoms. The treatment can be any reduction from native levels and/or any improvement of clinical signs of the disease and/or any increase in survival or function; and can be but is not limited to the complete ablation of the disease, condition, or the symptoms of the disease or condition. For example, a disclosed method for treating corneal injury is considered to be a treatment if there is a reduction in one or more symptoms of the injury or if there is an improvement in the condition of the subject when compared to native levels in the same subject or control subjects. Thus, the reduction or improvement can be a 10, 20, 30, 40, 50, 60, 70, 80, 90, 100%, or any amount of reduction in between as compared to native or control levels. By "prevent" or "prevention" and the like is meant a method of preventing the onset or reducing the incidence or severity of corneal injury.

Publications, patents and patent applications cited herein are specifically incorporated by reference in their entireties. While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto The present disclosure is further illustrated by reference to the following Examples. However, it should be noted that these Examples, like the embodiments described above, are illustrative and are not to be construed as restricting the scope of the disclosure in any way.

EXAMPLES

Example 1

Comparative Studies Testing Buffered Formulations

Formulations comprising citrate buffer and either hydroxyethylcellulose (HEC) or hydroxypropyl methylcellulose (HPMC) were subjected to filtration feasibility, peptide stability, and mechanical viscosity studies. Stability and impurity analyses were performed using high performance liquid chromatography (HPLC) of final aCT1 eye drop formulations with a validated analytical method. Studies were also conducted to compare peptide filtration feasibility and peptide stability of formulations comprising different buffers and combinations of excipients.

First, HEC and HPMC solutions containing citrate buffer were prepared and tested for filtration feasibility. The HEC solutions tested contained 0.2% w/w, 0.15% w/w, or 0.125% w/w HEC, in 10 mM citrate buffer at pH 6.0. the HPMC solution tested contained 0.5% w/w HPMC in 10 mM citrate buffer at pH 6.0. Both solutions contained 0.07% ACT peptide, a 3.6 kDa peptide.

The solutions were tested for filterability through a 0.2 µm PES filter. The results of the study showed that the HPMC solution was easy to filter at the 0.5% (w/w) concentration through a 0.2 µm PES membrane 25 mm syringe filter. In contrast, the highest HEC solution (0.2% (w/w)) was difficult to filter through the PES syringe filter, as well as difficult to filter through 0.2 p.m PES filter using a unit with a vacuum pump, when prepared with a low shear mixer (magnetic stir bar). When prepared with a higher shear homogenizer, the higher concentration HEC solution was easier to filter. Both of the lower concentration HEC solutions could be filtered through the 0.2 µm PES filter.

A mechanical viscosity study was conducted using a TA AR1000 Rheometer. Viscosity at shear stress of 0.01 to 1,000 Pa was determined with sample gap of 500 at 25° C., and equilibration time 2 minutes. Viscosity of the 0.5% w/w HPMC solution was 57.3 mPaS; viscosity of the 0.15% w/v HEC solution was 3.7 mPaS.

Similar formulations comprising 0.07% aCT1 peptide, 10 mM citric acid, 0.9% NaCl, and either 0.2% HEC or 0.2% HPMC (pH 6.0) were assessed for peptide stability. Impurities were detected at 0 and 3 month timepoints.

In summary, while the formulations could be sterile filtered, viscosity was not considered to be within a range appropriate for retention on the ocular surface. A minimum shear viscosity of 10.2 mPaS is necessary for ocular retention in humans (Zaki et al., 1986). United States Pharmacopeia (USP) guidelines state 18-28 mPaS is the optimal viscosity range for eye drop formulations. Further, impurities were detected at 0 and 3 month stability timepoints. Thus, these formulations were not appropriate for ocular delivery. Taken together, the studies indicated that the inclusion of citrate buffer surprisingly produced a formulation with unfavorable characteristics.

Formulations comprising citrate buffer were compared to formulations comprising phosphate buffer. The solutions shown below in Table 3 were prepared. 100 mM citrate buffers of pH 4, 5, or 6 and 100 mM phosphate buffers of 6, 7, or 8 were prepared. HPMC solutions at 0.5% w/V HPMC were prepared using each of the individual buffers. The HPMC solutions were filtered using a 0.2 µM PES filter. 3.5 mg/mL aCT1 peptide was added to the filtered HPMC solution and mixed on a stir plate until a uniform, clear solution was obtained. The solution was then filtered into 10 mL clear vials with crimp seal.

TABLE 3

Citrate and Phosphate buffer formulations

| Formulation ID | Description |
|---|---|
| 5776 | 3.5 mg/mL aCT1, 0.5% w/w HPMC in 100 mM citrate buffer pH 4.0 |
| 5777 | 3.5 mg/mL aCT1, 0.5% w/w HPMC in 100 mM citrate buffer pH 5.0 |
| 5778 | 3.5 mg/mL aCT1, 0.5% w/w HPMC in 100 mM citrate buffer pH 6.0 |
| 5779 | 3.5 mg/mL aCT1, 0.5% w/w HPMC in 100 mM phosphate buffer pH 6.0 |
| 5780 | 3.5 mg/mL aCT1, 0.5% w/w HPMC in 100 mM phosphate buffer pH 7.0 |
| 5781 | 3.5 mg/mL aCT1, 0.5% w/w HPMC in 100 mM phosphate buffer pH 8.0 |

It was very difficult to filter the solutions at lower pH (4 and 5) in citrate buffer. Filtration of 0.5% w/v HPMC solution in 100 mM citrate buffer pH 6.0 and 100 mM phosphate buffer pH 6.0 were a bit difficult to filter when compared to 0.5% HPMC solution in 10 mM citrate buffer pH 6.0 (which was used in filtration feasibility studies). Of all the solutions, FID5780 (0.5% HPMC in 100 mM phosphate buffer pH 7.0) was easy to filter. Ease of filtration of each formulation (Formulation ID or FID as shown above in Table 3): FID 5780>5781>5779>5778. aCT1 peptide dissolved quickly in all the solutions.

However, impurities were detected in each of the formulations at 2 week and 4 week stability time points (Table 4). Accordingly, the inclusion of phosphate buffer, like citrate buffer, did not yield a formulation with favorable peptide stability.

TABLE 4

Impurities at 2 and 4 week stability time points

| Sample Description | Temp. | T0 Total impurities/ Largest Impurity | T2 W Total impurities/ Largest Impurity | T4 W Total impurities/ Largest Impurity |
|---|---|---|---|---|
| 0.35% aCT1, 0.5% HPMC, in 10 mM citrate buffer pH 4.0 | 25° C. | 0.75%/0.37% | 11.14%/6.39% | 17.03%/8.48% |
| 0.35% aCT1, 0.5% HPMC, in 10 mM citrate buffer pH 4.0 | 40° C. | | 30.38%/11.46% | 84.56%/40.97% |
| 0.35% aCT1, 0.5% HPMC, in 10 mM citrate buffer pH 5.0 | 25° C. | 0.49%/0.22% | 8.74%/1.72% | 11.47%/3.10% |
| 0.35% aCT1, 0.5% HPMC, in 10 mM citrate buffer pH 5.0 | 40° C. | | 14.90%/2.69% | 19.13%/4.67% |
| 0.35% aCT1, 0.5% HPMC, in 10 mM citrate buffer pH 6.0 | 25° C. | 1.55%/0.41% | 28.79%/11.57% | 38.92%/15.92% |
| 0.35% aCT1, 0.5% HPMC, in 10 mM citrate buffer pH 6.0 | 40° C. | | 27.72%/8.97% | 31.03%/8.68% |
| 0.35% aCT1, 0.5% HPMC, in 10 mM phosphate buffer pH 6.0 | 25° C. | 1.05%/0.24% | 24.37%/9.34% | 34.80%/13.59% |
| 0.35% aCT1, 0.5% HPMC, in 10 mM phosphate buffer pH 6.0 | 40° C. | | 27.8%/5.92% | 37.31%/15.77% |
| 0.35% aCT1, 0.5% HPMC, in 10 mM phosphate buffer pH 7.0 | 25° C. | 0.49%/0.20% | 13.44%/7.62% | 21.91%/13.55% |
| 0.35% aCT1, 0.5% HPMC, in 10 mM phosphate buffer pH 7.0 | 40° C. | | 53.82%/35.64% | 71.95%/49.63% |
| 0.35% aCT1, 0.5% HPMC, in 10 mM phosphate buffer pH 8.0 | 25° C. | 1.06%/0.51% | 37.92%/24.69% | 56.67%/37.74% |
| 0.35% aCT1, 0.5% HPMC, in 10 mM phosphate buffer pH 8.0 | 40° C. | | 96.29%/61.37% | 72.82%/63.04% |

To investigate low assay T0 testing in pH stability study and to evaluate filter suitability of formulations with and without HPMC, the following formulations shown in Table 5 were made.

TABLE 5

Further Citrate Buffer and HPMC formulations

| Sample ID | Description |
|---|---|
| LBR1421-001-13A | aCT1 0.35 mg/mL, Sodium chloride 0.8% w/v, HPMC 0.5%w/v in 10 mM citrate buffer pH 5.0 |
| LBR1421-001-13B | aCT1 0.35 mg/mL, Sodium chloride 0.8% w/v in 10 mM citrate buffer pH 5.0 |
| LBR1421-001-13C | aCT1 3.5 mg/mL, Sodium chloride 0.8% w/v, HPMC 0.5%w/v in 10 mM citrate buffer pH 5.0 |
| LBR1421-001-13D | aCT1 3.5 mg/mL, Sodium chloride 0.8% w/v in 10 mM citrate buffer pH 5.0 |

Each solution was filtered using 0.2 μM PES filter or 0.2 μM PVDF filter. Results are provided below in Table 6.

TABLE 6

Evaluation of filter suitability and assay results with or without HPMC in the formulation

| Sample Description | Lot | Filter | Peptide 328967 Assay (% Label Claim) |
|---|---|---|---|
| 0.35 mg/mL aCT1, 0.5% HPMC, 0.8% NaCl pH 5.0 (Citrate) | LBR1421-001-13A1 | Pre-Filter | 118.5% |
| 0.35 mg/mL aCT1, 0.5% HPMC, 0.8% NaCl pH 5.0 (Citrate) | LBR1421-001-13A2 | PES | 116.4% |
| 0.35 mg/mL aCT1, 0.5% HPMC, 0.8% NaCl pH 5.0 (Citrate) | LBR1421-001-13A3 | PVDF | 113.9% |
| 0.35 mg/mL aCT1, 0.8% NaCl pH 5.0 (Citrate) | LBR1421-001-13B1 | Pre-Filter | 107.3% |
| 0.35 mg/mL aCT1, 0.8% NaCl pH 5.0 (Citrate) | LBR1421-001-13B2 | PES | 107.8% |
| 0.35 mg/mL aCT1, 0.8% NaCl pH 5.0 (Citrate) | LBR1421-001-13B3 | PVDF | 105.8% |
| 3.5 mg/mL aCT1, 0.5% HPMC, 0.8% NaCl pH 5.0 (Citrate) | LBR1421-001-13C1 | Pre-Filter | 113.2% |
| 3.5 mg/mL aCT1, 0.5% HPMC, 0.8% NaCl pH 5.0 (Citrate) | LBR1421-001-13C4 | Pre-Filter (Plastic Container) | 106.7% |
| 3.5 mg/mL aCT1, 0.5% HPMC, 0.8% NaCl pH 5.0 (Citrate) | LBR1421-001-13C2 | PES | 109.4% |
| 3.5 mg/mL aCT1, 0.5% HPMC, 0.8% NaCl pH 5.0 (Citrate) | LBR1421-001-13C3 | PVDF | 109.1% |
| 3.5 mg/mL aCT1, 0.8% NaCl pH 5.0 (Citrate) | LBR1421-001-13D1 | Pre-Filter | 103.9% |
| 3.5 mg/mL aCT1, 0.8% NaCl pH 5.0 (Citrate) | LBR1421-001-13D4 | Pre-Filter (Plastic Container) | 103.0% |
| 3.5 mg/mL aCT1, 0.8% NaCl pH 5.0 (Citrate) | LBR1421-001-13D2 | PES | 103.2% |
| 3.5 mg/mL aCT1, 0.8% NaCl pH 5.0 (Citrate) | LBR1421-001-13D3 | PVDF | 103.1% |

The formulations containing citrate buffer were very difficult to filter at pH 4 or 5. Formulations containing citrate and phosphate buffers at pH 6 were very difficult to filter. Thus, while the amount of peptide determined to be in the formulation after filtering relative to the expected amount (% Label Claim; Table 6) was generally within a suitable range (generally a range of 97%-115% is considered suitable), the formulations were not suitably filterable using PES or PVDF filters.

Data from 3 month stability studies of citrate buffer vs. phosphate buffer formulations, with or without glycerin as the viscosity enhancer, is provided below in Tables 7-10. While aCT1 peptide stability was favorable in several of these formulations, impurity profiles (Tables 9-10) tested for formulations stored at 5° C. and 25° C. were outside acceptable ranges.

TABLE 7

5° C. Assay Results

| Formulation ID (FID) | Sample Description | T0[2] Assay (% LC[1]) | T3 M[3] Assay (% LC) | T6 M[4] Assay (% LC) |
|---|---|---|---|---|
| 5903 | 0.35% aCT1, 0.5% HPMC, 0.8% sodium chloride, in 10 mM citrate buffer pH 5 | 96.5% | 102.3% (Plastic) 102.1% (Glass) | 100.7% (Plastic) 102.2% (Glass) |
| 5905 | 0.35% aCT1, 0.5% HPMC, 2.25% glycerin, in 10 mM citrate buffer pH 5 | 95.6% | 101.8% (Plastic) 101.9% (Glass) | 100.7% (Plastic) 101.7% (Glass) |
| 5904 | 0.035% aCT1, 0.5% HPMC, 0.8% sodium chloride, in 10 mM citrate buffer pH 5 | 97.9% | 93.5% (Plastic) 92.0% (Glass) | 88.0% (Plastic) 88.1% (Glass) |
| 5906 | 0.035% aCT1, 0.5% HPMC, 2.25% glycerin, in 10 mM citrate buffer pH 5 | 99.7% | 91.0% (Plastic) 95.6% (Glass) | 91.1% (Plastic) 94.2% (Glass) |

[1]% LC = Percentage of Label Claim
[2]T0 = Time zero
[3]T3 M = Time 3 months of storage
[4]T6 M = Time 6 months of storage

TABLE 8

25° C./40% RH Assay Results
Table 6—aCT1 Stability in Citrate or Phosphate Buffer Formulations Stored in Accelerated Conditions (25° C./40% RH)

| Formulation ID (FID) | Sample Description | T0[2] Assay (% LC[1]) | T3 M[3] Assay (% LC) | T6 M[4] Assay (% LC) |
|---|---|---|---|---|
| 5903 | 0.35% aCT1, 0.5% HPMC, 0.8% sodium chloride, in 10 mM citrate buffer pH 5 | 96.5% | 94.7% (Plastic) 95.0% (Glass) | 88.4% (Plastic) 95.0% (Glass) |

TABLE 8-continued

25° C./40% RH Assay Results
Table 6—aCT1 Stability in Citrate or Phosphate Buffer Formulations
Stored in Accelerated Conditions (25° C./40% RH)

| Formulation ID (FID) | Sample Description | T0[2] Assay (% LC[1]) | T3 M[3] Assay (% LC) | T6 M[4] Assay (% LC) |
|---|---|---|---|---|
| 5905 | 0.35% aCT1, 0.5% HPMC, 2.25% glycerin, in 10 mM citrate buffer pH 5 | 95.6% | 84.2% (Plastic) 90.8% (Glass) | NT[5] (Plastic) 80.9% (Glass) |
| 5908 | 0.35% aCT1, 0.5% HPMC, 2.25% glycerin, in 10 mM phosphate buffer pH 5 | 96.6% | 84.0% (Plastic) 91.4% (Glass) | NT[5] (Plastic) NT[5] (Glass) |
| 5904 | 0.035% aCT1, 0.5% HPMC, 0.8% sodium chloride, in 10 mM citrate buffer pH 5 | 97.9% | 73.5% (Plastic) 78.6% (Glass) | 47.2% (Plastic) 65.4% (Glass) |
| 5906 | 0.035% aCT1, 0.5% HPMC, 2.25% glycerin, in 10 mM citrate buffer pH 5 | 99.7% | 35.8% (Plastic) 81.6% (Glass) | NT[6] (Plastic) NT[6] (Glass) |
| 5909 | 0.035% aCT1, 0.5% HPMC, 2.25% glycerin, in 10 mM phosphate buffer pH 5 | 101.0% | 42.8% (Plastic) 80.8% (Glass) | 9.7% (Plastic) 59.2% (Glass) |

[1]% LC = Percentage of Label Claim
[2]T0 = Time zero
[3]T3 M = Time 3 months of storage
[4]T6 M = Time 6 months of storage
[5]Not Tested

TABLE 9

5° C. Impurity Results

| Formulation ID (FID) | Sample Description | T0[1] Total Impurities/ Largest Impurity | T3 M[2] Total Impurities/ Largest Impurity | T6 M[3] Total Impurities/ Largest Impurity |
|---|---|---|---|---|
| 5903 | 0.35% aCT1, 0.5% HPMC, 0.8% sodium chloride, in 10 mM citrate buffer pH 5 | 2.11%/0.69% | 3.80%/1.59% (Plastic) 3.90%/1.62% (Glass) | 4.81%/1.80% (Plastic) 4.41%/1.80% (Glass) |
| 5905 | 0.35% aCT1, 0.5% HPMC, 2.25% glycerin, in 10 mM citrate buffer pH 5 | 2.15%/0.73% | 4.20%/1.52% (Plastic) 3.80%/1.46% (Glass) | 5.52%/2.20% (Plastic) 4.73%/1.91% (Glass) |
| 5904 | 0.035% aCT1, 0.5% HPMC, 0.8% sodium chloride, in 10 mM citrate buffer pH 5 | 3.35%/2.02% | 6.01%/3.93% (Plastic) 7.03%/4.13% (Glass) | 11.70%/5.61% (Plastic) 11.61%/5.53% (Glass) |
| 5906 | 0.035% aCT1, 0.5% HPMC, 2.25% glycerin, in 10 mM citrate buffer pH 5 | 3.94%/2.46% | 8.63%/6.91% (Plastic) 5.75%/3.02% (Glass) | 12.24%/6.82% (Plastic) 9.61%/3.60% (Glass) |

TABLE 10

25° C./40% RH Impurity Results

| Formulation ID (FID) | Sample Description | T0[1] Total Impurities/ Largest Impurity | T3 M[2] Total Impurities/ Largest Impurity | T6 M[3] Total Impurities/ Largest Impurity |
|---|---|---|---|---|
| 5903 | 0.35% aCT1, 0.5% HPMC, 0.8% sodium chloride, in 10 mM citrate buffer pH 5 | 2.11%/0.69% | 13.64%/3.36% (Plastic) 9.50%/3.04% (Glass) | 22.69%/9.11% (Plastic) 13.28%/3.67% (Glass) |
| 5905 | 0.35% aCT1, 0.5% HPMC, 2.25% glycerin, in 10 mM citrate buffer pH 5 | 2.15%/0.73% | 18.24%/5.90% (Plastic) 11.80%/3.08% (Glass) | NT[4] (Plastic) 25.44%/4.71% (Glass) |
| 5908 | 0.35% aCT1, 0.5% HPMC, 2.25% glycerin, in 10 mM phosphate buffer pH 5 | 2.07%/0.69% | 22.72%/8.06% (Plastic) 11.10%/2.82% (Glass) | NT[4] (Plastic) NT[4] (Glass) |
| 5904 | 0.035% aCT1, 0.5% HPMC, 0.8% sodium chloride, in 10 mM citrate buffer pH 5 | 3.35%/2.02% | 18.70%/13.34% (Plastic) 8.36%/3.90% (Glass) | 57.81%/25.91% (Plastic) 31.14%/10.60% (Glass) |
| 5906 | 0.035% aCT1, 0.5% HPMC, 2.25% glycerin, in 10 mM citrate buffer pH 5 | 3.94%/2.46% | 41.44%/36.45% (Plastic) 17.61%/4.15% (Glass) | NT[4] (Plastic) NT[4] (Glass) |
| 5909 | 0.035% aCT1, 0.5% HPMC, 2.25% glycerin, in 10 mM phosphate buffer pH 5 | 3.25%/1.86% | 45.53%/32.92% (Plastic) 18.53%/6.72% (Glass) | 86.10%/44.39% (Plastic) 40.49%/10.47% (Glass) |

Taken together, the studies suggested that surprisingly, only formulations comprising HPMC (and not HEC, CMC, or glycerin) and excluding any buffer exhibit favorable properties for topical ocular administration.

Example 2

Comparative Studies Testing HPMC Formulations With or Without Additives

The additives mannitol, edetate disodium, sodium metabisulfite, and vitamin E TPGS were individually tested in the formulation provided in Table 11. These are FDA approved excipients for ocular use.

TABLE 11

Formulation used to test additives

| Component | Concentration |
|---|---|
| aCT1 Peptide | 0.035% (w/w) |
| NaCl | 0.9% (w/w) |
| HPMC | 0.5% (w/w) |
| Additive (1.0% mannitol, 0.2% edetate disodium, 0.2% sodium metabisulfite, or 0.25% vitamin E TPGS) | (w/w as indicated at left) |
| Purified water | q.s. |
| pH | 4.0-8.0 |

TABLE 12

5° C. Assay Results—Plastic container

| Sample Description | T0 Assay (% LC) | T1 M Assay (% LC) | T3 M Assay (% LC) | T6 M Assay (% LC) |
|---|---|---|---|---|
| 0.7 mg/mL aCT1 peptide (Vit. E, Mannitol, EDTA) | 100.4 | 102.2 | 99.3 | 103.0 |
| 0.7 mg/mL aCT1 peptide (Vit E, TPGS, EDTA) | 101.0 | 103.0 | 99.5 | 102.8 |
| 0.7 mg/mL aCT1 peptide (Vit E, TPGS) | 100.3 | 102.3 | 100.0 | 103.9 |
| 0.7 mg/mL aCT1 peptide (EDTA) | 101.5 | 102.8 | 99.2 | 100.2 |
| 0.7 mg/mL aCT1 peptide (Control—no additive) | 100.7 | 102.3 | 99.1 | 100.7 |

TABLE 13

5° C. Assay Results—Glass container

| Sample Description | T0 Assay (% LC) | T1 M Assay (% LC) | T3 M Assay (% LC) | T6 M Assay (% LC) Prep1/Prep 2 |
|---|---|---|---|---|
| 0.7 mg/mL aCT1 peptide (Vit. E, Mannitol, EDTA) | 101.4 | 103.3 | 100.2 | 123.8/104.1 |
| 0.7 mg/mL aCT1 peptide (Vit E, TPGS, EDTA) | 101.2 | 103.2 | 102.0 | 107.4/112.1 |
| 0.7 mg/mL aCT1 peptide (Vit E, TPGS) | 100.5 | 102.6 | 100.8 | 110.9/105.3 |
| 0.7 mg/mL aCT1 peptide (EDTA) | 100.7 | 103.4 | 100.2 | 117.4/105.3 |
| 0.7 mg/mL aCT1 peptide (Control—no additive) | 100.6 | 102.7 | 99.5 | 103.8/103.5 |

Impurity results showed inconsistencies prep-to-prep in glass container samples and presence of impurities with these tested formulations. None of the additives tested improved peptide stability in the formulation. Accordingly, formulations excluding all of these additives was selected for further testing, including in vivo testing described below in Examples 4-6.

Example 3

Comparative In Vivo Studies of Formulations Comprising a Peptide for Eye Drop Administration The excipients shown below in Table 14 were used to prepare formulations containing aCT1 peptide at concentrations ranging from 100 μM to 10,000 μM, and the solubility and potential for effective delivery to the eye were tested. Specifically, formulations containing NaCl, polymer hydroxypropyl methylcellulose (HPMC), Pluronic® F-127 (PF-127), hydroxyethylcellulose (HEC), and carboxymethylcellulose (CMC) were compared. The formulations tested did not include any additives or buffers.

TABLE 14

Vehicles for comparative analysis

| Vehicle | Concentration (w/v) |
|---|---|
| Hydroxypropyl methylcellulose (HPMC) | 0.5-1% |
| PF-127 | 20-25% |
| Hydroxyethylcellulose (HEC) | 0.5-1% |
| Carboxymethylcellulose (CMC) | 0.5% |
| NaCl | 0.9% |

The formulations were administered topically to the eye of Dutch Belted rabbits. aCT1 peptide was soluble in saline at all concentrations, however the formulation did not remain in contact with the ocular surface for a period of time sufficient to obtain delivery of the medication to the cornea. The addition of the viscosity modifier carboxymethylcellulose (CMC) to the dose formulation caused aggregation. In contrast, the addition of the viscoelastic polymer hydroxypropyl methylcellulose (HPMC) to the formulation did not cause aCT1 peptide aggregation or precipitation.

Example 4 Tolerability and distribution study of twice daily administration

A study was conducted to determine the safety, tolerability, and biodistribution of twice daily ocular administration of aCT1 peptide in an HPMC formulation, for 7 consecutive days.

Dose formulations were prepared by mixing the appropriate amount of test article in the vehicle (1% HPMC) to achieve the target concentration (see dose concentrations in Table 15, below). The formulation comprised 1% w/w HPMC and 0.9% w/w NaCl, and excluded buffers, preservatives, other vehicles, and other excipients. The formulation pH was recorded after filtration and was between 5.9 to 7.6, depending on the concentration of the formulation. Each does of the day was given 8 hours apart in a dosing volume of 0.1 mL to each eye.

TABLE 15

Experimental design

| Group | Treatment | Dose level (μmol/eye/dose) | Dose concentration (μM) | pH |
|---|---|---|---|---|
| 1 | Vehicle control | 0 | 0 | 7.2-7.6 |
| 2 | aCT1 | 0.01 | 100 | 5.9 |
| 3 | aCT1 | 0.1 | 1,000 | 6.3 |
| 4 | aCT1 | 1.0 | 10,000 | 5.9-6.0 |

Topical ocular administration of aCT1 twice daily for seven consecutive days was well-tolerated and did not result in any adverse findings in cage-side or clinical observations, body weight, clinical pathology, organ weight, or necropsy. Examination of the eyes showed irritation of eyelids and conjunctiva as well as stippling of cornea, and flaking of the eyelids for some animals in all groups including the control group; indicating that these findings were attributed to the viscosity of the vehicle and not to treatment with aCT1. There were also no microscopic findings in the eye tissues that were exposed to aCT1.

Tissue distribution of aCT1 was determined in rabbits administered 0.1 μmol/eye/dose. Whole blood concentrations of aCT1 were low but measurable in all three male rabbits at 0.25 hr on Day 1 at 0.25 hr were 3.26±5.28 ng/ml. All other blood samples from Day 1 and all from Day 7 were below the lower limit of quantitation (LLOQ). The highest concentrations of aCT1 in ocular tissues were observed in the palpebral conjunctiva in both males and females. All animals sampled had quantifiable concentrations of aCT1 in this tissue after dosing on Days 1 and 7. The highest mean concentration was on Day 1 at 0.25 hr, 939±228 ng/g (males) and 2730±697 ng/g (females). The cornea and aqueous humor had the next highest mean levels of aCT1, 181±50.0 ng/g (cornea, Day 1, 0.25 hr in females) and 115±76.3 ng/g (aqueous humor, Day 1, 0.25 hr in males). The vitreous humor contained quantifiable levels of aCT1 in at least one animal at each timepoint after dose administration on Days 1 and 7. aCT1 was measurable in retinal tissues of all rabbits on Day 1 at 0.25 hr, with concentrations ranging from 1.91 ng/g (female 040) to 24.2 ng/g (female 24.2 ng/g).

Concentrations of aCT1 in all tissues tended to decrease with time. There were no consistent differences in aCT1 distribution observed in male and female rabbits. All blood and tissue samples collected prior to dose administration were below the lower limit of quantitation for aCT1. Systemic exposure to aCT1 was minor as shown by low levels of the test article in blood at 0.25 hr after ocular administration to the eye on Day 1. One male also had quantifiable levels of aCT1 at 4 hr on Day 7. aCT1 was rapidly absorbed into ocular tissues as the Tmax was 0.25 hr on Day 1, for all eye tissues.

In conclusion, the highest concentrations of aCT1 were observed in the palpebral conjunctiva, a tissue that is in direct contact with the dose formulation. The cornea and aqueous humor also had high exposure to aCT1. The solution also achieved delivery of ACT to the innermost tissues of the eye including the retina, a surprising result given the challenges associated with delivery of peptides to the eye as described herein.

Despite exposure of eye tissues and blood to aCT1, there were no adverse effect that could be attributed to the treatment with aCT1 and histopathology of the eyes exposed to aCT1 did not show any abnormal findings. Therefore, no maximum tolerated dose (MTD) was identified in the study. The no observed adverse effect level (NOAEL) is estimated to be at 1.0 μmol/eye when administered twice daily for 7 days.

Taken together, the results of the study indicated that HPMC can be used in an ophthalmic delivery system for aCT1 peptide and safely achieve therapeutic levels of aCT1 in tissues of interest including the retina.

Example 5

Corneal Regeneration and Reepithelialization Following Corneal Injury and Treatment with aCT1 Peptide in HPMC There are no FDA approved therapeutics that effectively accelerate corneal reepithelialization. Studies were conducted to determine if aCT1 peptide can induce and/or accelerate corneal healing following ocular injury.

Figure 2B:
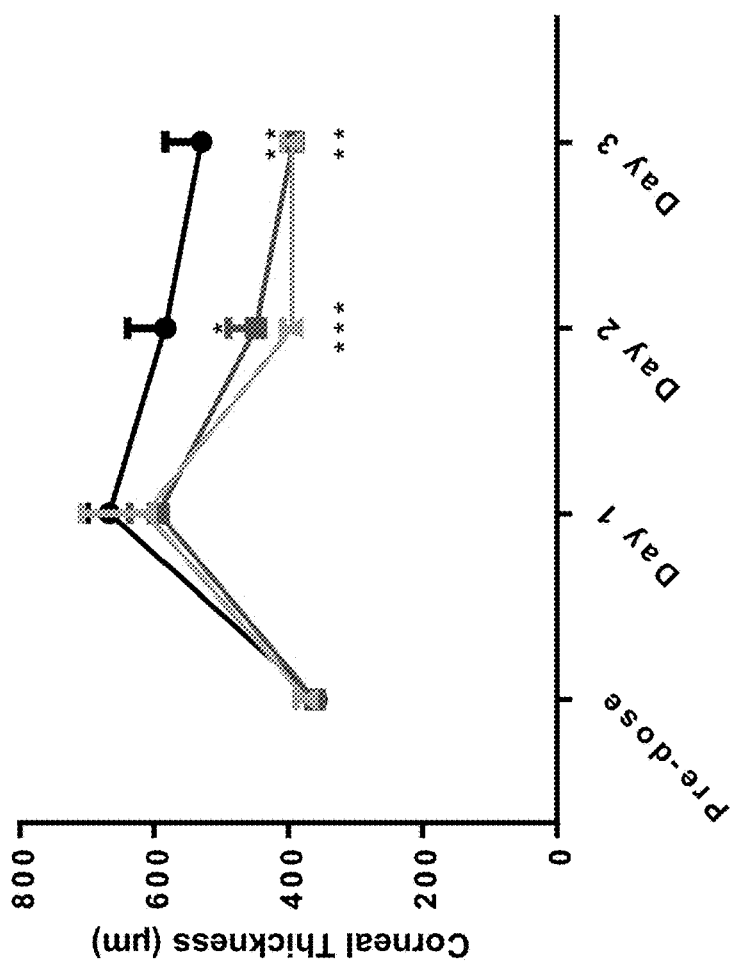
FIG. 2B shows central corneal thickness (μm) in rabbit eyes pre-dose and at day 1, day 2, and day 3 following corneal chemical burn, with eye drop administration of aCT1 peptide (200 μM or 5 mM) or vehicle control.
Figure 2A:
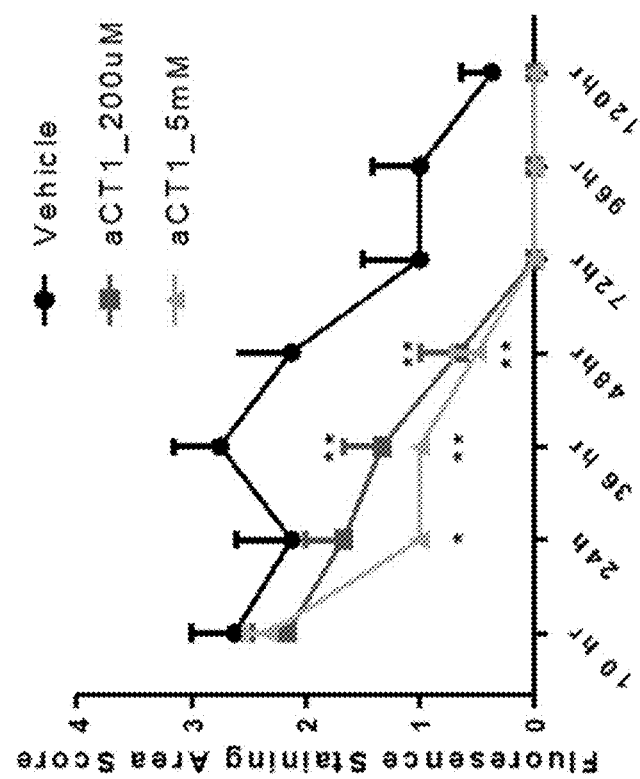
FIG. 2A is a bar graph showing the quantified fluorescence staining of FIG. 1 (n=6 per treatment group; *p<0.05, p<0.01 *p<0.001; SEM).

In one study, 200 μM and 5 mM aCT1 formulations in 1% HPMC were tested for their ability to promote corneal regeneration following heptanol-induced corneal erosion (chemical burn injury) in rabbit eyes. The formulation comprised 1% w/w HPMC and 0.9% w/w NaCl, and excluded buffers, preservatives, other vehicles, and other excipients. aCT1 eye drops were administered immediately post-injury and then twice daily for 2 days. aCT1 accelerated corneal healing following chemical burn injury as measured by fluorescein staining (FIGS. 1 and 2A) and as measured by central corneal thickness (FIG. 2B).

Figure 3:
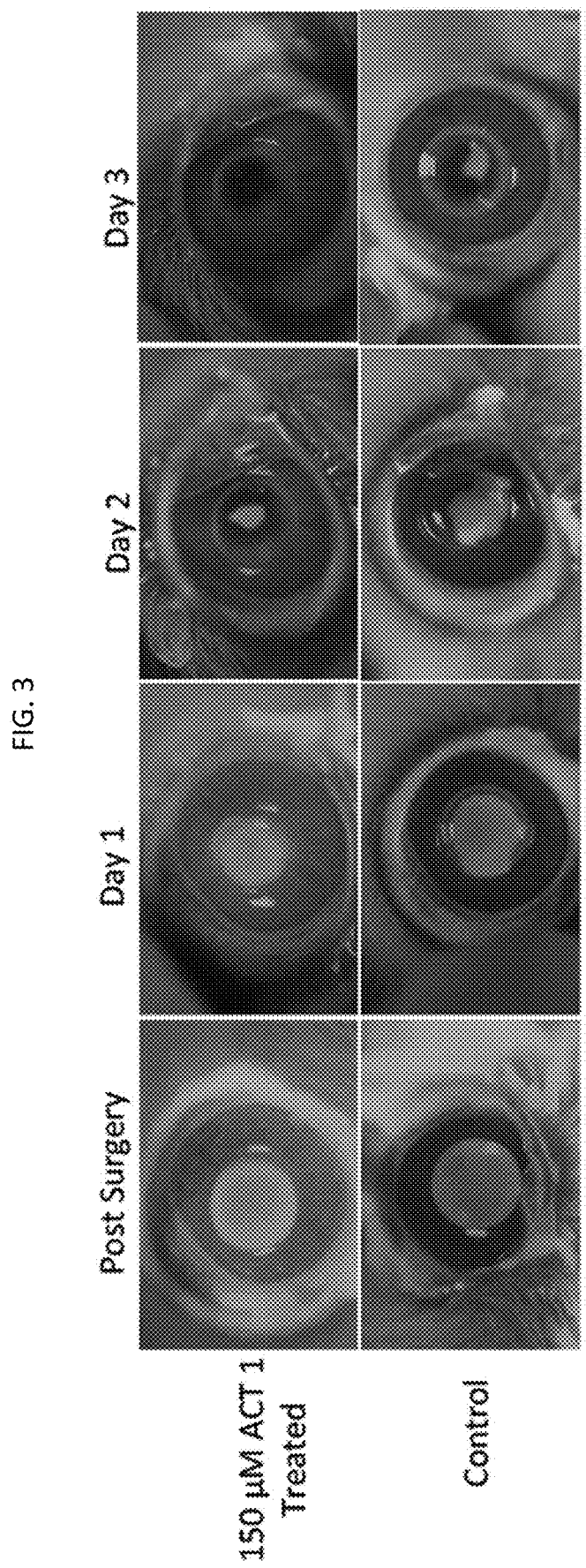
FIG. 3 shows 1% fluorescein staining of rabbit eyes after bilateral central transepithelial phototherapeutic keratectomy (PTK) surgery and treatment with aCT1 peptide (150 μM) or vehicle control.
Figure 4A:
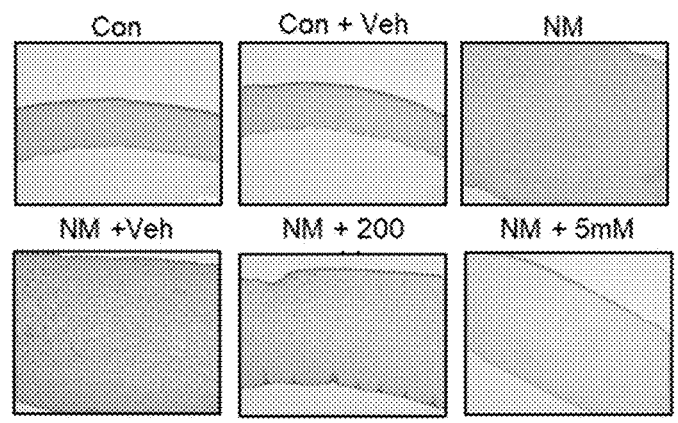
FIGS. 4A-4B show that treatment with aCT1 peptide decreases corneal thickening that occurs following corneal exposure to nitrogen mustard (NM).
Figure 4B:
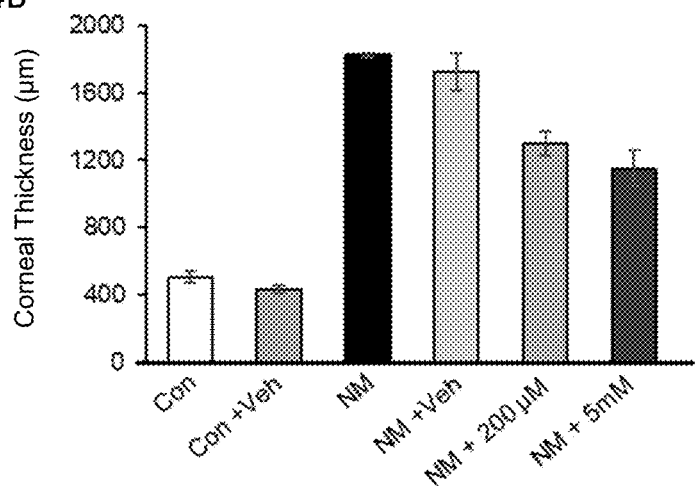
Figure 5C:
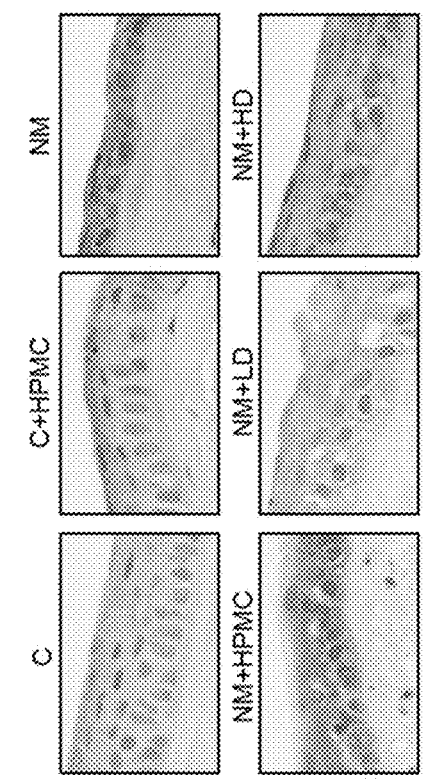
FIGS. 5A-5D show that treatment with aCT1 peptide decreases inflammatory responses in nitrogen mustard (NM)-exposed cornea.
Figure 5D:
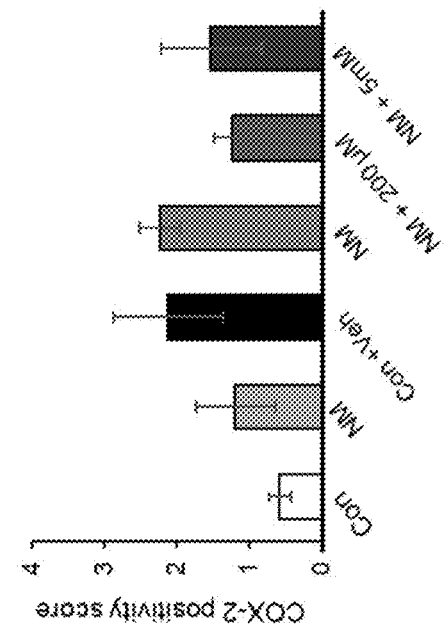
Figure 5A:
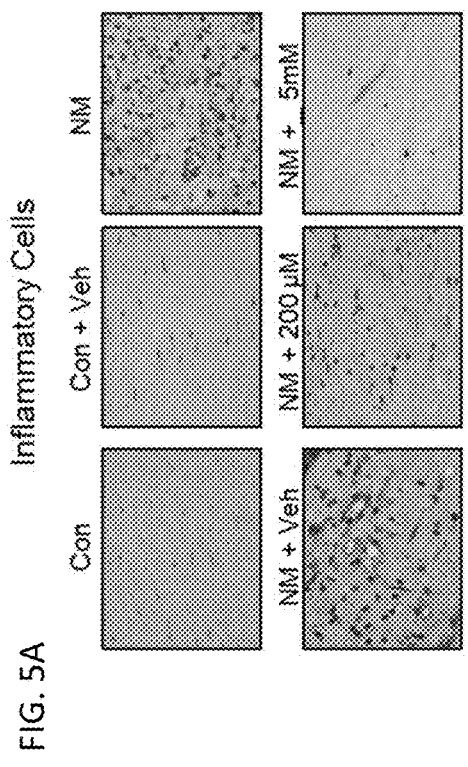
Figure 5B:
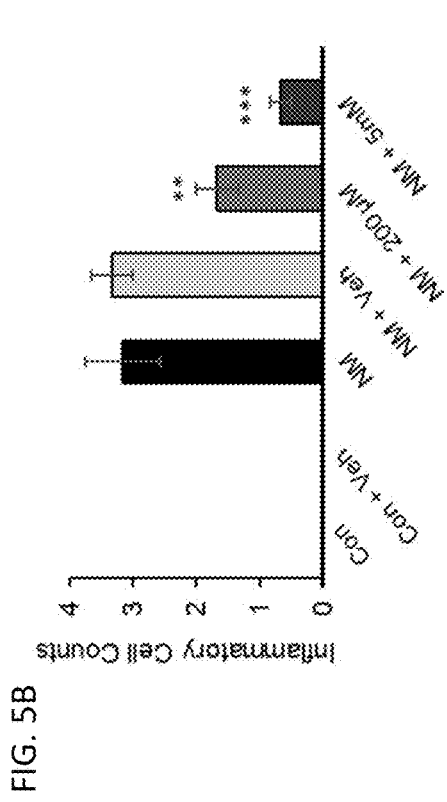

In another study, rabbits were anesthetized and the corneas (bilateral) received a central 6.0 mm diameter×150 μm deep injury (transepithelial PTK injury). Immediately after the injury, the cornea was stained with fluorescein and imaged to being monitoring the size of the injury. Eyes were treated with 150 μM aCT1 0.5% HPMC or a vehicle control. The results are shown in FIG. 3. Eyes treated with aCT1 peptide showed accelerated corneal healing. Given that timely epithelial resurfacing is critical to prevent loss of function, ocular morbidity, and vision loss, the early (within 3 days) difference between the aCT1 treated and control eyes is highly clinically significant.

Example 6 aCT1 Peptide Treatment of Sulfur Mustard-Induced Ocular Injury

Sulfur mustard (SM) and nitrogen mustard (NM) are potent vesicating chemical warfare agents affecting the eyes, skin, and respiratory system. Among vesicating agents, SM has been most widely used in warfare resulting in injuries and battlefield causalities. The eye is the most sensitive tissue to vesicant exposure, with symptoms appearing 2-6 hrs after exposure, and healing occurring a few weeks later. Ocular exposure is associated with delayed injury symptoms: dryness, conjunctival scarring, decreased visual acuity, persistent corneal defects, inflammation, and neovascularization leading to progressive visual deterioration. Currently, there is no approved therapy for ocular exposure to ocular vesicants, including SM and NM.

Accordingly, a study was conducted to assess the therapeutic potential of aCT1 eye drops in the treatment of such a vesicating warfare agent. New Zealand white rabbits (n=3 per treatment group) were exposed to 25 μL 1% nitrogen mustard in saline (NM). Corneas were treated with vehicle control (0.5% HPMC) or with 200 μM aCT1 in 0.5% HPMC, or with 5 mM aCT1 in 0.5% HPMC. The formulations comprised 0.5% w/w HPMC and 0.9% w/w NaCl, and excluded buffers, preservatives, other vehicles, and other excipients. Treatments were applied at 2 hours post-exposure, and then every 12 hours for 7 days. Healthy (uninjured) corneas were also untreated or treated with vehicle only. Animals were euthanized at 7 days post-exposure. Corneas were collected and processed for histology (H&E staining) or immunohistochemistry.

The results of the study are provided in FIGS. 4-7. ACT treatment limited corneal edema following NM exposure. FIGS. 4A and 4B show that aCT1 peptide limited corneal edema damage compared to untreated and vehicle-treated NM-exposed corneas. aCT1 treatment also decreased pro-inflammatory response in the cornea following NM exposure (FIGS. 5A-5D). A pro-inflammatory response and the recruitment of inflammatory cells can exacerbate tissue damage leading to corneal opacity and scarring. H&E staining showed that aCT1 significantly decreases inflammatory cell infiltration in the corneal stroma in NM-exposed cornea compared to untreated and vehicle-treated NM-exposed corneas (FIGS. 5A and 5B). Expression of the pro-inflammatory enzyme COX-2 was also reduced in aCT1 treated groups (FIGS. 5C and 5D), which may in part mediate the reduction in inflammatory cell infiltration.

Figure 6A:
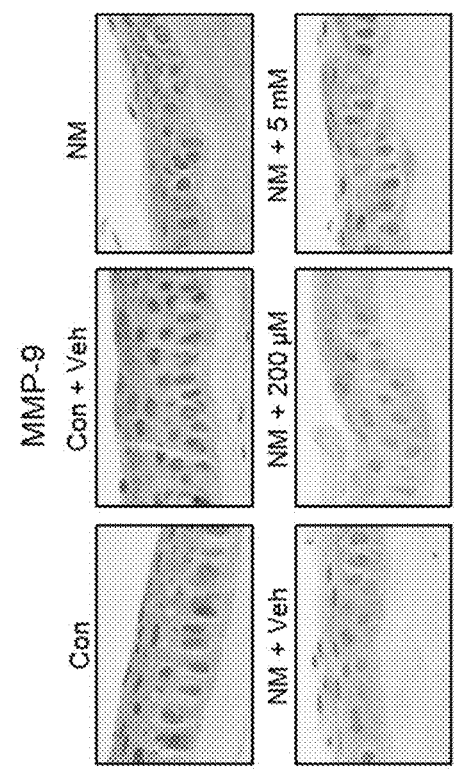
FIGS. 6A-6D show that aCT1 treatment of NM-exposed corneas may protect corneal fibroblasts and keratocytes.
Figure 6C:
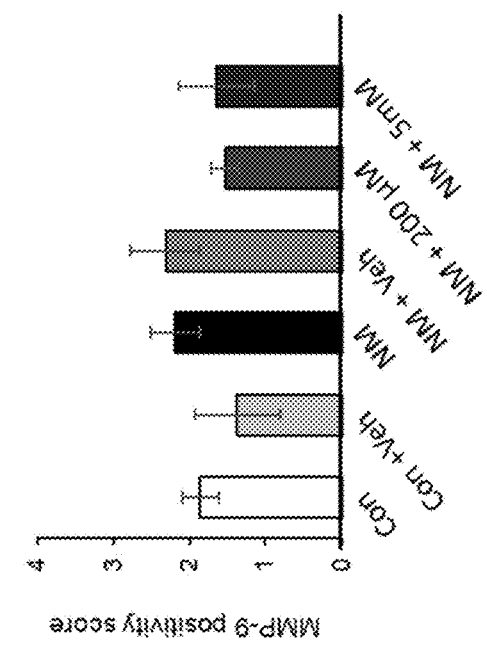
Figure 6B:
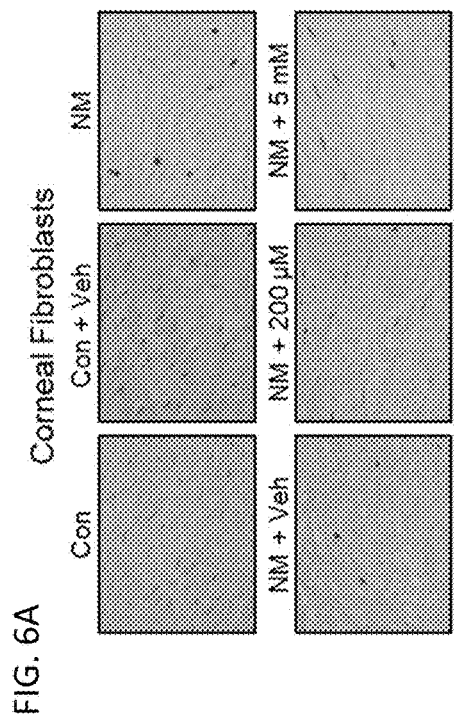
Figure 6D:
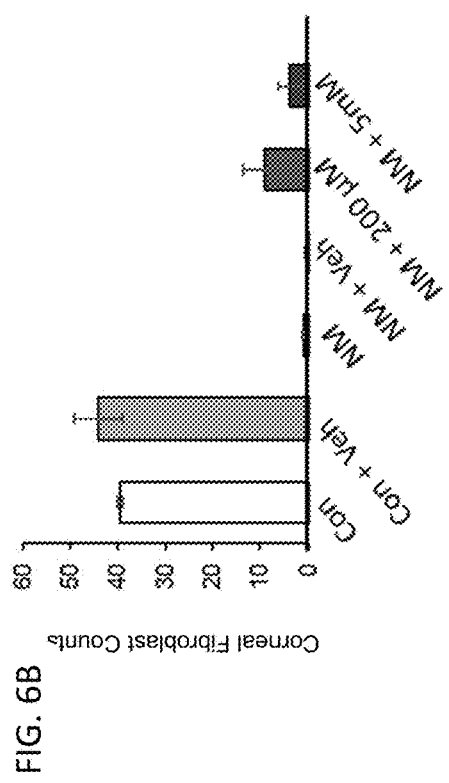

Collagen synthesis by corneal fibroblasts (also referred to as corneal keratocytes) is essential to stromal maintenance and regeneration, and increased expression and activity of matrix metallopeptidase-9 (MMP-9) in the corneal stroma leads to its degradation. aCT1 treatment prevented degradation and promoted regeneration of the corneal stroma following NM exposure, as evidenced by the protection of corneal fibroblasts/keratocytes in the aCT1 treated cornea (FIGS. 6A and 6B) as well as the reduction in MMP-9 expression in the stroma in aCT1 treated corneas (FIGS. 6C and 6D).

Figure 7A:
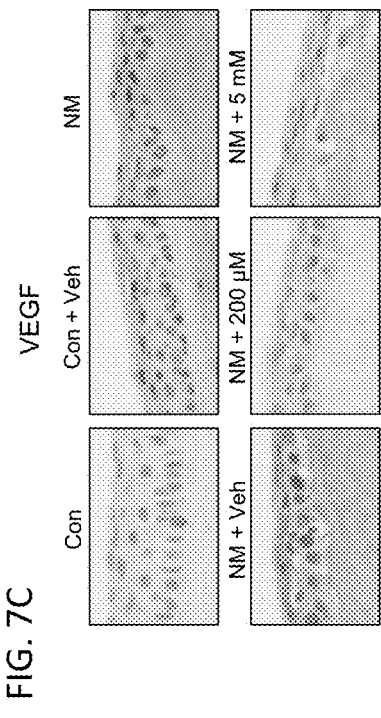
FIGS. 7A-7D show that treatment with aCT1 peptide reduces corneal neovascularization in NM-exposed corneas.
Figure 7C:
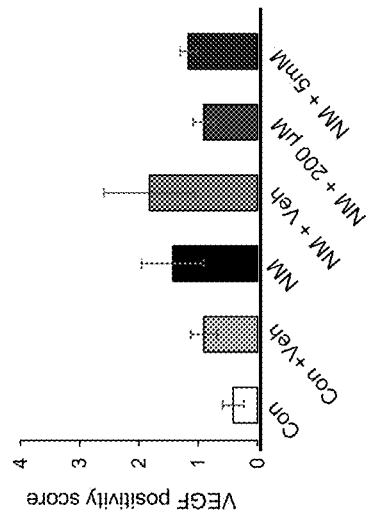
Figure 7B:
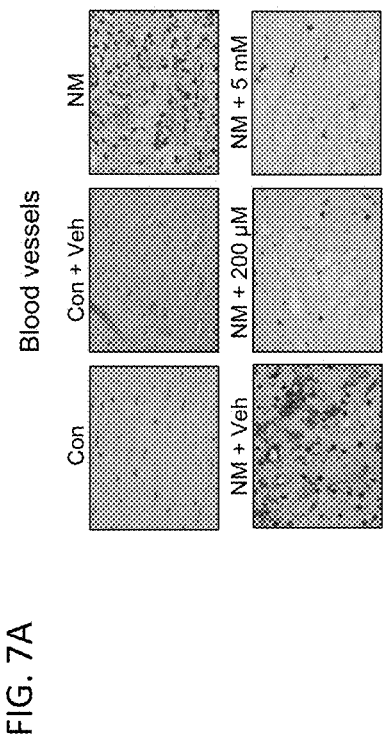
Figure 7D:
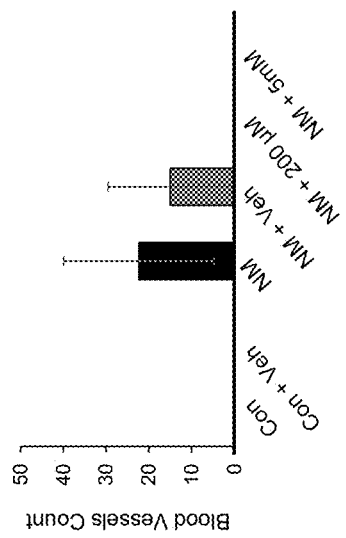

Ocular exposure to vesicating agents also induces corneal neovascularization, which results in corneal opacity and dysfunction. The study showed that aCT1 prevented corneal neovascularization. FIGS. 7A and 7B show that aCT1 treatment limited the formation of new blood vessels in the corneal stroma. The lack of new blood vessels in the treatment group corresponded to a pattern of decreased vascular endothelial growth factor (VEGF, a signaling factor that stimulates neovascularization) expression (FIGS. 7C and 7D).

Taken together, the results of the study showed that the administration of the aCT1 formulation was surprisingly potent in protecting against sulfur mustard-induced ocular injury and speeding the regeneration of the corneal stroma following such injury. The aCT1 peptide has positive effects on several cell types and activities necessary to corneal healing and thus is uniquely capable of effective treatment and prevention of corneal injuries.

Example 7

Evaluation of an Optimal aCT1 Formulation for Therapeutic Use

Studies were conducted to evaluate characteristics of a novel aCT1 eye drop formulation composed of aCT1 peptide, sodium chloride, and HPMC (4000 mPaS; Table 16). Surprisingly, this formulation, free of preservatives, excipients, or buffer solutions, provided a formulation that possessed a viscosity within recommended range for topical delivery to the eye and demonstrated peptide stability during storage. Furthermore, recovery testing of this formulation demonstrated feasibility of sterile filtration as well as compatibility of the formulation with validated HPLC test methods to confirm eye drop specifications (Tables 17 and 18). Assays were conducted to evaluate the compatibility of this formulation with sterile filtration and analytical method for determining peptide concentration. Compatibility with the analytical method is necessary for ensuring the product remains within specification. Complete recovery of aCT1 peptide was demonstrated following sterile filtration of this optimal formulation following storage in glass or plastic (Table 17). Peptide stability at 0, 1 and 3 months storage at −20° C., 5° C., and 25° C. for formulations comprising 0.7% w/w or 1.8% w/w aCT1 peptide are shown in Table 19.

Accordingly, provided herein is a stable eye drop formulation having superior formulation properties for delivery of a peptide to an eye, including superior properties relative to various other vehicles tested and compared to formulations that include preservatives, excipients, or buffer solutions (see Examples 1-3). The formulations provided herein may be used to optimally deliver a peptide therapeutic agent such as aCT1 peptide to an eye for therapeutic use.

TABLE 16

Optimal Eye Drop Formulation

| Components | Concentration (% w/w) |
| --- | --- |
| aCT1 peptide | 0.08; 0.4; and 2.0 |
| Sodium Chloride (NaCl) | 0.9 |
| Hydroxypropyl Methylcellulose (HPMC), 4000 mPa · s | 0.5 |
| Purified Water | Q.S. |

TABLE 17

Formulation Assay Results

| Sample | Storage | Peptide Conc (mg/mL) | % Label claim |
| --- | --- | --- | --- |
| 0.8 mg/mL (Tubing/filter study) | Stored in plastic falcon tube overnight at 2-8° C. | 0.81 | 101.29 |
| 0.8 mg/mL (Tubing/filter study) | Stored in glass bottle overnight at 2-8° C. | 0.82 | 101.97 |
| 0.8 mg/mL solution in amber vials with pump | Frozen (−20° C.) | 0.82 | 102.51 |

TABLE 18

Optimal Formulation Properties

| Property | Eye Drop Formulation |
| --- | --- |
| Density | 0.99 g/mL |
| pH | 5.3 |
| Viscosity | 20.4 mPa · s |
| Osmolality | 288 mOsm/kg |

TABLE 19

Peptide Stability testing of optimal eye drop formulation.

| | 0.07% w/w (0.7 mg/ml) aCT1 peptide | | | 1.8% w/w (18 mg/ml) aCT1 peptide | | |
| --- | --- | --- | --- | --- | --- | --- |
| Temperature | 0 months | 1 months | 3 months | 0 months | 1 months | 3 months |
| −20° C. | 88.2 | 84.8 | 84.2 | 90.5 | 87.4 | 87.5 |
| 5° C. | 88.2 | 85.2 | 83.2 | 90.5 | 87.7 | 86.0 |
| 25° C. | 88.2 | 84.5 | 81.2 | 90.5 | 87.2 | 85.3 |

Example 8

Excipient Effects

Effects of various formulation components were assessed. Results are provided in Tables 20 and 21. NaCl provided better stabilization compared to sorbitol, particularly at concentrations above 50 mM. In addition, greater stability was observed at higher peptide concentrations.

TABLE 20

Effects of NaCl vs. sorbitol (20 mg/mL peptide at pH 6.5)

| Loss of Purity % | [NaCl] (mM) | Sorbitol (mM) |
| --- | --- | --- |
| 0.67 | 0.67 | 0.67 |
| 0.24 | 0.24 | 0.24 |
| 0.03 | 0.03 | 0.03 |
| 0.76 | 0.76 | 0.76 |
| 1.05 | 1.05 | 1.05 |

TABLE 21

Effects of [peptide]/pH

| Loss of Purity (%) | [peptide] (mg/mL) | pH |
| --- | --- | --- |
| 0.44 | 0.8 | 6.5 |
| 0.39 | 5 | 6.5 |
| 0.30 | 10 | 6.5 |
| 0.19 | 15 | 6.5 |
| 0.06 | 20 | 6.5 |
| 0.33 | 20 | 7.0 |
| 0.50 | 20 | 7.5 |

REFERENCES

1. Wu, C. et al. Risk Factors Associated With Acute Respiratory Distress Syndrome and Death in Patients With Coronavirus Disease 2019 Pneumonia in Wuhan, China. *JAMA Intern Med* (2020).
2. Koval, M. Claudin Heterogeneity and Control of Lung Tight Junctions. *Annual Review of Physiology* 75, 551-567 (2013).
3. Lin, L., Lu, L., Cao, W. & Li, T. Hypothesis for potential pathogenesis of SARS-CoV-2 infection—a review of immune changes in patients with viral pneumonia. *Emerg Microbes Infect*, 1-14 (2020).
4. Khan, S. et al. The emergence of a novel coronavirus (SARS-CoV-2), their biology and therapeutic options. *J Clin Microbiol* (2020).
5. Xu, Z. et al. Pathological findings of COVID-19 associated with acute respiratory distress syndrome. *Lancet Respir Med* (2020).
6. Yang, X. et al. Clinical course and outcomes of critically ill patients with SARS-CoV-2 pneumonia in Wuhan, China: a single-centered, retrospective, observational study. *The Lancet Respiratory Medicine* (2020).
7. Gu, J. & Korteweg, C. Pathology and pathogenesis of severe acute respiratory syndrome. *Am J Pathol* 170, 1136-1147 (2007).
8. Ghatnekar, G. S. et al. Connexin43 carboxyl-terminal peptides reduce scar progenitor and promote regenerative healing following skin wounding. *Regen Med* 4, 205-223 (2009).
9. Gourdie, R. G. et al. The unstoppable connexin43 carboxyl-terminus: new roles in gap junction organization and wound healing. *Ann N Y Acad Sci* 1080, 49-62 (2006).
10. Rhett, J. M. et al. Novel therapies for scar reduction and regenerative healing of skin wounds. *Trends Biotechnol* 26, 173-180 (2008).
11. Obert, E. et al. Targeting the tight junction protein, zonula occludens-1, with the connexin43 mimetic peptide, aCT1, reduces VEGF-dependent RPE pathophysiology. *J Mol Med* (Berl) 95, 535-552 (2017).
12. Grek, C. L. et al. Topical administration of a connexin43-based peptide augments healing of chronic neuropathic diabetic foot ulcers: A multicenter, randomized trial. *Wound Repair Regen* 23, 203-212 (2015).
13. Ghatnekar, G., Grek, C., Armstrong, D., Desai, S. & Gourdie, R. The Effect of a Connexin43-based peptide on the Healing of Chronic Venous Leg Ulcers: A Multicenter, Randomized Trial. *Journal of Investigative Dermatology* (2014).
14. Grek, C. L. et al. A Multicenter Randomized Controlled Trial Evaluating a Cx43-Mimetic Peptide in Cutaneous Scarring. *J Invest Dermatol* 137, 620-630 (2017).
15. Ghatnekar, G. S., Grek, C. L., Armstrong, D. G., Desai, S. C. & Gourdie, R. G. The effect of a connexin43-based Peptide on the healing of chronic venous leg ulcers: a multicenter, randomized trial. *The Journal of investigative dermatology* 135, 289-298 (2015).
16. Rhett, J. M., Jourdan, J. & Gourdie, R. G. Connexin 43 connexon to gap junction transition is regulated by zonula occludens-1. *Mol Biol Cell* 22, 1516-1528 (2011).
17. Niessen, H., Harz, H., Bedner, P., Kramer, K. & Willecke, K. Selective permeability of different connexin channels to the second messenger inositol 1,4,5-trisphosphate. *Journal of cell science* 113 (Pt 8), 1365-1372 (2000).
18. Martin, P. & Parkhurst, S. M. Parallels between tissue repair and embryo morphogenesis. *Development* 131, 3021-3034 (2004).
19. Bruzzone, S., Guida, L., Zocchi, E., Franco, L. & De Flora, A. Connexin 43 hemi channels mediate $Ca^{2+}$-regulated transmembrane $NAD+$ fluxes in intact cells. *FASEB J* 15, 10-12 (2001).
20. Stout, C. E., Costantin, J. L., Naus, C. C. & Charles, A. C. Intercellular calcium signaling in astrocytes via ATP release through connexin hemichannels. *J Biol Chem* 277, 10482-10488 (2002).
21. Ye, Z. C., Wyeth, M. S., Baltan-Tekkok, S. & Ransom, B. R. Functional hemichannels in astrocytes: a novel mechanism of glutamate release. *J Neurosci* 23, 3588-3596 (2003).
22. Cherian, P. P. et al. Mechanical strain opens connexin 43 hemichannels in osteocytes: a novel mechanism for the release of prostaglandin. *Mol Blot Cell* 16, 3100-3106 (2005).
23. Rana, S. & Dringen, R. Gap junction hemichannel-mediated release of glutathione from cultured rat astrocytes. Neuroscience letters 415, 45-48 (2007).
24. Saez, J. C., Retamal, M. A., Basilio, D., Bukauskas, F. F. & Bennett, M. V. Connexin-based gap junction hemichannels: gating mechanisms. *Biochimica et biophysica acta* 1711, 215-224 (2005).
25. Evans, W. H. & Boitano, S. Connexin mimetic peptides: specific inhibitors of gap-junctional intercellular communication. *Biochemical Society transactions* 29, 606-612 (2001).
26. Ramachandran, S., Xie, L. H., John, S. A., Subramaniam, S. & Lal, R. A novel role for connexin hemichannel in oxidative stress and smoking-induced cell injury. *PloS one* 2, e712 (2007).
27. Rhett, J. M., Fann, S. A. & Yost, M. J. Purinergic Signaling in Early Inflammatory Events of the Foreign Body Response: Modulating Extracellular ATP as an Enabling Technology for Engineered Implants and Tissues. *Tissue engineering*. Part B, Reviews (2014).
28. Retamal, M. A., Cortes, C. J., Reuss, L., Bennett, M. V. & Saez, J. C. S-nitrosylation and permeation through connexin 43 hemichannels in astrocytes: induction by oxidant stress and reversal by reducing agents. *Proceed-* ings of the National Academy of Sciences of the United States of America 103, 4475-4480 (2006).
29. Retamal, M. A., Schalper, K. A., Shoji, K. F., Bennett, M. V. & Saez, J. C. Opening of connexin 43 hemichannels is increased by lowering intracellular redox potential. *Proceedings of the National Academy of Sciences of the United States of America* 104, 8322-8327 (2007).
30. Ghatnekar, G., Grek, C., Armstrong, D. G., Desai, S. C. & Gourdie, R. The Effect of a Connexin43-based peptide on the Healing of Chronic Venous Leg Ulcers: A Multicenter, Randomized Trial. *J Invest Dermatol* (2014).
31. Ghatnekar, G. S., Grek, C. L., Armstrong, D. G., Desai, S. C. & Gourdie, R. G. The effect of a connexin43-based Peptide on the healing of chronic venous leg ulcers: a multicenter, randomized trial. *J Invest Dermatol* 135, 289-298 (2015).
32. Grek, C., et al. A Multicenter, Randomized, Controlled Trial Evaluating a Connexin43-Mimetic Peptide in Cutaneous Scarring. *Journal of Investigative Dermatology* (2016).
33. McAuliffe, J. et al. Replication of SARS coronavirus administered into the respiratory tract of African Green, rhesus and cynomolgus monkeys. *Virology* 330, 8-15 (2004).
34. Clay, C. et al. Primary severe acute respiratory syndrome coronavirus infection limits replication but not lung inflammation upon homologous rechallenge. *J Virol* 86, 4234-4244 (2012).
35. Clay, C. C. et al. Severe acute respiratory syndrome-coronavirus infection in aged nonhuman primates is associated with modulated pulmonary and systemic immune responses. *Immun Ageing* 11, 4 (2014).
36. Mandal, A., et al., Ocular delivery of proteins and peptides: Challenges and novel formulation approaches. Advanced drug delivery reviews, 2018. 126: p. 67-95.
37. Moore K, Ghatnekar G, Gourdie R, Potts JD. (2014) Impact of the Controlled Release of a Connexin 43Peptide on Corneal Wound Closure in an STZ Model of Type I Diabetes. PLoS One; 9, e86570.
38. Moore K, Bryant Z, Ghatnekar G, Singh U P, Gourdie R G, Potts J D (2013). A synthetic connexin 43 mimetic peptide augments corneal wound healing. Experimental Eye Research. 115:178-88
39. Giannos, S. A., et al., Formulation Stabilization and Disaggregation of Bevacizumab, Ranibizumab and Aflibercept in Dilute Solutions. Pharmaceutical research, 2018. 35(4): p. 78-78.
40. Kamerzell, T. J., et al., Protein-excipient interactions: Mechanisms and biophysical characterization applied to protein formulation development. Advanced Drug Delivery Reviews, 2011. 63(13): p. 1118-1159.
41. Zaki, I., Fitzgerald, P., Hardy, J. G. and Wilson, C. G. (1986), A comparison of the effect of viscosity on the precorneal residence of solutions in rabbit and man. Journal of Pharmacy and Pharmacology, 38: 463-466.

The invention claimed is:

1. A formulation comprising an active peptide having a molecular weight of about 1.0 kDa to about 10.0 kDa and hydroxypropyl methylcellulose (HPMC), wherein the formulation has a viscosity of about 18 to about 28 mPaS and is suitable for topical ocular delivery, and wherein the active peptide comprises the amino acid sequence of SEQ ID NO: 2.

2. The formulation of claim 1, wherein the HPMC is present in the formulation at a concentration of about 0.01% (w/w) to about 2.0% (w/w).

3. The formulation of claim 1, wherein the HPMC is present in the formulation at a concentration of about 0.05% (w/w) to about 0.5% (w/w).

4. The formulation of claim 1, wherein the formulation further comprises sodium chloride (NaCl).

5. The formulation of claim 4, wherein the NaCl is present at a concentration of about 0.7% to about 1.5% (w/w).

6. The formulation of claim 1, wherein the active peptide is present in the composition at a concentration of about 0.05% (w/w) to about 2.0% (w/w).

7. The formulation of claim 1, wherein the peptide comprises a cellular internalization sequence.

8. The formulation of claim 7, wherein the cellular internalization sequence comprises an amino acid sequence of a protein selected from a group consisting of Antennapedia, TAT, HIV-Tat, Penetratin, Antp-3A (Antp mutant), Buforin II, Transportan, MAP (model amphipathic peptide), K-FGF, Ku70, Prion, pVEC, Pep-1, SynB 1, Pep-7, HN-1, BGSC (Bis-Guanidinium-Spermidine-Cholesterol) and BGTC (Bis-Guanidinium-Tren-Cholesterol).

9. The formulation of claim 8, wherein the cellular internalization sequence is Antennapedia, and wherein the sequence comprises the amino acid sequence of SEQ ID NO:7.

10. The formulation of claim 9, wherein the peptide comprises the amino acid sequence selected from the group consisting of SEQ ID NO:8, SEQ ID NO:9, SEQ ID NO: 10, SEQ ID NO:11, and SEQ ID NO: 12.

11. The formulation of claim 10 wherein the peptide comprises the amino acid sequence of SEQ ID NO:9.

12. The formulation of claim 1, wherein the formulation is suitable for administration via eye drop.

13. A method of treating an ocular injury in a subject in need thereof, comprising topically administering a formulation of claim 1 to the eye of the subject.

14. The method of claim 13, wherein the formulation is administered to the immediately after the event that caused the ocular injury.

15. The method of claim 13, wherein the polypeptide is administered to the subject at least about 2 hours following the event that caused the ocular injury.

16. The method of claim 13, wherein the ocular injury is a corneal injury or a chemical or thermal burn injury, or wherein the injury is caused by a burn or explosion, or wherein the injury is caused by a chronic disease.

17. The method of claim 16, wherein the chronic disease is diabetes or retinal disease.

18. The method of claim 17, wherein the chronic disease is diabetic keratopathy.

19. The method of claim 13, wherein the injury is secondary to an ocular surgery, or wherein the subject suffers from a persistent or recurrent corneal epithelial defect, or wherein the ocular injury is a retinal injury.

20. The method of claim 19, wherein the persistent corneal epithelial defect arises from dry eye disease.

21. A method for accelerating corneal reepithelialization following an ocular injury in a subject, the method comprising topically administering a formulation of claim 1 to the eye of the subject.

22. The method of claim 21, wherein the ocular injury results from a surgery, a chemical injury, a corneal laceration injury, or chronic disease.

23. The method of claim 21, wherein the subject suffers from a persistent or recurrent corneal epithelial defect.

\* \* \* \* \*